United States Patent
Orengo et al.

(10) Patent No.: US 10,005,834 B2
(45) Date of Patent: Jun. 26, 2018

(54) BIOMARKERS RELATED TO INTERLEUKIN-33 (IL-33)-MEDIATED DISEASES AND USES THEREOF

(71) Applicant: Regeneron Pharmaceuticals, Inc., Tarrytown, NY (US)

(72) Inventors: Jamie M. Orengo, Cortlandt Manor, NY (US); Jeanne Allinne, New York, NY (US); Wen Fury, New York, NY (US); Yu Bai, Scarsdale, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days. days.

(21) Appl. No.: 15/285,772

(22) Filed: Oct. 5, 2016

(65) Prior Publication Data

US 2017/0096483 A1     Apr. 6, 2017

Related U.S. Application Data

(60) Provisional application No. 62/237,624, filed on Oct. 6, 2015.

(51) Int. Cl.

| | | |
|---|---|---|
| *A61K 39/395* | (2006.01) | |
| *A61K 39/00* | (2006.01) | |
| *A61K 38/00* | (2006.01) | |
| *C07K 16/24* | (2006.01) | |
| *A61K 38/17* | (2006.01) | |
| *A61K 45/06* | (2006.01) | |
| *G01N 33/68* | (2006.01) | |
| *C07K 14/575* | (2006.01) | |

(52) U.S. Cl.
CPC ........ *C07K 16/244* (2013.01); *A61K 38/1793* (2013.01); *A61K 39/3955* (2013.01); *A61K 45/06* (2013.01); *C07K 14/57527* (2013.01); *G01N 33/6893* (2013.01); *A61K 2039/505* (2013.01); *C07K 2317/21* (2013.01); *C07K 2317/24* (2013.01); *C07K 2317/56* (2013.01); *C07K 2317/76* (2013.01); *C07K 2319/30* (2013.01); *G01N 2333/54* (2013.01); *G01N 2333/585* (2013.01)

(58) Field of Classification Search
None
See application file for complete search history.

(56) References Cited

U.S. PATENT DOCUMENTS

| | | | |
|---|---|---|---|
| 2011/0189698 A1* | 8/2011 | Burns ................ | G01N 33/6893 435/7.4 |
| 2014/0271642 A1 | 9/2014 | Murphy et al. | |
| 2014/0271658 A1 | 9/2014 | Murphy et al. | |

FOREIGN PATENT DOCUMENTS

| | | |
|---|---|---|
| WO | WO 15/061441 A1 | 4/2015 |
| WO | 2017-062456 A2 | 4/2017 |

OTHER PUBLICATIONS

Miller 2011. J. of Inflammation. 8:22.*
Alves-Filho et al., "Interleukin-33 attenuates sepsis by enhancing neutrophil influx to the site of infection," Nature Medicine, 16(6):708-713, doi: 10.1038/nm.2156, (2010).
Baines et al., "Sputum gene expression signature of 6 biomarkers discriminates asthma inflammatory phenotypes," Journal of Allergy and Clinical Immunology, 133(4):997-1007, doi:10.1016/j.jaci.2013.12.1091, (2014).
Chang DI et al., "Changes in plasma interleukin-33 concentration in sepsis and its correlation with seriousness of sepsis," Chinese Critical Care Medicine, Abstract only, 27(2):138-142, (2015).
Jia et al., "Periostin is a systemic biomarker of eosinophilic airway inflammation in asthmatic patients," Journal of Allergy and Clinical Immunology, 130(30):647-654, doi: 10.1016/J.JACI.2012.06.025, (2012).
Long et al., "Procalcitonin guidance for reduction of antibiotic use in patients hospitalized with severe acute exacerbations of asthma: a randomized controlled study with 12-month follow-up," Critical Care, 18(5):471, 9 pages, doi: 10.1186/S13054-014-0471-7, (2014).
Louten et al., "Biomarkers of Disease and Treatment in Murine and Cynomolgus Models of Chronic Asthma," Biomarker Insights, pp. 87-104, doi: 10.4137/BMI.S9776, (2012).
WIPO Application No. PCT/US2016/055502, PCT Invitation to Pay Additional Fees dated Feb. 3, 2017.
WIPO Application No. PCT/US2016/055502, PCT International Search Report and Written Opinion of the International Searching Authority dated Mar. 31, 2017; 25 pages.

* cited by examiner

*Primary Examiner* — Shulamith H Shafer
(74) *Attorney, Agent, or Firm* — Schwabe, Williamson & Wyatt PC; Veronica Mallon

(57) ABSTRACT

The present invention relates to the identification of certain biomarkers for use in identifying patients who have, or are likely to develop an IL-33 mediated disease or disorder and who are more likely to respond to therapy with an IL-33 antagonist. The invention also relates to methods of treatment of an IL-33-mediated disease or disorder in a patient by administering an IL-33 antagonist to the patient in need thereof and monitoring the effectiveness of therapy using the biomarkers described herein. Also provided are methods for decreasing the level of at least one biomarker in a subject suffering from an IL-33-mediated disease or disorder, and methods for treating such diseases or disorders according to the expression levels of one or more biomarkers. The methods of the present invention comprise administering to a subject in need thereof a pharmaceutical composition comprising an interleukin-33 antagonist.

27 Claims, 14 Drawing Sheets

SEQUENCE LISTING

```
<160> NUMBER OF SEQ ID NOS: 335

<210> SEQ ID NO 1
<211> LENGTH: 366
<212> TYPE: DNA
<213> ORGANISM: Artificial Sequence
<220> FEATURE:
<223> OTHER INFORMATION: synthetic

<400> SEQUENCE: 1
caggtgcagc tggtggagtc tgggggaggc gtggtccagc ctgggaggtc cctgagactc      60
tcctgtgcag cgtctggatt cacctcagt agttatggca tgcattgggt ccgccaggct     120
ccaggcaagg ggctggagtg ggtggcagtt atatggtatg atggaagaaa taaatactat     180
acagactccg tgaagggccg attcaccatc tccagagaca attccaagaa cacgctgtat     240
ctgcaaatgg acagcctgag agccgaggac acggctgtgt attactgtgc gagagagagg     300
tatatcagca gctattatgg ggggttcgac ccctggggcc agggagcccct ggtcaccgtc     360 tcctca                                                                366

<210> SEQ ID NO 2
<211> LENGTH: 122
<212> TYPE: PRT
<213> ORGANISM: Artificial Sequence
<220> FEATURE:
<223> OTHER INFORMATION: synthetic

<400> SEQUENCE: 2

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30
```

Gly Met His Trp Val Arg Gln Ala Pro Gly Lys Gly Leu Glu Trp Val
             35                  40                  45

Ala Val Ile Trp Tyr Asp Gly Arg Asn Lys Tyr Tyr Thr Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Ala Glu Asp Thr Ala Val Tyr Tyr Cys
                 85                  90                  95

Ala Arg Glu Arg Tyr Ile Ser Ser Tyr Tyr Gly Gly Phe Asp Pro Trp
             100                 105                 110

Gly Gln Gly Ala Leu Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcacct tcagtagtta tggc                                    24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Phe Ser Ser Tyr Gly
 1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
atatggtatg atggaagaaa taaa                                    24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Trp Tyr Asp Gly Arg Asn Lys
 1               5

<210> SEQ ID NO 7
<211> LENGTH: 45
<212> TYPE: DNA
<213> ORGANISM: Artificial Sequence
<220> FEATURE:
<223> OTHER INFORMATION: synthetic

<400> SEQUENCE: 7
gcgagagaga ggtatatcag cagctattat ggggggttcg acccc              45

<210> SEQ ID NO 8
<211> LENGTH: 15
<212> TYPE: PRT
<213> ORGANISM: Artificial Sequence
<220> FEATURE:
<223> OTHER INFORMATION: synthetic

<400> SEQUENCE: 8

```
Ala Arg Glu Arg Tyr Ile Ser Ser Tyr Tyr Gly Gly Phe Asp Pro
 1               5                  10                  15
```

<210> SEQ ID NO 9
<211> LENGTH: 321
<212> TYPE: DNA
<213> ORGANISM: Artificial Sequence
<220> FEATURE:
<223> OTHER INFORMATION: synthetic

<400> SEQUENCE: 9

```
gacatccaga tgacccagtc tccatcctcc gtgtctgcat ctgtaggaga cagagtcacc    60
atcacttgtc gggcgagtca gggtattagt agttggttag cctggtatca gcagaaacca   120
gggaaagccc ctaaggtcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tcccattcac tttcggccct   300
gggaccaaac tggatatcaa g                                             321
```

<210> SEQ ID NO 10
<211> LENGTH: 107
<212> TYPE: PRT
<213> ORGANISM: Artificial Sequence
<220> FEATURE:
<223> OTHER INFORMATION: synthetic

<400> SEQUENCE: 10

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Val Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Leu Asp Ile Lys
            100                 105
```

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11

```
cagggtatta gtagttgg                                                  18
```

<210> SEQ ID NO 12

```
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Gly Ile Ser Ser Trp
 1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcatcc                                                                   9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
 1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacaggcta acagtttccc attcact                                              27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Ala Asn Ser Phe Pro Phe Thr
 1               5

<210> SEQ ID NO 17
<211> LENGTH: 357
<212> TYPE: DNA
<213> ORGANISM: Artificial Sequence
<220> FEATURE:
<223> OTHER INFORMATION: synthetic

<400> SEQUENCE: 17
gaggtgcagc tgttggagtc tgggggagac ttggtacagc ctggggggtc cctgagactc          60
tcctgtgcag cctctggatt caccttcagc agctatgcca tgagctgggt ccgccaggct         120
ccagggaagg ggctggagtg gtctcagtt attagtggta gtggaagtag cacagactac         180
gcagactccg tgaagggccg gttcaccatt tccagagaca attccaggga cacgctgcat         240
```

```
ctgcaaatga acagcctgag agccgaggac acggccgtat attactgtgc gaaaacgttc    300
tactacttct acggtttgga cgtctggggc caagggacca cggtcaccgt ctcctca      357
```

<210> SEQ ID NO 18
<211> LENGTH: 119
<212> TYPE: PRT
<213> ORGANISM: Artificial Sequence
<220> FEATURE:
<223> OTHER INFORMATION: synthetic

<400> SEQUENCE: 18

```
Glu Val Gln Leu Leu Glu Ser Gly Gly Asp Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Ser Ser Thr Asp Tyr Ala Asp Ser Val
    50                  55                  60

Lys Gly Arg Phe Thr Ile Ser Arg Asp Asn Ser Arg Asp Thr Leu His
65                  70                  75                  80

Leu Gln Met Asn Ser Leu Arg Ala Glu Asp Thr Ala Val Tyr Tyr Cys
                85                  90                  95

Ala Lys Thr Phe Tyr Tyr Phe Tyr Gly Leu Asp Val Trp Gly Gln Gly
            100                 105                 110

Thr Thr Val Thr Val Ser Ser
        115
```

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19

```
ggattcacct tcagcagcta tgcc                                          24
```

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

```
Gly Phe Thr Phe Ser Ser Tyr Ala
 1               5
```

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21

```
attagtggta gtggaagtag caca                                          24
```

<210> SEQ ID NO 22
<211> LENGTH: 8
<212> TYPE: PRT

<213> ORGANISM: Artificial Sequence
<220> FEATURE:
<223> OTHER INFORMATION: synthetic

<400> SEQUENCE: 22

Ile Ser Gly Ser Gly Ser Ser Thr
1               5

<210> SEQ ID NO 23
<211> LENGTH: 36
<212> TYPE: DNA
<213> ORGANISM: Artificial Sequence
<220> FEATURE:
<223> OTHER INFORMATION: synthetic

<400> SEQUENCE: 23
gcgaaaacgt tctactactt ctacggtttg gacgtc                          36

<210> SEQ ID NO 24
<211> LENGTH: 12
<212> TYPE: PRT
<213> ORGANISM: Artificial Sequence
<220> FEATURE:
<223> OTHER INFORMATION: synthetic

<400> SEQUENCE: 24

Ala Lys Thr Phe Tyr Tyr Phe Tyr Gly Leu Asp Val
1               5                   10

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25
gacatccaga tgacccagtc tccatcctcc ctgtctgcat ctttaagaga cagagtcacc    60
atcacttgcc gggcgagtca gggcattagc aattatttag cctggtatca gcagaaacca   120
gggaaagttc ctaaggtcct aatctatgct gcatccactt tgcaatcagg ggtcccatct   180
cggttcagtg gcagtggatc tgggacagtt ttcactctca ccatcagcag cctgcagact   240
gaagatgttg caacttatta ctgtcaaaag tatagcagtg ccccattcac tttcggccct   300
gggaccaaag tggatatcaa a                                            321

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Leu Ser Ala Ser Leu Arg
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Val Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Val Phe Thr Leu Thr Ile Ser Ser Leu Gln Thr

```
                65                  70                  75                  80
Glu Asp Val Ala Thr Tyr Tyr Cys Gln Lys Tyr Ser Ser Ala Pro Phe
                    85                  90                  95
Thr Phe Gly Pro Gly Thr Lys Val Asp Ile Lys
                100                 105
```

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagggcatta gcaattat                                                   18

<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

```
Gln Gly Ile Ser Asn Tyr
1               5
```

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 gctgcatcc                                                              9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

```
Ala Ala Ser
1
```

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
caaaagtata gcagtgcccc attcact                                         27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Gln Lys Tyr Ser Ser Ala Pro Phe Thr
1               5

<210> SEQ ID NO 33
<211> LENGTH: 351
<212> TYPE: DNA
<213> ORGANISM: Artificial Sequence
<220> FEATURE:
<223> OTHER INFORMATION: synthetic

<400> SEQUENCE: 33
caggtgcttc tggtacagtc tggggctgag gtgaagaagc ctggggccac agtgaaggtc     60
tcctgcaagg cttctggatc cactttcacc ggctactata tgcactgggt gcgacaggcc    120
cctggacaag gcttgagtg gatgggatgg atcaaccctaacaatggtgg cacaaactat     180 gcacagaagt tcagggcag gtcaccatg accaggaca cgtccatcag cacagcctac       240
atggaattga gcaggctgag atctgacgac acggccgtat attactgtgc gagagagttg    300
cggtataact ggaagtcctg gggccaggga accctggtca ccgtctcctc a             351

<210> SEQ ID NO 34
<211> LENGTH: 117
<212> TYPE: PRT
<213> ORGANISM: Artificial Sequence
<220> FEATURE:
<223> OTHER INFORMATION: synthetic

<400> SEQUENCE: 34

Gln Val Leu Leu Val Gln Ser Gly Ala Glu Val Lys Lys Pro Gly Ala
1               5                   10                  15

Thr Val Lys Val Ser Cys Lys Ala Ser Gly Ser Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Leu Arg Tyr Asn Trp Lys Ser Trp Gly Gln Gly Thr Leu
            100                 105                 110

Val Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggatccactt tcaccggcta ctat                                            24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Ser Thr Phe Thr Gly Tyr Tyr
1               5

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37 atcaaccta acaatggtgg caca                                         24

<210> SEQ ID NO 38
<211> LENGTH: 8
<212> TYPE: PRT
<213> ORGANISM: Artificial Sequence
<220> FEATURE:
<223> OTHER INFORMATION: synthetic

<400> SEQUENCE: 38

Ile Asn Pro Asn Asn Gly Gly Thr
1               5

<210> SEQ ID NO 39
<211> LENGTH: 30
<212> TYPE: DNA
<213> ORGANISM: Artificial Sequence
<220> FEATURE:
<223> OTHER INFORMATION: synthetic

<400> SEQUENCE: 39
gcgagagagt tgcggtataa ctggaagtcc                                  30

<210> SEQ ID NO 40
<211> LENGTH: 10
<212> TYPE: PRT
<213> ORGANISM: Artificial Sequence
<220> FEATURE:
<223> OTHER INFORMATION: synthetic

<400> SEQUENCE: 40

Ala Arg Glu Leu Arg Tyr Asn Trp Lys Ser
1               5                   10

<210> SEQ ID NO 41
<211> LENGTH: 324
<212> TYPE: DNA
<213> ORGANISM: Artificial Sequence
<220> FEATURE:
<223> OTHER INFORMATION: synthetic

<400> SEQUENCE: 41
gaaattgtgt tgacgcagtc tccaggcacc ctgtctttgt ctccagggga aagagtcacc    60
ctctcctgca gggccagtca gagtgttggc aggccctact tagcctggta ccaacagata   120
cctggccagg ctcccaggct cctcatctat ggtgcatcca gcagggccac tgacatccca   180
gacaggttca gtggcaatgg gtctgggaca gacttcactc tcaccatcag tagactggag   240
cctgaagatt ttgcagtgta ttactgtcag cagtatgata attcccctta cttttggc    300 caggggacca ggctggagat caaa                                         324

```
<210> SEQ ID NO 42
<211> LENGTH: 108
<212> TYPE: PRT
<213> ORGANISM: Artificial Sequence
<220> FEATURE:
<223> OTHER INFORMATION: synthetic

<400> SEQUENCE: 42

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Gly Arg Pro
            20                  25                  30

Tyr Leu Ala Trp Tyr Gln Gln Ile Pro Gly Gln Ala Pro Arg Leu Leu
        35                  40                  45

Ile Tyr Gly Ala Ser Ser Arg Ala Thr Asp Ile Pro Asp Arg Phe Ser
50                  55                  60

Gly Asn Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Asn Ser Pro
                85                  90                  95

Tyr Thr Phe Gly Gln Gly Thr Arg Leu Glu Ile Lys
            100                 105

<210> SEQ ID NO 43
<211> LENGTH: 21
<212> TYPE: DNA
<213> ORGANISM: Artificial Sequence
<220> FEATURE:
<223> OTHER INFORMATION: synthetic

<400> SEQUENCE: 43
cagagtgttg gcaggcccta c                                        21

<210> SEQ ID NO 44
<211> LENGTH: 7
<212> TYPE: PRT
<213> ORGANISM: Artificial Sequence
<220> FEATURE:
<223> OTHER INFORMATION: synthetic

<400> SEQUENCE: 44

Gln Ser Val Gly Arg Pro Tyr
1               5

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 ggtgcatcc                                                       9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Gly Ala Ser
1
```

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
cagcagtatg ataattcccc ttatact                                    27

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Gln Gln Tyr Asp Asn Ser Pro Tyr Thr
 1               5

<210> SEQ ID NO 49
<211> LENGTH: 366
<212> TYPE: DNA
<213> ORGANISM: Artificial Sequence
<220> FEATURE:
<223> OTHER INFORMATION: synthetic

<400> SEQUENCE: 49
gaggtgcagc tggtggagtc tgggggaggc ttggtacaac ctgggggtc cctgagactc    60 tcctgtgcag cctctggatt cacctttaga agctttgcca tgagctgggt ccgccaggct   120
ccagggaagg ggctggaatt ggtctcagat ctcaggacta gtggtggtag tacatactac   180
gcagactccg tgaagggccg gctcaccatc tccagagaca attccaagaa cacgctgtat   240
ctgcaaatga acagcctgag agccgaggac acggccgtat attactgtgc gaaaagccac   300
tatagcacca gctggttcgg gggctttgac tactggggcc agggaaccct ggtcactgtc   360
tcctca                                                              366

<210> SEQ ID NO 50
<211> LENGTH: 122
<212> TYPE: PRT
<213> ORGANISM: Artificial Sequence
<220> FEATURE:
<223> OTHER INFORMATION: synthetic

<400> SEQUENCE: 50

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg Ser Phe
             20                  25                  30

Ala Met Ser Trp Val Arg Gln Ala Pro Gly Lys Gly Leu Glu Leu Val
         35                  40                  45

Ser Asp Leu Arg Thr Ser Gly Gly Ser Thr Tyr Tyr Ala Asp Ser Val
     50                  55                  60

Lys Gly Arg Leu Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser His Tyr Ser Thr Ser Trp Phe Gly Gly Phe Asp Tyr Trp

Gly Gln Gly Thr Leu Val Thr Val Ser Ser
          115                 120

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggattcacct ttagaagctt tgcc                                          24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Phe Thr Phe Arg Ser Phe Ala
1               5

<210> SEQ ID NO 53
<211> LENGTH: 24
<212> TYPE: DNA
<213> ORGANISM: Artificial Sequence
<220> FEATURE:
<223> OTHER INFORMATION: synthetic

<400> SEQUENCE: 53
ctcaggacta gtggtggtag taca                                          24

<210> SEQ ID NO 54
<211> LENGTH: 8
<212> TYPE: PRT
<213> ORGANISM: Artificial Sequence
<220> FEATURE:
<223> OTHER INFORMATION: synthetic

<400> SEQUENCE: 54

Leu Arg Thr Ser Gly Gly Ser Thr
1               5

<210> SEQ ID NO 55
<211> LENGTH: 45
<212> TYPE: DNA
<213> ORGANISM: Artificial Sequence
<220> FEATURE:
<223> OTHER INFORMATION: synthetic

<400> SEQUENCE: 55
gcgaaaagcc actatagcac cagctggttc gggggctttg actac              45

<210> SEQ ID NO 56
<211> LENGTH: 15
<212> TYPE: PRT
<213> ORGANISM: Artificial Sequence
<220> FEATURE:
<223> OTHER INFORMATION: synthetic

<400> SEQUENCE: 56

Ala Lys Ser His Tyr Ser Thr Ser Trp Phe Gly Gly Phe Asp Tyr
1               5                   10                  15

```
<210> SEQ ID NO 57
<211> LENGTH: 321
<212> TYPE: DNA
<213> ORGANISM: Artificial Sequence
<220> FEATURE:
<223> OTHER INFORMATION: synthetic

<400> SEQUENCE: 57
gacatccaga tgacccagtc tccatcttcc gtgtctgctt ctgtaggaga cagagtcacc      60
atcacttgtc gggcgagtca gggttttagc agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcaccaa cctgcagcct     240
gaagattttg caacttacta ttgtcaacag gctaacagtt tccctctcac tttcggcgga     300
gggaccaagg tggagatcaa a                                               321

<210> SEQ ID NO 58
<211> LENGTH: 107
<212> TYPE: PRT
<213> ORGANISM: Artificial Sequence
<220> FEATURE:
<223> OTHER INFORMATION: synthetic

<400> SEQUENCE: 58

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Phe Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Thr Asn Leu Gln Pro
 65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59
cagggtttta gcagctgg                                                    18

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

Gln Gly Phe Ser Ser Trp
  1               5
```

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 gctgcatcc                                                                     9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Ala Ser
 1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
caacaggcta acagtttccc tctcact                                                27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Gln Gln Ala Asn Ser Phe Pro Leu Thr
 1               5

<210> SEQ ID NO 65
<211> LENGTH: 366
<212> TYPE: DNA
<213> ORGANISM: Artificial Sequence
<220> FEATURE:
<223> OTHER INFORMATION: synthetic

<400> SEQUENCE: 65
gaggtgcagc tggtggagtc tgggggaggc ttggtacagc ctgggggtc cctgagactc              60 tcctgtgcag cctctggatt cacgtttagc agctatgtca tgagctgggt ccgccaggct            120
ccagggaagg ggctgagtg gtctcaagt attagtggta atggtggtag cacaaactac             180
gcagactccg tgaagggccg gttcaccatc tccagagaca attccaagaa cacgctgttt            240
ctggaaatga acagcctgag agccgaggac acggccgtat attactgtgc gaaatcactg            300
ggaactacca cgactttttt ggggtttgac tattggggcc agggaaccct ggtcaccgtc            360
tcctca                                                                      366

<210> SEQ ID NO 66
<211> LENGTH: 122
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Ser Ile Ser Gly Asn Gly Gly Ser Thr Asn Tyr Ala Asp Ser Val
    50                  55                  60

Lys Gly Arg Phe Thr Ile Ser Arg Asp Asn Ser Lys Asn Thr Leu Phe
65                  70                  75                  80

Leu Glu Met Asn Ser Leu Arg Ala Glu Asp Thr Ala Val Tyr Tyr Cys
                85                  90                  95

Ala Lys Ser Leu Gly Thr Thr Thr Thr Phe Leu Gly Phe Asp Tyr Trp
            100                 105                 110

Gly Gln Gly Thr Leu Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcacgt ttagcagcta tgtc                                      24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Phe Ser Ser Tyr Val
1               5

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
attagtggta atggtggtag caca                                      24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Ile Ser Gly Asn Gly Gly Ser Thr
1               5

<210> SEQ ID NO 71
<211> LENGTH: 45
<212> TYPE: DNA
<213> ORGANISM: Artificial Sequence
<220> FEATURE:
<223> OTHER INFORMATION: synthetic

<400> SEQUENCE: 71
gcgaaatcac tgggaactac cacgactttt ttggggtttg actat            45

<210> SEQ ID NO 72
<211> LENGTH: 15
<212> TYPE: PRT
<213> ORGANISM: Artificial Sequence
<220> FEATURE:
<223> OTHER INFORMATION: synthetic

<400> SEQUENCE: 72

Ala Lys Ser Leu Gly Thr Thr Thr Thr Phe Leu Gly Phe Asp Tyr
 1               5                  10                  15

<210> SEQ ID NO 73
<211> LENGTH: 321
<212> TYPE: DNA
<213> ORGANISM: Artificial Sequence
<220> FEATURE:
<223> OTHER INFORMATION: synthetic

<400> SEQUENCE: 73
gacatccaga tgacccagtc tccatcttcc gtgtctgcat ctgtaggaga cagagtcacc       60
atcacttgtc gggcgagtca gggtattagc agctggttag cctggtatca gcagaaacca     120
gggaaagccc ctaaactcct gatctatgct gcatccagtt tgcaaagtgg ggtcccatca     180
aggttcagcg gcagtggatc tgggacatat ttcactctca ccatcagcag cctgcagcct     240
gaagattttg caacttacta ttgtcaacag gctaacagtt tccctctcac tttcggcgga     300
gggaccaagg tggagatcaa a                                              321

<210> SEQ ID NO 74
<211> LENGTH: 107
<212> TYPE: PRT
<213> ORGANISM: Artificial Sequence
<220> FEATURE:
<223> OTHER INFORMATION: synthetic

<400> SEQUENCE: 74

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Tyr Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: synthetic

<400> SEQUENCE: 75
cagggtatta gcagctgg                                                 18

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

Gln Gly Ile Ser Ser Trp
 1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 gctgcatcc                                                            9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Ala Ala Ser
 1

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
caacaggcta acagtttccc tctcact                                       27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Gln Gln Ala Asn Ser Phe Pro Leu Thr
 1               5

<210> SEQ ID NO 81
<211> LENGTH: 363
<212> TYPE: DNA
<213> ORGANISM: Artificial Sequence
<220> FEATURE:
<223> OTHER INFORMATION: synthetic

<400> SEQUENCE: 81
caggtgcagc tgcaggagtc gggcccagga ctggtgaagc cttcggagac cctgtccctc    60
acctgcactg tctctggtgg ctccatcagt agttattact ggagctggat ccggcagccc   120
ccagggaagg gactggagtt gattgggtat atttattaca gtgggagcac caattataac   180
ccctccctca gagtcgagt caccatatct gtagacacgt ccaagaacca cttctccctg   240
aagctgagct ctgtgaccgc tgcggacacg gccgtatatt actgtgcgag atcccagtat   300
accagtagtt ggtacggttc ttttgatatc tggggccaag ggacaatggt caccgtctct   360
tca                                                                  363

<210> SEQ ID NO 82
<211> LENGTH: 121
<212> TYPE: PRT
<213> ORGANISM: Artificial Sequence
<220> FEATURE:
<223> OTHER INFORMATION: synthetic

<400> SEQUENCE: 82

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Leu Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn His Phe Ser Leu
65                  70                  75                  80

Lys Leu Ser Ser Val Thr Ala Ala Asp Thr Ala Val Tyr Tyr Cys Ala
                85                  90                  95

Arg Ser Gln Tyr Thr Ser Ser Trp Tyr Gly Ser Phe Asp Ile Trp Gly
            100                 105                 110

Gln Gly Thr Met Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
ggtggctcca tcagtagtta ttac                                            24

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

Gly Gly Ser Ile Ser Ser Tyr Tyr
 1               5

```
<210> SEQ ID NO 85
<211> LENGTH: 21
<212> TYPE: DNA
<213> ORGANISM: Artificial Sequence
<220> FEATURE:
<223> OTHER INFORMATION: synthetic

<400> SEQUENCE: 85
atttattaca gtgggagcac c                                              21

<210> SEQ ID NO 86
<211> LENGTH: 7
<212> TYPE: PRT
<213> ORGANISM: Artificial Sequence
<220> FEATURE:
<223> OTHER INFORMATION: synthetic

<400> SEQUENCE: 86

Ile Tyr Tyr Ser Gly Ser Thr
 1               5

<210> SEQ ID NO 87
<211> LENGTH: 45
<212> TYPE: DNA
<213> ORGANISM: Artificial Sequence
<220> FEATURE:
<223> OTHER INFORMATION: synthetic

<400> SEQUENCE: 87
gcgagatccc agtataccag tagttggtac ggttcttttg atatc                    45

<210> SEQ ID NO 88
<211> LENGTH: 15
<212> TYPE: PRT
<213> ORGANISM: Artificial Sequence
<220> FEATURE:
<223> OTHER INFORMATION: synthetic

<400> SEQUENCE: 88

Ala Arg Ser Gln Tyr Thr Ser Ser Trp Tyr Gly Ser Phe Asp Ile
 1               5                  10                  15

<210> SEQ ID NO 89
<211> LENGTH: 321
<212> TYPE: DNA
<213> ORGANISM: Artificial Sequence
<220> FEATURE:
<223> OTHER INFORMATION: synthetic

<400> SEQUENCE: 89
gacatccaga tgacccagtc tccatcttcc gtgtctgcat ctgtaggaga cagagtcacc     60
atcacttgtc gggcgagtca gggtattagc acctggttag cctggtttca gcagaaacca   120
gggaaagccc ctaagctcct gatctatgct gcatccactt tacaaggtgg ggtcccatca   180
aggttcagcg gcagtggatc tgggccagaa ttcactctca ccatcagcag cctgcagcct   240
gaagattttg caacttacta ttgtcaacag gctaacagtt cccgtggac gttcggccaa    300 gggaccaagg tggaaatcaa a                                             321

<210> SEQ ID NO 90
<211> LENGTH: 107
<212> TYPE: PRT
<213> ORGANISM: Artificial Sequence
<220> FEATURE:
<223> OTHER INFORMATION: synthetic
```

<400> SEQUENCE: 90

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Thr Trp
            20                  25                  30

Leu Ala Trp Phe Gln Gln Lys Pro Gly Lys Ala Pro Lys Leu Leu Ile
        35                  40                  45

Tyr Ala Ala Ser Thr Leu Gln Gly Gly Val Pro Ser Arg Phe Ser Gly
50                  55                  60

Ser Gly Ser Gly Pro Glu Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91
cagggtatta gcacctgg                                                 18

<210> SEQ ID NO 92
<211> LENGTH: 6
<212> TYPE: PRT
<213> ORGANISM: Artificial Sequence
<220> FEATURE:
<223> OTHER INFORMATION: synthetic

<400> SEQUENCE: 92

Gln Gly Ile Ser Thr Trp
1               5

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 gctgcatcc                                                            9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Ala Ala Ser
1

<210> SEQ ID NO 95
<211> LENGTH: 27
<212> TYPE: DNA
<213> ORGANISM: Artificial Sequence
<220> FEATURE:

<223> OTHER INFORMATION: synthetic

<400> SEQUENCE: 95
caacaggcta acagtttccc gtggacg                                          27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

Gln Gln Ala Asn Ser Phe Pro Trp Thr
 1               5

<210> SEQ ID NO 97
<211> LENGTH: 366
<212> TYPE: DNA
<213> ORGANISM: Artificial Sequence
<220> FEATURE:
<223> OTHER INFORMATION: synthetic

<400> SEQUENCE: 97
caggttcagc tggtgcagtc tggagctgag gtgaagaagc ctggggcctc agtgaaggtc       60
tcctgcaagg cctctggtta cacctttaac agctatggta tcagctgggt gcgacaggcc      120
cctggacaag gcttgagtg atgggatgg atcagctccc acaatggtaa cagtcactat       180
gtacagaagt tccagggcag agtctccatg accacagaca catccacgag tacagcctac      240
atggaactga ggagccttag atctgacgac acggccgtgt attactgtgc gagacactcg      300
tataccacca gctggtacgg gggttttgac tattggggcc agggaaccct ggtcaccgtc      360
tcctca                                                                 366

<210> SEQ ID NO 98
<211> LENGTH: 122
<212> TYPE: PRT
<213> ORGANISM: Artificial Sequence
<220> FEATURE:
<223> OTHER INFORMATION: synthetic

<400> SEQUENCE: 98

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Asn Ser Tyr
                20                  25                  30

Gly Ile Ser Trp Val Arg Gln Ala Pro Gly Gln Gly Leu Glu Trp Met
            35                  40                  45

Gly Trp Ile Ser Ser His Asn Gly Asn Ser His Tyr Val Gln Lys Phe
        50                  55                  60

Gln Gly Arg Val Ser Met Thr Thr Asp Thr Ser Thr Ser Thr Ala Tyr
 65                 70                  75                  80

Met Glu Leu Arg Ser Leu Arg Ser Asp Asp Thr Ala Val Tyr Tyr Cys
                85                  90                  95

Ala Arg His Ser Tyr Thr Thr Ser Trp Tyr Gly Gly Phe Asp Tyr Trp
                100                 105                 110

Gly Gln Gly Thr Leu Val Thr Val Ser Ser
            115                 120

<210> SEQ ID NO 99

```
<211> LENGTH: 24
<212> TYPE: DNA
<213> ORGANISM: Artificial Sequence
<220> FEATURE:
<223> OTHER INFORMATION: synthetic

<400> SEQUENCE: 99
ggttacacct taacagcta tggt                                            24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Tyr Thr Phe Asn Ser Tyr Gly
 1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
atcagctccc acaatggtaa cagt                                           24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Ser Ser His Asn Gly Asn Ser
 1               5

<210> SEQ ID NO 103
<211> LENGTH: 45
<212> TYPE: DNA
<213> ORGANISM: Artificial Sequence
<220> FEATURE:
<223> OTHER INFORMATION: synthetic

<400> SEQUENCE: 103
gcgagacact cgtataccac cagctggtac ggggttttg actat                    45

<210> SEQ ID NO 104
<211> LENGTH: 15
<212> TYPE: PRT
<213> ORGANISM: Artificial Sequence
<220> FEATURE:
<223> OTHER INFORMATION: synthetic

<400> SEQUENCE: 104

Ala Arg His Ser Tyr Thr Thr Ser Trp Tyr Gly Gly Phe Asp Tyr
 1               5                  10                  15

<210> SEQ ID NO 105
<211> LENGTH: 321
<212> TYPE: DNA
<213> ORGANISM: Artificial Sequence
<220> FEATURE:
```

<223> OTHER INFORMATION: synthetic

<400> SEQUENCE: 105

```
gacatccaga tgacccagtc tccatcttcc gtgtctgcat ctgtaggaga cagagtcacc      60
atcacttgtc gggcgagtca gggttttagc agctggttag cctggtatca gcagaaacca     120
gggaaagccc ctcagctcct gatctatgct gcatccagtt tgcaaagtgg ggtcccatca     180
aggttcagcg gcagtggatc tgggtcagat tcactctca ccatcagcag cctgcagcct      240
gaagattttg caacttacta ttgtcaacag gctaacagtt tccctctcac tttcggcgga     300
gggaccaagg tggagatcaa a                                                321
```

<210> SEQ ID NO 106
<211> LENGTH: 107
<212> TYPE: PRT
<213> ORGANISM: Artificial Sequence
<220> FEATURE:
<223> OTHER INFORMATION: synthetic

<400> SEQUENCE: 106

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Phe Ser Ser Trp
             20                  25                  30

Leu Ala Trp Tyr Gln Gln Lys Pro Gly Lys Ala Pro Gln Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Ser Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Leu
                 85                  90                  95

Thr Phe Gly Gly Gly Thr Lys Val Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107

```
cagggtttta gcagctgg                                                    18
```

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Gln Gly Phe Ser Ser Trp
 1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 gctgcatcc                                                                      9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Ala Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
caacaggcta acagtttccc tctcact                                                 27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

Gln Gln Ala Asn Ser Phe Pro Leu Thr
 1               5

<210> SEQ ID NO 113
<211> LENGTH: 366
<212> TYPE: DNA
<213> ORGANISM: Artificial Sequence
<220> FEATURE:
<223> OTHER INFORMATION: synthetic

<400> SEQUENCE: 113
gaggtgcagc tggtggagtc cggggggaggc ttggttcagc cggggggtc cctgagactc            60 tcctgtgcag cctctggaat caccttgagc agctatggca tgagctgggt ccgccaggct           120
ccagggaagg gactggagtg ggtcgcatcc attttggta gtggtggtgg cccatactac            180
gcagactccg tgaagggccg gttcaccatg tccagagaca attccaagaa cacgctgtat           240
ttgcaaatga acagcctgag agccgaggac acggccgtat attattgtgc gaaagatcga           300
tacagtggga gctactacgg aggttttgac tactggggcc ggggaaccct ggtcaccgtc           360
tcctca                                                                    366

<210> SEQ ID NO 114
<211> LENGTH: 122
<212> TYPE: PRT
<213> ORGANISM: Artificial Sequence
<220> FEATURE:
<223> OTHER INFORMATION: synthetic

<400> SEQUENCE: 114

Glu Val Gln Leu Val Glu Ser Gly Gly Gly Leu Val Gln Pro Gly Gly
 1               5                  10                  15

```
Ser Leu Arg Leu Ser Cys Ala Ala Ser Gly Ile Thr Leu Ser Ser Tyr
         20                  25                  30

Gly Met Ser Trp Val Arg Gln Ala Pro Gly Lys Gly Leu Glu Trp Val
         35                  40                  45

Ala Ser Ile Phe Gly Ser Gly Gly Pro Tyr Tyr Ala Asp Ser Val
 50                  55                  60

Lys Gly Arg Phe Thr Met Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Tyr Ser Gly Ser Tyr Tyr Gly Tyr Phe Asp Tyr Trp
                100                 105                 110

Gly Arg Gly Thr Leu Val Thr Val Ser Ser
        115                 120
```

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115 ggaatcaccct tgagcagcta tggc                                       24

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

Gly Ile Thr Leu Ser Ser Tyr Gly
 1               5

<210> SEQ ID NO 117
<211> LENGTH: 24
<212> TYPE: DNA
<213> ORGANISM: Artificial Sequence
<220> FEATURE:
<223> OTHER INFORMATION: synthetic

<400> SEQUENCE: 117 attttggta gtggtggtgg ccca                                         24

<210> SEQ ID NO 118
<211> LENGTH: 8
<212> TYPE: PRT
<213> ORGANISM: Artificial Sequence
<220> FEATURE:
<223> OTHER INFORMATION: synthetic

<400> SEQUENCE: 118

Ile Phe Gly Ser Gly Gly Gly Pro
 1               5

<210> SEQ ID NO 119
<211> LENGTH: 45
<212> TYPE: DNA
<213> ORGANISM: Artificial Sequence
<220> FEATURE:
<223> OTHER INFORMATION: synthetic

<400> SEQUENCE: 119
gcgaaagatc gatacagtgg gagctactac ggaggttttg actac                45

<210> SEQ ID NO 120
<211> LENGTH: 15
<212> TYPE: PRT
<213> ORGANISM: Artificial Sequence
<220> FEATURE:
<223> OTHER INFORMATION: synthetic

<400> SEQUENCE: 120

Ala Lys Asp Arg Tyr Ser Gly Ser Tyr Tyr Gly Gly Phe Asp Tyr
 1               5                  10                  15

<210> SEQ ID NO 121
<211> LENGTH: 321
<212> TYPE: DNA
<213> ORGANISM: Artificial Sequence
<220> FEATURE:
<223> OTHER INFORMATION: synthetic

<400> SEQUENCE: 121
gacatccaga tgacccagtc tccatcttcc gtgtctgcat ctgtaggaga cagagtcacc    60
atcacttgtc gggcgagtca gggtattacc agctggttag cctggtatca gcagaaacca   120
gggaaagccc ctacactcct gatctatgct gcatccagtt tgcaaactgg ggtcccatca   180
aggttcagcg gcagtggatc tgggacagat ttcactctca ccatcagcag cctgcagcct   240
gaacattttg caacttacta ttgtcaacag gctaacagtt tccctcctac tttcggcgga   300
gggaccaagg tggagatcaa a                                             321

<210> SEQ ID NO 122
<211> LENGTH: 107
<212> TYPE: PRT
<213> ORGANISM: Artificial Sequence
<220> FEATURE:
<223> OTHER INFORMATION: synthetic

<400> SEQUENCE: 122

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Thr Ser Trp
             20                  25                  30

Leu Ala Trp Tyr Gln Gln Lys Pro Gly Lys Ala Pro Thr Leu Leu Ile
         35                  40                  45

Tyr Ala Ala Ser Ser Leu Gln Thr Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu His Phe Ala Thr Tyr Tyr Cys Gln Gln Ala Asn Ser Phe Pro Pro
                 85                  90                  95

Thr Phe Gly Gly Gly Thr Lys Val Glu Ile Lys
            100                 105

<210> SEQ ID NO 123
<211> LENGTH: 18
<212> TYPE: DNA
<213> ORGANISM: Artificial Sequence
<220> FEATURE:
<223> OTHER INFORMATION: synthetic

```
<400> SEQUENCE: 123
cagggtatta ccagctgg                                                    18

<210> SEQ ID NO 124
<211> LENGTH: 6
<212> TYPE: PRT
<213> ORGANISM: Artificial Sequence
<220> FEATURE:
<223> OTHER INFORMATION: synthetic

<400> SEQUENCE: 124

Gln Gly Ile Thr Ser Trp
 1               5

<210> SEQ ID NO 125
<211> LENGTH: 9
<212> TYPE: DNA
<213> ORGANISM: Artificial Sequence
<220> FEATURE:
<223> OTHER INFORMATION: synthetic

<400> SEQUENCE: 125 gctgcatcc                                                               9

<210> SEQ ID NO 126
<211> LENGTH: 3
<212> TYPE: PRT
<213> ORGANISM: Artificial Sequence
<220> FEATURE:
<223> OTHER INFORMATION: synthetic

<400> SEQUENCE: 126

Ala Ala Ser
 1

<210> SEQ ID NO 127
<211> LENGTH: 27
<212> TYPE: DNA
<213> ORGANISM: Artificial Sequence
<220> FEATURE:
<223> OTHER INFORMATION: synthetic

<400> SEQUENCE: 127
caacaggcta acagtttccc tcctact                                          27

<210> SEQ ID NO 128
<211> LENGTH: 9
<212> TYPE: PRT
<213> ORGANISM: Artificial Sequence
<220> FEATURE:
<223> OTHER INFORMATION: synthetic

<400> SEQUENCE: 128

Gln Gln Ala Asn Ser Phe Pro Pro Thr
 1               5

<210> SEQ ID NO 129
<211> LENGTH: 366
<212> TYPE: DNA
<213> ORGANISM: Artificial Sequence
<220> FEATURE:
<223> OTHER INFORMATION: synthetic

<400> SEQUENCE: 129
gaggtgcagc tggtggagtc tgggggaggc ttggtacagc ctggggggtc cctaagactc      60
```

```
tcctgtgcag cctctggatt cacctttagc agttatgcct tgacctgggt ccgccaggct    120
ccagggaagg ggctggagtg gtctctttt attagtggta gtggtggtag gccattctac     180
gcagactccg tgaagggccg gttcaccatc tccagagaca attccaagaa catgctgtat    240
ctgcaaatga acagcctgag agccgaggac acggccatat attactgtgc gaagtccctg    300
tataccacca gctggtacgg ggggttcgac tcctggggcc agggaaccct ggtcaccgtc    360
tcctca                                                               366
```

<210> SEQ ID NO 130
<211> LENGTH: 122
<212> TYPE: PRT
<213> ORGANISM: Artificial Sequence
<220> FEATURE:
<223> OTHER INFORMATION: synthetic
<400> SEQUENCE: 130

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Leu Thr Trp Val Arg Gln Ala Pro Gly Lys Gly Leu Glu Trp Val
        35                  40                  45

Ser Phe Ile Ser Gly Ser Gly Gly Arg Pro Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Ile Tyr Tyr Cys
                85                  90                  95

Ala Lys Ser Leu Tyr Thr Thr Ser Trp Tyr Gly Gly Phe Asp Ser Trp
            100                 105                 110

Gly Gln Gly Thr Leu Val Thr Val Ser Ser
        115                 120
```

<210> SEQ ID NO 131
<211> LENGTH: 24
<212> TYPE: DNA
<213> ORGANISM: Artificial Sequence
<220> FEATURE:
<223> OTHER INFORMATION: synthetic
<400> SEQUENCE: 131

```
ggattcacct ttagcagtta tgcc                                            24
```

<210> SEQ ID NO 132
<211> LENGTH: 8
<212> TYPE: PRT
<213> ORGANISM: Artificial Sequence
<220> FEATURE:
<223> OTHER INFORMATION: synthetic
<400> SEQUENCE: 132

```
Gly Phe Thr Phe Ser Ser Tyr Ala
 1               5
```

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133
attagtggta gtggtggtag gcca                                              24

<210> SEQ ID NO 134
<211> LENGTH: 8
<212> TYPE: PRT
<213> ORGANISM: Artificial Sequence
<220> FEATURE:
<223> OTHER INFORMATION: synthetic

<400> SEQUENCE: 134

Ile Ser Gly Ser Gly Gly Arg Pro
1               5

<210> SEQ ID NO 135
<211> LENGTH: 45
<212> TYPE: DNA
<213> ORGANISM: Artificial Sequence
<220> FEATURE:
<223> OTHER INFORMATION: synthetic

<400> SEQUENCE: 135
gcgaagtccc tgtataccac cagctggtac gggggttcg actcc                       45

<210> SEQ ID NO 136
<211> LENGTH: 15
<212> TYPE: PRT
<213> ORGANISM: Artificial Sequence
<220> FEATURE:
<223> OTHER INFORMATION: synthetic

<400> SEQUENCE: 136

Ala Lys Ser Leu Tyr Thr Thr Ser Trp Tyr Gly Gly Phe Asp Ser
1               5                   10                  15

<210> SEQ ID NO 137
<211> LENGTH: 321
<212> TYPE: DNA
<213> ORGANISM: Artificial Sequence
<220> FEATURE:
<223> OTHER INFORMATION: synthetic

<400> SEQUENCE: 137
gacatccaga tgacccagtc tccatcttcc gtgtctgcat ctgtaggaga cagagtcacc       60
atcacttgtc gggcgagtca gggtgtcgtc agctggttag cctggtatca gcagaaacca      120
gggaaagccc ctaagctcct gatctatgct gcatccagtt tgcaaagtgg ggtcccatca      180
aggttcagcg gcagtggatc tgggacagat ttcactctca ccatcagcag cctgcagcct      240
gaagattttg caacttatta ttgtcaacag tctaacagtt tccctttcac tctcggccct      300
gggaccaaag tggatatcaa a                                                321

<210> SEQ ID NO 138
<211> LENGTH: 107
<212> TYPE: PRT
<213> ORGANISM: Artificial Sequence
<220> FEATURE:
<223> OTHER INFORMATION: synthetic

<400> SEQUENCE: 138

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Val Ser Trp
            20                  25                  30

```
Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Ser Phe Pro Phe
                 85                  90                  95

Thr Leu Gly Pro Gly Thr Lys Val Asp Ile Lys
                100                 105

<210> SEQ ID NO 139
<211> LENGTH: 18
<212> TYPE: DNA
<213> ORGANISM: Artificial Sequence
<220> FEATURE:
<223> OTHER INFORMATION: synthetic

<400> SEQUENCE: 139
cagggtgtcg tcagctgg                                                    18

<210> SEQ ID NO 140
<211> LENGTH: 6
<212> TYPE: PRT
<213> ORGANISM: Artificial Sequence
<220> FEATURE:
<223> OTHER INFORMATION: synthetic

<400> SEQUENCE: 140

Gln Gly Val Val Ser Trp
 1               5

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141 gctgcatcc                                                               9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

Ala Ala Ser
 1

<210> SEQ ID NO 143
<211> LENGTH: 24
<212> TYPE: DNA
<213> ORGANISM: Artificial Sequence
<220> FEATURE:
<223> OTHER INFORMATION: synthetic

<400> SEQUENCE: 143
caacagtcta acagtttccc tttc                                             24
```

<210> SEQ ID NO 144
<211> LENGTH: 8
<212> TYPE: PRT
<213> ORGANISM: Artificial Sequence
<220> FEATURE:
<223> OTHER INFORMATION: synthetic

<400> SEQUENCE: 144

Gln Gln Ser Asn Ser Phe Pro Phe
1               5

<210> SEQ ID NO 145
<211> LENGTH: 366
<212> TYPE: DNA
<213> ORGANISM: Artificial Sequence
<220> FEATURE:
<223> OTHER INFORMATION: synthetic

<400> SEQUENCE: 145
caggtgcagc tggtgcagtc tggggctgaa gtgaagaagc ctggggcctc agtgaaggtc     60
tcctgcaagg cttctggata caccttcacc ggccactata tgtactggat gcgacaggcc    120
cctggacaag gcttgagtg gatgggatgg atcaaccct a acagtggtgg cacaaactat    180
gcacagaagt tccaggacag ggtcaccatg accaggaca cgtccatcag cacagcctac    240
atggagctga gcaggctgag atctgacgac acggccgtgt attactgtgc gagagggaga    300
tatggcagta gctggtacgg ggggtttgag tactggggcc agggaaccct ggtcaccgtc    360
tcctca                                                               366

<210> SEQ ID NO 146
<211> LENGTH: 122
<212> TYPE: PRT
<213> ORGANISM: Artificial Sequence
<220> FEATURE:
<223> OTHER INFORMATION: synthetic

<400> SEQUENCE: 146

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly His
                20                  25                  30

Tyr Met Tyr Trp Met Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Arg Tyr Gly Ser Ser Trp Tyr Gly Gly Phe Glu Tyr Trp
            100                 105                 110

Gly Gln Gly Thr Leu Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147
ggatacacct tcaccggcca ctat                                              24

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

Gly Tyr Thr Phe Thr Gly His Tyr
 1               5

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
atcaacccta acagtggtgg caca                                              24

<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

Ile Asn Pro Asn Ser Gly Gly Thr
 1               5

<210> SEQ ID NO 151
<211> LENGTH: 45
<212> TYPE: DNA
<213> ORGANISM: Artificial Sequence
<220> FEATURE:
<223> OTHER INFORMATION: synthetic

<400> SEQUENCE: 151
gcgagaggga gatatggcag tagctggtac gggggtttg agtac                        45

<210> SEQ ID NO 152
<211> LENGTH: 15
<212> TYPE: PRT
<213> ORGANISM: Artificial Sequence
<220> FEATURE:
<223> OTHER INFORMATION: synthetic

<400> SEQUENCE: 152

Ala Arg Gly Arg Tyr Gly Ser Ser Trp Tyr Gly Gly Phe Glu Tyr
 1               5                  10                  15

<210> SEQ ID NO 153
<211> LENGTH: 321
<212> TYPE: DNA
<213> ORGANISM: Artificial Sequence
<220> FEATURE:
<223> OTHER INFORMATION: synthetic

<400> SEQUENCE: 153
gacatccaga tgacccagtc tccatcttcc gtgtctgcat ctgttggaga cagagtcacc       60
atcacttgtc gggcgagtca gggtattacc agctggttag cctggtatca gcagaaacca      120

```
gggaaagccc ctaacctcct gatctatgct gcagccagtt tacaaagtgg ggtcccatca      180
aggttcagcg gcagtggatc tgggacggat ttcactctca ccatcagcag cctgcagcct      240
gaagacttta caacttacta ttgtcaacag gcttacagtc tccctctcac tttcggcgga      300
gggaccaagg tggagatcaa a                                                321
```

```
<210> SEQ ID NO 154
<211> LENGTH: 107
<212> TYPE: PRT
<213> ORGANISM: Artificial Sequence
<220> FEATURE:
<223> OTHER INFORMATION: synthetic

<400> SEQUENCE: 154

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Thr Ser Trp
            20                  25                  30

Leu Ala Trp Tyr Gln Gln Lys Pro Gly Lys Ala Pro Asn Leu Leu Ile
        35                  40                  45

Tyr Ala Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Ala Tyr Ser Leu Pro Leu
                85                  90                  95

Thr Phe Gly Gly Gly Thr Lys Val Glu Ile Lys
            100                 105
```

```
<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155
cagggtatta ccagctgg                                                     18
```

```
<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

Gln Gly Ile Thr Ser Trp
 1               5
```

```
<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 gctgcagcc                                                               9
```

```
<210> SEQ ID NO 158
```

```
<211> LENGTH: 3
<212> TYPE: PRT
<213> ORGANISM: Artificial Sequence
<220> FEATURE:
<223> OTHER INFORMATION: synthetic

<400> SEQUENCE: 158

Ala Ala Ala
 1

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159
caacaggctt acagtctccc tctcact                                        27

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Gln Gln Ala Tyr Ser Leu Pro Leu Thr
 1               5

<210> SEQ ID NO 161
<211> LENGTH: 366
<212> TYPE: DNA
<213> ORGANISM: Artificial Sequence
<220> FEATURE:
<223> OTHER INFORMATION: synthetic

<400> SEQUENCE: 161
caggtgcagc tggtggagtc tgggggaggc gtggtccagc ctggagggtc cctgagactc     60
tcctgtgcag cctctggatt caccttcagt agctatggct tgcactgggt ccgccagtct    120
ccaggcaagg ggctggaatg ggtggcactt atatcatatg acggaagtaa taaatactat    180
gcagactccg tgaagggccg attcaccatc tccagagaca attccaagaa cacgctgtat    240
ctgcaaatga acagcctgag acctgaggac acggctggat atttctgtgc gaaatcccta    300
tatacaacca gctggtacgg gggctttgac tattggggcc agggaaccct ggtcaccgtc    360
tcctca                                                              366

<210> SEQ ID NO 162
<211> LENGTH: 122
<212> TYPE: PRT
<213> ORGANISM: Artificial Sequence
<220> FEATURE:
<223> OTHER INFORMATION: synthetic

<400> SEQUENCE: 162

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Ser Tyr
                20                  25                  30

Gly Leu His Trp Val Arg Gln Ser Pro Gly Lys Gly Leu Glu Trp Val
            35                  40                  45
```

Ala Leu Ile Ser Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Gly Tyr Phe Cys
                 85                  90                  95

Ala Lys Ser Leu Tyr Thr Thr Ser Trp Tyr Gly Gly Phe Asp Tyr Trp
            100                 105                 110

Gly Gln Gly Thr Leu Val Thr Val Ser Ser
            115                 120

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163
ggattcacct tcagtagcta tggc                                    24

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Gly Phe Thr Phe Ser Ser Tyr Gly
 1               5

<210> SEQ ID NO 165
<211> LENGTH: 24
<212> TYPE: DNA
<213> ORGANISM: Artificial Sequence
<220> FEATURE:
<223> OTHER INFORMATION: synthetic

<400> SEQUENCE: 165
atatcatatg acggaagtaa taaa                                    24

<210> SEQ ID NO 166
<211> LENGTH: 8
<212> TYPE: PRT
<213> ORGANISM: Artificial Sequence
<220> FEATURE:
<223> OTHER INFORMATION: synthetic

<400> SEQUENCE: 166

Ile Ser Tyr Asp Gly Ser Asn Lys
 1               5

<210> SEQ ID NO 167
<211> LENGTH: 45
<212> TYPE: DNA
<213> ORGANISM: Artificial Sequence
<220> FEATURE:
<223> OTHER INFORMATION: synthetic

<400> SEQUENCE: 167
gcgaaatccc tatatacaac cagctggtac gggggctttg actat              45

<210> SEQ ID NO 168

<211> LENGTH: 15
<212> TYPE: PRT
<213> ORGANISM: Artificial Sequence
<220> FEATURE:
<223> OTHER INFORMATION: synthetic

<400> SEQUENCE: 168

Ala Lys Ser Leu Tyr Thr Thr Ser Trp Tyr Gly Gly Phe Asp Tyr
1               5                   10                  15

<210> SEQ ID NO 169
<211> LENGTH: 321
<212> TYPE: DNA
<213> ORGANISM: Artificial Sequence
<220> FEATURE:
<223> OTHER INFORMATION: synthetic

<400> SEQUENCE: 169
gacatccaga tgacccagtc tccatcttcc gtgtctgcat ctgtaggaga cagagtcacc    60
atcacttgtc gggcgagtca gggtattaga agctggttag cctggtatca gcaaaaacca   120
gggaaagccc ctaacctcct gatctatgct gcgtccagtt tgcaaagtgg ggtcccatca   180
aggttcagcg gcagtggatc tgggacagat ttcactctca ccatcagcag cctgcagcct   240
gaagattttg caacttacta ttgtcaacag gctaacagtt tccctcccac tttcggccct   300
gggaccaaag tggatatcaa a                                             321

<210> SEQ ID NO 170
<211> LENGTH: 107
<212> TYPE: PRT
<213> ORGANISM: Artificial Sequence
<220> FEATURE:
<223> OTHER INFORMATION: synthetic

<400> SEQUENCE: 170

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Ser Trp
                20                  25                  30

Leu Ala Trp Tyr Gln Gln Lys Pro Gly Lys Ala Pro Asn Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Pro Gly Thr Lys Val Asp Ile Lys
            100                 105

<210> SEQ ID NO 171
<211> LENGTH: 18
<212> TYPE: DNA
<213> ORGANISM: Artificial Sequence
<220> FEATURE:
<223> OTHER INFORMATION: synthetic

<400> SEQUENCE: 171
cagggtatta gaagctgg                                                  18

<210> SEQ ID NO 172
<211> LENGTH: 6

<212> TYPE: PRT
<213> ORGANISM: Artificial Sequence
<220> FEATURE:
<223> OTHER INFORMATION: synthetic

<400> SEQUENCE: 172

Gln Gly Ile Arg Ser Trp
 1               5

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173 gctgcgtcc                                                                  9

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

Ala Ala Ser
 1

<210> SEQ ID NO 175
<211> LENGTH: 27
<212> TYPE: DNA
<213> ORGANISM: Artificial Sequence
<220> FEATURE:
<223> OTHER INFORMATION: synthetic

<400> SEQUENCE: 175
caacaggcta acagtttccc tcccact                                             27

<210> SEQ ID NO 176
<211> LENGTH: 9
<212> TYPE: PRT
<213> ORGANISM: Artificial Sequence
<220> FEATURE:
<223> OTHER INFORMATION: synthetic

<400> SEQUENCE: 176

Gln Gln Ala Asn Ser Phe Pro Pro Thr
 1               5

<210> SEQ ID NO 177
<211> LENGTH: 366
<212> TYPE: DNA
<213> ORGANISM: Artificial Sequence
<220> FEATURE:
<223> OTHER INFORMATION: synthetic

<400> SEQUENCE: 177
gaggtgcagc tggtggagtc tgggggaggc ttggtacagc ctggggggtc cctgagactc        60
tcctgtgcag cctctgggtt caccttcagc aactatgcca tgacctgggt ccgccaggct       120
ccagggaagg gctggagtg gtctcaact atcagtggca gtggtgataa cacatactac         180
gcagactccg tgcagggccg gttcaccatc tccagaggcc attccaagaa cacgctgtat       240
ctgcaaatga acagcctgag agccgaggac acggccgtat attactgtgc gaaacctacg       300
tatagcagaa gctggtacgg tgcttttgat ttctggggcc aagggacaat ggtcaccgtc    360
tcttca    366

<210> SEQ ID NO 178
<211> LENGTH: 122
<212> TYPE: PRT
<213> ORGANISM: Artificial Sequence
<220> FEATURE:
<223> OTHER INFORMATION: synthetic

<400> SEQUENCE: 178

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Lys Gly Leu Glu Trp Val
        35                  40                  45

Ser Thr Ile Ser Gly Ser Gly Asp Asn Thr Tyr Tyr Ala Asp Ser Val
    50                  55                  60

Gln Gly Arg Phe Thr Ile Ser Arg Gly His Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Thr Tyr Ser Arg Ser Trp Tyr Gly Ala Phe Asp Phe Trp
            100                 105                 110

Gly Gln Gly Thr Met Val Thr Val Ser Ser
        115                 120

<210> SEQ ID NO 179
<211> LENGTH: 24
<212> TYPE: DNA
<213> ORGANISM: Artificial Sequence
<220> FEATURE:
<223> OTHER INFORMATION: synthetic

<400> SEQUENCE: 179
gggttcacct tcagcaacta tgcc    24

<210> SEQ ID NO 180
<211> LENGTH: 8
<212> TYPE: PRT
<213> ORGANISM: Artificial Sequence
<220> FEATURE:
<223> OTHER INFORMATION: synthetic

<400> SEQUENCE: 180

Gly Phe Thr Phe Ser Asn Tyr Ala
1               5

<210> SEQ ID NO 181
<211> LENGTH: 24
<212> TYPE: DNA
<213> ORGANISM: Artificial Sequence
<220> FEATURE:
<223> OTHER INFORMATION: synthetic

<400> SEQUENCE: 181
atcagtggca gtggtgataa caca    24

<210> SEQ ID NO 182
<211> LENGTH: 8

```
<212> TYPE: PRT
<213> ORGANISM: Artificial Sequence
<220> FEATURE:
<223> OTHER INFORMATION: synthetic

<400> SEQUENCE: 182

Ile Ser Gly Ser Gly Asp Asn Thr
 1               5

<210> SEQ ID NO 183
<211> LENGTH: 45
<212> TYPE: DNA
<213> ORGANISM: Artificial Sequence
<220> FEATURE:
<223> OTHER INFORMATION: synthetic

<400> SEQUENCE: 183
gcgaaaccta cgtatagcag aagctggtac ggtgcttttg atttc            45

<210> SEQ ID NO 184
<211> LENGTH: 15
<212> TYPE: PRT
<213> ORGANISM: Artificial Sequence
<220> FEATURE:
<223> OTHER INFORMATION: synthetic

<400> SEQUENCE: 184

Ala Lys Pro Thr Tyr Ser Arg Ser Trp Tyr Gly Ala Phe Asp Phe
 1               5                  10                  15

<210> SEQ ID NO 185
<211> LENGTH: 321
<212> TYPE: DNA
<213> ORGANISM: Artificial Sequence
<220> FEATURE:
<223> OTHER INFORMATION: synthetic

<400> SEQUENCE: 185
gacatccaga tgacccagtc tccatcctcc gtgtctgcat ctgtaggaga cagagtcacc    60
atcacttgtc gggcgagtca gggtattagc agctggttag cctggtatca gcagaaaccg   120
gggaaagccc ctcaactcct gatctatgct gcatccagat tgcaaagtgg ggtcccatca   180
aggttctggg gcagtggatc tgggacagat tcactctca ccatcagcag cctgcagcct   240
gaagattttg caacttacta ttgtcaacag gctaacaatt tcccattcac tttcggccct   300
gggaccaaag tggatatcaa a                                              321

<210> SEQ ID NO 186
<211> LENGTH: 107
<212> TYPE: PRT
<213> ORGANISM: Artificial Sequence
<220> FEATURE:
<223> OTHER INFORMATION: synthetic

<400> SEQUENCE: 186

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Gln Leu Leu Ile
         35                  40                  45

Tyr Ala Ala Ser Arg Leu Gln Ser Gly Val Pro Ser Arg Phe Trp Gly
     50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Phe
            85                  90                  95

Thr Phe Gly Pro Gly Thr Lys Val Asp Ile Lys
        100                 105

<210> SEQ ID NO 187
<211> LENGTH: 18
<212> TYPE: DNA
<213> ORGANISM: Artificial Sequence
<220> FEATURE:
<223> OTHER INFORMATION: synthetic

<400> SEQUENCE: 187
cagggtatta gcagctgg                                                 18

<210> SEQ ID NO 188
<211> LENGTH: 6
<212> TYPE: PRT
<213> ORGANISM: Artificial Sequence
<220> FEATURE:
<223> OTHER INFORMATION: synthetic

<400> SEQUENCE: 188

Gln Gly Ile Ser Ser Trp
1               5

<210> SEQ ID NO 189
<211> LENGTH: 9
<212> TYPE: DNA
<213> ORGANISM: Artificial Sequence
<220> FEATURE:
<223> OTHER INFORMATION: synthetic

<400> SEQUENCE: 189 gctgcatcc                                                            9

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

Ala Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: synthetic

<400> SEQUENCE: 191
caacaggcta acaatttccc attcact                                       27

<210> SEQ ID NO 192
<211> LENGTH: 9
<212> TYPE: PRT
<213> ORGANISM: Artificial Sequence
<220> FEATURE:
<223> OTHER INFORMATION: synthetic

<400> SEQUENCE: 192

Gln Gln Ala Asn Asn Phe Pro Phe Thr
 1               5

<210> SEQ ID NO 193
<211> LENGTH: 366
<212> TYPE: DNA
<213> ORGANISM: Artificial Sequence
<220> FEATURE:
<223> OTHER INFORMATION: synthetic

<400> SEQUENCE: 193

```
caggttcagc tggtgcagtc tggagctgag gtgaagaagc ctggggcctc agtgaaggtc      60
tcctgcaagg cttctggtta cacctttacc agttatggta tcagctgggt gcgacaggcc     120
cctggacaag gccttgagtg gatgggatgg atccgcgctt acaatggtta cacaaactat     180
gcacagaagt tcagggcag agtcaccatg accacagaca catccacgaa caccgcctac      240
atggagctga ggaccctgaa ttctgacgat acggccgttt attactgtgc gagagatcga     300
tatagtggga gcttccacgg taactttgac tactggggcc agggaaccct ggtcaccgtc     360
tcctca                                                                366
```

<210> SEQ ID NO 194
<211> LENGTH: 122
<212> TYPE: PRT
<213> ORGANISM: Artificial Sequence
<220> FEATURE:
<223> OTHER INFORMATION: synthetic

<400> SEQUENCE: 194

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Arg Ala Tyr Asn Gly Tyr Thr Asn Tyr Ala Gln Lys Phe
        50                  55                  60

Gln Gly Arg Val Thr Met Thr Thr Asp Thr Ser Thr Asn Thr Ala Tyr
65                  70                  75                  80

Met Glu Leu Arg Thr Leu Asn Ser Asp Asp Thr Ala Val Tyr Tyr Cys
                85                  90                  95

Ala Arg Asp Arg Tyr Ser Gly Ser Phe His Gly Asn Phe Asp Tyr Trp
            100                 105                 110

Gly Gln Gly Thr Leu Val Thr Val Ser Ser
        115                 120

<210> SEQ ID NO 195
<211> LENGTH: 24
<212> TYPE: DNA
<213> ORGANISM: Artificial Sequence
<220> FEATURE:
<223> OTHER INFORMATION: synthetic

<400> SEQUENCE: 195

```
ggttacacct ttaccagtta tggt                                             24
```

<210> SEQ ID NO 196
<211> LENGTH: 8
<212> TYPE: PRT

```
<213> ORGANISM: Artificial Sequence
<220> FEATURE:
<223> OTHER INFORMATION: synthetic

<400> SEQUENCE: 196

Gly Tyr Thr Phe Thr Ser Tyr Gly
 1               5

<210> SEQ ID NO 197
<211> LENGTH: 24
<212> TYPE: DNA
<213> ORGANISM: Artificial Sequence
<220> FEATURE:
<223> OTHER INFORMATION: synthetic

<400> SEQUENCE: 197
atccgcgctt acaatggtta caca                                           24

<210> SEQ ID NO 198
<211> LENGTH: 8
<212> TYPE: PRT
<213> ORGANISM: Artificial Sequence
<220> FEATURE:
<223> OTHER INFORMATION: synthetic

<400> SEQUENCE: 198

Ile Arg Ala Tyr Asn Gly Tyr Thr
 1               5

<210> SEQ ID NO 199
<211> LENGTH: 45
<212> TYPE: DNA
<213> ORGANISM: Artificial Sequence
<220> FEATURE:
<223> OTHER INFORMATION: synthetic

<400> SEQUENCE: 199
gcgagagatc gatatagtgg gagcttccac ggtaactttg actac                    45

<210> SEQ ID NO 200
<211> LENGTH: 15
<212> TYPE: PRT
<213> ORGANISM: Artificial Sequence
<220> FEATURE:
<223> OTHER INFORMATION: synthetic

<400> SEQUENCE: 200

Ala Arg Asp Arg Tyr Ser Gly Ser Phe His Gly Asn Phe Asp Tyr
 1               5                  10                  15

<210> SEQ ID NO 201
<211> LENGTH: 321
<212> TYPE: DNA
<213> ORGANISM: Artificial Sequence
<220> FEATURE:
<223> OTHER INFORMATION: synthetic

<400> SEQUENCE: 201
gacatccaga tgacccagtc tccatcttcc gtgtctgcgt ctgtaggaga cagagtgacc    60
atcacttgtc gggcgagtca gggtattttc agctggttag cctggtatca gcagaaacca   120
gggaaagccc ctaaggtcct aatctatgct gcatccaatt tggaaagtgg ggtcccatca   180
aggttcagcg gcagtggatc tgggacagat tcactctca ccatcagcag cctgcagcct    240
gaagattttg caacttacta ttgtcaacag gctaacagtt taccgctcac tttcggcgga   300
```
gggaccaagg tggagatcaa a                                              321

<210> SEQ ID NO 202
<211> LENGTH: 107
<212> TYPE: PRT
<213> ORGANISM: Artificial Sequence
<220> FEATURE:
<223> OTHER INFORMATION: synthetic

<400> SEQUENCE: 202

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Phe Ser Trp
            20                  25                  30

Leu Ala Trp Tyr Gln Gln Lys Pro Gly Lys Ala Pro Lys Val Leu Ile
        35                  40                  45

Tyr Ala Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Leu Pro Leu
                85                  90                  95

Thr Phe Gly Gly Gly Thr Lys Val Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: synthetic

<400> SEQUENCE: 203
cagggtattt tcagctgg                                                   18

<210> SEQ ID NO 204
<211> LENGTH: 6
<212> TYPE: PRT
<213> ORGANISM: Artificial Sequence
<220> FEATURE:
<223> OTHER INFORMATION: synthetic

<400> SEQUENCE: 204

Gln Gly Ile Phe Ser Trp
1               5

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 gctgcatcc                                                              9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

Ala Ala Ser
 1

<210> SEQ ID NO 207
<211> LENGTH: 27
<212> TYPE: DNA
<213> ORGANISM: Artificial Sequence
<220> FEATURE:
<223> OTHER INFORMATION: synthetic

<400> SEQUENCE: 207
caacaggcta acagtttacc gctcact                                        27

<210> SEQ ID NO 208
<211> LENGTH: 9
<212> TYPE: PRT
<213> ORGANISM: Artificial Sequence
<220> FEATURE:
<223> OTHER INFORMATION: synthetic

<400> SEQUENCE: 208

Gln Gln Ala Asn Ser Leu Pro Leu Thr
 1               5

<210> SEQ ID NO 209
<211> LENGTH: 366
<212> TYPE: DNA
<213> ORGANISM: Artificial Sequence
<220> FEATURE:
<223> OTHER INFORMATION: synthetic

<400> SEQUENCE: 209
gaggtgcagc tggtggagtc tgggggaggc ttggtccagc ctggggggtc cctgagactc      60
tcctgtgcag cctctggatt caccttcagt acctattcta tgcactgggt ccgccaggct     120
ccagggaagg gactggaata tgtttcaact attaataata atggggatac acatatattat    180 gcagactctg tgaagggcag attcaccatc tccagagaca attccaagaa cacgctgtat     240
cttcaactgg gcagcctgag acctgaggac atggctgtgt attactgtgc gagacagacg     300
tataccagca gctggtacgg ggggttcgac tcctggggcc agggaaccct ggtcaccgtc     360
tcctca                                                               366

<210> SEQ ID NO 210
<211> LENGTH: 122
<212> TYPE: PRT
<213> ORGANISM: Artificial Sequence
<220> FEATURE:
<223> OTHER INFORMATION: synthetic

<400> SEQUENCE: 210

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Thr Ile Asn Asn Asn Gly Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Gly Ser Leu Arg Pro Glu Asp Met Ala Val Tyr Tyr Cys

```
                    85                  90                  95
Ala Arg Gln Thr Tyr Thr Ser Ser Trp Tyr Gly Gly Phe Asp Ser Trp
            100                 105                 110

Gly Gln Gly Thr Leu Val Thr Val Ser Ser
        115                 120
```

<210> SEQ ID NO 211
<211> LENGTH: 24
<212> TYPE: DNA
<213> ORGANISM: Artificial Sequence
<220> FEATURE:
<223> OTHER INFORMATION: synthetic

<400> SEQUENCE: 211
ggattcacct tcagtaccta ttct                                            24

<210> SEQ ID NO 212
<211> LENGTH: 8
<212> TYPE: PRT
<213> ORGANISM: Artificial Sequence
<220> FEATURE:
<223> OTHER INFORMATION: synthetic

<400> SEQUENCE: 212

```
Gly Phe Thr Phe Ser Thr Tyr Ser
1               5
```

<210> SEQ ID NO 213
<211> LENGTH: 24
<212> TYPE: DNA
<213> ORGANISM: Artificial Sequence
<220> FEATURE:
<223> OTHER INFORMATION: synthetic

<400> SEQUENCE: 213
attaataata atggggatac caca                                            24

<210> SEQ ID NO 214
<211> LENGTH: 8
<212> TYPE: PRT
<213> ORGANISM: Artificial Sequence
<220> FEATURE:
<223> OTHER INFORMATION: synthetic

<400> SEQUENCE: 214

```
Ile Asn Asn Asn Gly Asp Thr Thr
1               5
```

<210> SEQ ID NO 215
<211> LENGTH: 45
<212> TYPE: DNA
<213> ORGANISM: Artificial Sequence
<220> FEATURE:
<223> OTHER INFORMATION: synthetic

<400> SEQUENCE: 215
gcgagacaga cgtataccag cagctggtac gggggttcg actcc                      45

<210> SEQ ID NO 216
<211> LENGTH: 15
<212> TYPE: PRT
<213> ORGANISM: Artificial Sequence
<220> FEATURE:
<223> OTHER INFORMATION: synthetic

<400> SEQUENCE: 216

Ala Arg Gln Thr Tyr Thr Ser Ser Trp Tyr Gly Gly Phe Asp Ser
1               5                   10                  15

<210> SEQ ID NO 217
<211> LENGTH: 321
<212> TYPE: DNA
<213> ORGANISM: Artificial Sequence
<220> FEATURE:
<223> OTHER INFORMATION: synthetic

<400> SEQUENCE: 217

```
gacatccaga tgacccagtc tccatcttcc gtgtctgcat ctgtaggcga cagagtcacc    60
atcacttgtc gggcgagtca gggtattacc agctggttag cctggtatca gcagaaacca   120
gggaaagccc ctaaactcct gatctatgct gcatccaatt tgcaaagtgg ggtcccatca   180
aggttcagcg gcagtggatc tgggacagat ttcactctca ccatcaccag cctgcagcct   240
gaggattttg caacttacta ttgtcaacag gctaacagtc tcccattcac tttcggccct   300
gggaccaaag tggatatcaa a                                             321
```

<210> SEQ ID NO 218
<211> LENGTH: 107
<212> TYPE: PRT
<213> ORGANISM: Artificial Sequence
<220> FEATURE:
<223> OTHER INFORMATION: synthetic

<400> SEQUENCE: 218

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Thr Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ala Asn Ser Leu Pro Phe
                85                  90                  95

Thr Phe Gly Pro Gly Thr Lys Val Asp Ile Lys
            100                 105

<210> SEQ ID NO 219
<211> LENGTH: 18
<212> TYPE: DNA
<213> ORGANISM: Artificial Sequence
<220> FEATURE:
<223> OTHER INFORMATION: synthetic

<400> SEQUENCE: 219

```
cagggtatta ccagctgg                                                  18
```

<210> SEQ ID NO 220
<211> LENGTH: 6
<212> TYPE: PRT
<213> ORGANISM: Artificial Sequence
<220> FEATURE:
<223> OTHER INFORMATION: synthetic

<400> SEQUENCE: 220

Gln Gly Ile Thr Ser Trp
 1               5

<210> SEQ ID NO 221
<211> LENGTH: 9
<212> TYPE: DNA
<213> ORGANISM: Artificial Sequence
<220> FEATURE:
<223> OTHER INFORMATION: synthetic

<400> SEQUENCE: 221 gctgcatcc                                                                9

<210> SEQ ID NO 222
<211> LENGTH: 3
<212> TYPE: PRT
<213> ORGANISM: Artificial Sequence
<220> FEATURE:
<223> OTHER INFORMATION: synthetic

<400> SEQUENCE: 222

Ala Ala Ser
 1

<210> SEQ ID NO 223
<211> LENGTH: 27
<212> TYPE: DNA
<213> ORGANISM: Artificial Sequence
<220> FEATURE:
<223> OTHER INFORMATION: synthetic

<400> SEQUENCE: 223
caacaggcta acagtctccc attcact                                           27

<210> SEQ ID NO 224
<211> LENGTH: 9
<212> TYPE: PRT
<213> ORGANISM: Artificial Sequence
<220> FEATURE:
<223> OTHER INFORMATION: synthetic

<400> SEQUENCE: 224

Gln Gln Ala Asn Ser Leu Pro Phe Thr
 1               5

<210> SEQ ID NO 225
<211> LENGTH: 366
<212> TYPE: DNA
<213> ORGANISM: Artificial Sequence
<220> FEATURE:
<223> OTHER INFORMATION: synthetic

<400> SEQUENCE: 225
gaggtgcagc tggtggagtc tgggggaggc ttggtacagc ctgggggtc cctgagactc        60 tcctgtgcag cctctggatt caccttagc agctatgcca tgagctgggt ccgccaggct       120
ccagggaagg ggctggagtg ggtctcagct attagtggta gtggtggcag cacatactac      180
gcagactccg tgaagggccg gttcaccatc tccagagaca attccaagaa ctcgctgtat      240
ctgcaattga acagcctgag agccgaggac acggccgtat attactgtgc gaagacgctg      300
tatactacca gctggtacgg gggcttccag cactgggggcc agggcaccct ggtcactgtc      360
tcctca                                                                 366

<210> SEQ ID NO 226

-continued

```
<211> LENGTH: 122
<212> TYPE: PRT
<213> ORGANISM: Artificial Sequence
<220> FEATURE:
<223> OTHER INFORMATION: synthetic

<400> SEQUENCE: 226
```

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Ser Leu Tyr
 65                  70                  75                  80

Leu Gln Leu Asn Ser Leu Arg Ala Glu Asp Thr Ala Val Tyr Tyr Cys
                 85                  90                  95

Ala Lys Thr Leu Tyr Thr Thr Ser Trp Tyr Gly Gly Phe Gln His Trp
            100                 105                 110

Gly Gln Gly Thr Leu Val Thr Val Ser Ser
        115                 120

```
<210> SEQ ID NO 227
<211> LENGTH: 24
<212> TYPE: DNA
<213> ORGANISM: Artificial Sequence
<220> FEATURE:
<223> OTHER INFORMATION: synthetic

<400> SEQUENCE: 227
ggattcaccc ttagcagcta tgcc                                          24

<210> SEQ ID NO 228
<211> LENGTH: 8
<212> TYPE: PRT
<213> ORGANISM: Artificial Sequence
<220> FEATURE:
<223> OTHER INFORMATION: synthetic

<400> SEQUENCE: 228
```

Gly Phe Thr Leu Ser Ser Tyr Ala
 1               5

```
<210> SEQ ID NO 229
<211> LENGTH: 24
<212> TYPE: DNA
<213> ORGANISM: Artificial Sequence
<220> FEATURE:
<223> OTHER INFORMATION: synthetic

<400> SEQUENCE: 229
attagtggta gtggtggcag caca                                          24

<210> SEQ ID NO 230
<211> LENGTH: 8
<212> TYPE: PRT
<213> ORGANISM: Artificial Sequence
<220> FEATURE:
<223> OTHER INFORMATION: synthetic

<400> SEQUENCE: 230
```

```
Ile Ser Gly Ser Gly Gly Ser Thr
 1               5
```

<210> SEQ ID NO 231
<211> LENGTH: 45
<212> TYPE: DNA
<213> ORGANISM: Artificial Sequence
<220> FEATURE:
<223> OTHER INFORMATION: synthetic

<400> SEQUENCE: 231

```
gcgaagacgc tgtatactac cagctggtac gggggcttcc agcac            45
```

<210> SEQ ID NO 232
<211> LENGTH: 15
<212> TYPE: PRT
<213> ORGANISM: Artificial Sequence
<220> FEATURE:
<223> OTHER INFORMATION: synthetic

<400> SEQUENCE: 232

```
Ala Lys Thr Leu Tyr Thr Thr Ser Trp Tyr Gly Gly Phe Gln His
 1               5                  10                  15
```

<210> SEQ ID NO 233
<211> LENGTH: 321
<212> TYPE: DNA
<213> ORGANISM: Artificial Sequence
<220> FEATURE:
<223> OTHER INFORMATION: synthetic

<400> SEQUENCE: 233

```
gacatccaga tgacccagtc tccatcttcc gtgtctgcat ctataggaga cagagtcacc    60
atcacttgtc gggcgagtca gggaatcagc agttggttag cctggtatca gcagaaacca   120
gggaaagtcc ctaagctcct gatctatgct gcgtcctctt tgcaaagtgg gttcccatca   180
aggttcagcg gcagtggatc tgggacagat ttcactctca ccatcagtag cctgcagccc   240
gaagattttg caacttacta ttgtcaacag actcacagtt tcccgtggac ggtcggccaa   300
gggaccaagg tggaaatcaa a                                              321
```

<210> SEQ ID NO 234
<211> LENGTH: 107
<212> TYPE: PRT
<213> ORGANISM: Artificial Sequence
<220> FEATURE:
<223> OTHER INFORMATION: synthetic

<400> SEQUENCE: 234

```
Asp Ile Gln Met Thr Gln Ser Pro Ser Ser Val Ser Ala Ser Ile Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Val Pro Lys Leu Leu Ile
         35                  40                  45

Tyr Ala Ala Ser Ser Leu Gln Ser Gly Phe Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr His Ser Phe Pro Trp
                 85                  90                  95

Thr Val Gly Gln Gly Thr Lys Val Glu Ile Lys
            100                 105
```

<210> SEQ ID NO 235
<211> LENGTH: 18
<212> TYPE: DNA
<213> ORGANISM: Artificial Sequence
<220> FEATURE:
<223> OTHER INFORMATION: synthetic

<400> SEQUENCE: 235
cagggaatca gcagttgg                                                    18

<210> SEQ ID NO 236
<211> LENGTH: 6
<212> TYPE: PRT
<213> ORGANISM: Artificial Sequence
<220> FEATURE:
<223> OTHER INFORMATION: synthetic

<400> SEQUENCE: 236

Gln Gly Ile Ser Ser Trp
 1               5

<210> SEQ ID NO 237
<211> LENGTH: 9
<212> TYPE: DNA
<213> ORGANISM: Artificial Sequence
<220> FEATURE:
<223> OTHER INFORMATION: synthetic

<400> SEQUENCE: 237 gctgcgtcc                                                               9

<210> SEQ ID NO 238
<211> LENGTH: 3
<212> TYPE: PRT
<213> ORGANISM: Artificial Sequence
<220> FEATURE:
<223> OTHER INFORMATION: synthetic

<400> SEQUENCE: 238

Ala Ala Ser
 1

<210> SEQ ID NO 239
<211> LENGTH: 24
<212> TYPE: DNA
<213> ORGANISM: Artificial Sequence
<220> FEATURE:
<223> OTHER INFORMATION: synthetic

<400> SEQUENCE: 239
caacagactc acagtttccc gtgg                                             24

<210> SEQ ID NO 240
<211> LENGTH: 8
<212> TYPE: PRT
<213> ORGANISM: Artificial Sequence
<220> FEATURE:
<223> OTHER INFORMATION: synthetic

<400> SEQUENCE: 240

Gln Gln Thr His Ser Phe Pro Trp
 1               5

<210> SEQ ID NO 241

<211> LENGTH: 366
<212> TYPE: DNA
<213> ORGANISM: Artificial Sequence
<220> FEATURE:
<223> OTHER INFORMATION: synthetic

<400> SEQUENCE: 241

```
gaggtgcagc tggtggagtc tgggggaggc ttggtacagc ctggggggtc cctgagactc      60
tcctgtgcag cctctggatt caccgttagg agctatttca tgacctgggt ccgccaggtt     120
ccagggaagg ggctggaggg ggtctcagct attagtggca ttagtggtgg cacatactac     180
acagactccg ttaagggccg gttcaccatc tccagagaca attccaagaa cacgctgttt     240
ctgcaaatga acagcctgag agccgaggac acggccgtat atttctgtgc gagaacggtg     300
tatagtagta gttactacgg gggcttccag cactggggcc agggcaccct ggtcaccgtc     360
tcctca                                                                366
```

<210> SEQ ID NO 242
<211> LENGTH: 122
<212> TYPE: PRT
<213> ORGANISM: Artificial Sequence
<220> FEATURE:
<223> OTHER INFORMATION: synthetic

<400> SEQUENCE: 242

```
Glu Val Gln Leu Val Glu Ser Gly Gly Gly Leu Val Gln Pro Gly Gly
  1               5                  10                  15
Ser Leu Arg Leu Ser Cys Ala Ala Ser Gly Phe Thr Leu Arg Ser Tyr
             20                  25                  30
Phe Met Thr Trp Val Arg Gln Val Pro Gly Lys Gly Leu Glu Gly Val
         35                  40                  45
Ser Ala Ile Ser Gly Ile Ser Gly Gly Thr Tyr Tyr Thr Asp Ser Val
     50                  55                  60
Lys Gly Arg Phe Thr Ile Ser Arg Asp Asn Ser Lys Asn Thr Leu Phe
 65                  70                  75                  80
Leu Gln Met Asn Ser Leu Arg Ala Glu Asp Thr Ala Val Tyr Phe Cys
                 85                  90                  95
Ala Arg Thr Val Tyr Ser Ser Ser Tyr Tyr Gly Gly Phe Gln His Trp
            100                 105                 110
Gly Gln Gly Thr Leu Val Thr Val Ser Ser
            115                 120
```

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243

```
ggattcaccc ttaggagcta tttc                                             24
```

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

Gly Phe Thr Leu Arg Ser Tyr Phe

<210> SEQ ID NO 245
<211> LENGTH: 24
<212> TYPE: DNA
<213> ORGANISM: Artificial Sequence
<220> FEATURE:
<223> OTHER INFORMATION: synthetic

<400> SEQUENCE: 245
attagtggca ttagtggtgg caca                                        24

<210> SEQ ID NO 246
<211> LENGTH: 8
<212> TYPE: PRT
<213> ORGANISM: Artificial Sequence
<220> FEATURE:
<223> OTHER INFORMATION: synthetic

<400> SEQUENCE: 246

Ile Ser Gly Ile Ser Gly Gly Thr
1               5

<210> SEQ ID NO 247
<211> LENGTH: 45
<212> TYPE: DNA
<213> ORGANISM: Artificial Sequence
<220> FEATURE:
<223> OTHER INFORMATION: synthetic

<400> SEQUENCE: 247
gcgagaacgg tgtatagtag tagttactac gggggcttcc agcac                 45

<210> SEQ ID NO 248
<211> LENGTH: 15
<212> TYPE: PRT
<213> ORGANISM: Artificial Sequence
<220> FEATURE:
<223> OTHER INFORMATION: synthetic

<400> SEQUENCE: 248

Ala Arg Thr Val Tyr Ser Ser Ser Tyr Tyr Gly Gly Phe Gln His
1               5                   10                  15

<210> SEQ ID NO 249
<211> LENGTH: 321
<212> TYPE: DNA
<213> ORGANISM: Artificial Sequence
<220> FEATURE:
<223> OTHER INFORMATION: synthetic

<400> SEQUENCE: 249
gacatccaga tgacccagtc tccatcttcc gtgtctgtat ctgtaggaga cagagtcacc    60
atcacttgtc gggcgagtca gggtattagc agttggttag cctggtatca gcagaaacca   120
gggaaagccc ctaagctcct gatctatgtt gcatccagtt tacaaagtgg ggtcccatca   180
aggttcagcg gcagtggatc tgggacagat ttcactctca ccatcagcag cctgcagcct   240
gaagattttg caacttacta ttgtcaacag actaacagtt tccctctcac tttcggcgga   300
gggaccaagg tggagatcaa a                                            321

<210> SEQ ID NO 250
<211> LENGTH: 107
<212> TYPE: PRT
<213> ORGANISM: Artificial Sequence -continued
<220> FEATURE:
<223> OTHER INFORMATION: synthetic

<400> SEQUENCE: 250

Asp Ile Gln Met Thr Gln Ser Pro Ser Ser Val Ser Val Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Leu
                85                  90                  95

Thr Phe Gly Gly Gly Thr Lys Val Glu Ile Lys
            100                 105

<210> SEQ ID NO 251
<211> LENGTH: 18
<212> TYPE: DNA
<213> ORGANISM: Artificial Sequence
<220> FEATURE:
<223> OTHER INFORMATION: synthetic

<400> SEQUENCE: 251
cagggtatta gcagttgg                                                 18

<210> SEQ ID NO 252
<211> LENGTH: 6
<212> TYPE: PRT
<213> ORGANISM: Artificial Sequence
<220> FEATURE:
<223> OTHER INFORMATION: synthetic

<400> SEQUENCE: 252

Gln Gly Ile Ser Ser Trp
1               5

<210> SEQ ID NO 253
<211> LENGTH: 9
<212> TYPE: DNA
<213> ORGANISM: Artificial Sequence
<220> FEATURE:
<223> OTHER INFORMATION: synthetic

<400> SEQUENCE: 253 gttgcatcc                                                            9

<210> SEQ ID NO 254
<211> LENGTH: 3
<212> TYPE: PRT
<213> ORGANISM: Artificial Sequence
<220> FEATURE:
<223> OTHER INFORMATION: synthetic

<400> SEQUENCE: 254

Val Ala Ser
1

<210> SEQ ID NO 255
<211> LENGTH: 27

<210> SEQ ID NO 256
<211> LENGTH: 9
<212> TYPE: PRT
<213> ORGANISM: Artificial Sequence
<220> FEATURE:
<223> OTHER INFORMATION: synthetic

<400> SEQUENCE: 255
caacagacta acagtttccc tctcact    27

<210> SEQ ID NO 256
<211> LENGTH: 9
<212> TYPE: PRT
<213> ORGANISM: Artificial Sequence
<220> FEATURE:
<223> OTHER INFORMATION: synthetic

<400> SEQUENCE: 256

Gln Gln Thr Asn Ser Phe Pro Leu Thr
 1               5

<210> SEQ ID NO 257
<211> LENGTH: 366
<212> TYPE: DNA
<213> ORGANISM: Artificial Sequence
<220> FEATURE:
<223> OTHER INFORMATION: synthetic

<400> SEQUENCE: 257
gaggtgcagc tggtggagtc tgggggaggc ttggtacagc ctggggggtc cctgagactc    60
tcctgtgcag cctctggatt caccctagg agttatgtca tgtactgggt ccgccagggt    120
ccagggaagg ggctggaggg ggtctcaggt attagtggca gtagtggtgg cacatactac    180
acagactccg tgaagggccg gttcaccatc tccagagaca attccaagaa cacgctgttt    240
ctgcaaatga acagcctgag agccgaggac acggccgtat attctgtgc gagatcggtg    300 tatagtacca cctggtacgg gggcttccag cactgggggcc agggcaccct ggtcaccgtc    360
tcctca    366

<210> SEQ ID NO 258
<211> LENGTH: 122
<212> TYPE: PRT
<213> ORGANISM: Artificial Sequence
<220> FEATURE:
<223> OTHER INFORMATION: synthetic

<400> SEQUENCE: 258

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Arg Ser Tyr
             20                  25                  30

Val Met Tyr Trp Val Arg Gln Gly Pro Gly Lys Gly Leu Glu Gly Val
         35                  40                  45

Ser Gly Ile Ser Gly Ser Ser Gly Gly Thr Tyr Tyr Thr Asp Ser Val
     50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Glu Asp Thr Ala Val Tyr Phe Cys
                 85                  90                  95

Ala Arg Ser Val Tyr Ser Thr Thr Trp Tyr Gly Gly Phe Gln His Trp
            100                 105                 110

Gly Gln Gly Thr Leu Val Thr Val Ser Ser
            115                 120

<210> SEQ ID NO 259
<211> LENGTH: 24
<212> TYPE: DNA
<213> ORGANISM: Artificial Sequence
<220> FEATURE:
<223> OTHER INFORMATION: synthetic

<400> SEQUENCE: 259
ggattcaccc ttaggagtta tgtc                                          24

<210> SEQ ID NO 260
<211> LENGTH: 8
<212> TYPE: PRT
<213> ORGANISM: Artificial Sequence
<220> FEATURE:
<223> OTHER INFORMATION: synthetic

<400> SEQUENCE: 260

Gly Phe Thr Leu Arg Ser Tyr Val
 1               5

<210> SEQ ID NO 261
<211> LENGTH: 24
<212> TYPE: DNA
<213> ORGANISM: Artificial Sequence
<220> FEATURE:
<223> OTHER INFORMATION: synthetic

<400> SEQUENCE: 261
attagtggca gtagtggtgg caca                                          24

<210> SEQ ID NO 262
<211> LENGTH: 8
<212> TYPE: PRT
<213> ORGANISM: Artificial Sequence
<220> FEATURE:
<223> OTHER INFORMATION: synthetic

<400> SEQUENCE: 262

Ile Ser Gly Ser Ser Gly Gly Thr
 1               5

<210> SEQ ID NO 263
<211> LENGTH: 45
<212> TYPE: DNA
<213> ORGANISM: Artificial Sequence
<220> FEATURE:
<223> OTHER INFORMATION: synthetic

<400> SEQUENCE: 263
gcgagatcgg tgtatagtac cacctggtac gggggcttcc agcac                   45

<210> SEQ ID NO 264
<211> LENGTH: 15
<212> TYPE: PRT
<213> ORGANISM: Artificial Sequence
<220> FEATURE:
<223> OTHER INFORMATION: synthetic

<400> SEQUENCE: 264

Ala Arg Ser Val Tyr Ser Thr Thr Trp Tyr Gly Gly Phe Gln His
 1               5                  10                  15

<210> SEQ ID NO 265
<211> LENGTH: 321

<212> TYPE: DNA
<213> ORGANISM: Artificial Sequence
<220> FEATURE:
<223> OTHER INFORMATION: synthetic

<400> SEQUENCE: 265

```
gacatccaga tgacccagtc tccatcttcc gtgtctgtat ctgtgggaga cagagtcacc    60
atcacttgtc gggcgagtca ggttattagc agttggttag cctggtatca gctgaaacca   120
gggaaagccc ctaaactcct gatctatgct gcatccagtt tacaaagtgg ggtcccatca   180
aggttcagcg gcagtggatc tgggacagat ttcactctca ccatcagcgg cctgcagcct   240
gaagattttg cagtttacta ttgtcaacag actaacagtt tccctctcac tttcggcgga   300
gggaccaagg tggagatcaa a                                             321
```

<210> SEQ ID NO 266
<211> LENGTH: 107
<212> TYPE: PRT
<213> ORGANISM: Artificial Sequence
<220> FEATURE:
<223> OTHER INFORMATION: synthetic

<400> SEQUENCE: 266

```
Asp Ile Gln Met Thr Gln Ser Pro Ser Ser Val Ser Val Ser Val Gly
  1               5                  10                  15

Asp Arg Val Thr Ile Thr Cys Arg Ala Ser Gln Val Ile Ser Ser Trp
             20                  25                  30

Leu Ala Trp Tyr Gln Leu Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Gly Leu Gln Pro
 65                  70                  75                  80

Glu Asp Phe Ala Val Tyr Tyr Cys Gln Gln Thr Asn Ser Phe Pro Leu
                 85                  90                  95

Thr Phe Gly Gly Gly Thr Lys Val Glu Ile Lys
            100                 105
```

<210> SEQ ID NO 267
<211> LENGTH: 18
<212> TYPE: DNA
<213> ORGANISM: Artificial Sequence
<220> FEATURE:
<223> OTHER INFORMATION: synthetic

<400> SEQUENCE: 267

```
caggttatta gcagttgg                                                  18
```

<210> SEQ ID NO 268
<211> LENGTH: 6
<212> TYPE: PRT
<213> ORGANISM: Artificial Sequence
<220> FEATURE:
<223> OTHER INFORMATION: synthetic

<400> SEQUENCE: 268

```
Gln Val Ile Ser Ser Trp
  1               5
```

<210> SEQ ID NO 269
<211> LENGTH: 9
<212> TYPE: DNA

```
<213> ORGANISM: Artificial Sequence
<220> FEATURE:
<223> OTHER INFORMATION: synthetic

<400> SEQUENCE: 269 gctgcatcc                                                                    9

<210> SEQ ID NO 270
<211> LENGTH: 3
<212> TYPE: PRT
<213> ORGANISM: Artificial Sequence
<220> FEATURE:
<223> OTHER INFORMATION: synthetic

<400> SEQUENCE: 270

Ala Ala Ser
 1

<210> SEQ ID NO 271
<211> LENGTH: 27
<212> TYPE: DNA
<213> ORGANISM: Artificial Sequence
<220> FEATURE:
<223> OTHER INFORMATION: synthetic

<400> SEQUENCE: 271
caacagacta acagtttccc tctcact                                               27

<210> SEQ ID NO 272
<211> LENGTH: 9
<212> TYPE: PRT
<213> ORGANISM: Artificial Sequence
<220> FEATURE:
<223> OTHER INFORMATION: synthetic

<400> SEQUENCE: 272

Gln Gln Thr Asn Ser Phe Pro Leu Thr
 1               5

<210> SEQ ID NO 273
<211> LENGTH: 366
<212> TYPE: DNA
<213> ORGANISM: Artificial Sequence
<220> FEATURE:
<223> OTHER INFORMATION: synthetic

<400> SEQUENCE: 273
gaggtgcagc tggtggagtc tgggggaaac ttggaacagc ctgggggtc ccttagactc            60 tcctgtacag cctctggatt cacctttagc agatctgcca tgaactgggt ccgccgggct          120
ccagggaagg ggctggagtg ggtctcagga attagtggta gtggtggtcg aacatactac          180
gcagactccg tgaagggccg gttcaccatc tccagagaca attccaagaa tacgctatat          240
ctgcaaatga acagcctgag cgccgaggac acggccgcat attactgtgc gaaagattcg          300
tatactacca gttggtacgg aggtatggac gtctggggcc acgggaccac ggtcaccgtc          360
tcctca                                                                   366

<210> SEQ ID NO 274
<211> LENGTH: 122
<212> TYPE: PRT
<213> ORGANISM: Artificial Sequence
<220> FEATURE:
<223> OTHER INFORMATION: synthetic

<400> SEQUENCE: 274
```

Glu Val Gln Leu Val Glu Ser Gly Gly Asn Leu Glu Gln Pro Gly Gly
1               5                   10                  15

Ser Leu Arg Leu Ser Cys Thr Ala Ser Gly Phe Thr Phe Ser Arg Ser
            20                  25                  30

Ala Met Asn Trp Val Arg Arg Ala Pro Gly Lys Gly Leu Glu Trp Val
                35                  40                  45

Ser Gly Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Ala Tyr Tyr Cys
                85                  90                  95

Ala Lys Asp Ser Tyr Thr Thr Ser Trp Tyr Gly Gly Met Asp Val Trp
            100                 105                 110

Gly His Gly Thr Thr Val Thr Val Ser Ser
        115                 120

<210> SEQ ID NO 275
<211> LENGTH: 24
<212> TYPE: DNA
<213> ORGANISM: Artificial Sequence
<220> FEATURE:
<223> OTHER INFORMATION: synthetic

<400> SEQUENCE: 275
ggattcacct ttagcagatc tgcc                                          24

<210> SEQ ID NO 276
<211> LENGTH: 8
<212> TYPE: PRT
<213> ORGANISM: Artificial Sequence
<220> FEATURE:
<223> OTHER INFORMATION: synthetic

<400> SEQUENCE: 276

Gly Phe Thr Phe Ser Arg Ser Ala
1               5

<210> SEQ ID NO 277
<211> LENGTH: 24
<212> TYPE: DNA
<213> ORGANISM: Artificial Sequence
<220> FEATURE:
<223> OTHER INFORMATION: synthetic

<400> SEQUENCE: 277
attagtggta gtggtggtcg aaca                                          24

<210> SEQ ID NO 278
<211> LENGTH: 8
<212> TYPE: PRT
<213> ORGANISM: Artificial Sequence
<220> FEATURE:
<223> OTHER INFORMATION: synthetic

<400> SEQUENCE: 278

Ile Ser Gly Ser Gly Gly Arg Thr
1               5

<210> SEQ ID NO 279
<211> LENGTH: 45
<212> TYPE: DNA

<213> ORGANISM: Artificial Sequence
<220> FEATURE:
<223> OTHER INFORMATION: synthetic

<400> SEQUENCE: 279

```
gcgaaagatt cgtatactac cagttggtac ggaggtatgg acgtc              45
```

<210> SEQ ID NO 280
<211> LENGTH: 15
<212> TYPE: PRT
<213> ORGANISM: Artificial Sequence
<220> FEATURE:
<223> OTHER INFORMATION: synthetic

<400> SEQUENCE: 280

Ala Lys Asp Ser Tyr Thr Thr Ser Trp Tyr Gly Gly Met Asp Val
1               5                   10                  15

<210> SEQ ID NO 281
<211> LENGTH: 321
<212> TYPE: DNA
<213> ORGANISM: Artificial Sequence
<220> FEATURE:
<223> OTHER INFORMATION: synthetic

<400> SEQUENCE: 281

```
gacatccaga tgacccagtc tccatcttcc gtgtctgcat ctgtaggaga cagagtcacc    60
atcacttgtc gggcgagtca gggtatttc  agctggttag cctggtatca gcagaaacca  120
ggaaaagccc ctaagctcct gatctatgct gcttccagtt acaaagtggg gtcccatca   180
agattcagcg gcagtggatc tgggacagat ttcactctca ccatcagcag cctgcagcct  240
gaggattttg caatttacta ttgtcaacag gctaacagtg tcccgatcac cttcggccaa  300
gggacacgac tggagattaa a                                            321
```

<210> SEQ ID NO 282
<211> LENGTH: 107
<212> TYPE: PRT
<213> ORGANISM: Artificial Sequence
<220> FEATURE:
<223> OTHER INFORMATION: synthetic

<400> SEQUENCE: 282

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Phe Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Ala Asn Ser Val Pro Ile
                85                  90                  95

Thr Phe Gly Gln Gly Thr Arg Leu Glu Ile Lys
            100                 105

<210> SEQ ID NO 283
<211> LENGTH: 18
<212> TYPE: DNA
<213> ORGANISM: Artificial Sequence

```
<220> FEATURE:
<223> OTHER INFORMATION: synthetic

<400> SEQUENCE: 283
cagggtattt tcagctgg                                              18

<210> SEQ ID NO 284
<211> LENGTH: 6
<212> TYPE: PRT
<213> ORGANISM: Artificial Sequence
<220> FEATURE:
<223> OTHER INFORMATION: synthetic

<400> SEQUENCE: 284

Gln Gly Ile Phe Ser Trp
 1               5

<210> SEQ ID NO 285
<211> LENGTH: 9
<212> TYPE: DNA
<213> ORGANISM: Artificial Sequence
<220> FEATURE:
<223> OTHER INFORMATION: synthetic

<400> SEQUENCE: 285 gctgcttcc                                                         9

<210> SEQ ID NO 286
<211> LENGTH: 3
<212> TYPE: PRT
<213> ORGANISM: Artificial Sequence
<220> FEATURE:
<223> OTHER INFORMATION: synthetic

<400> SEQUENCE: 286

Ala Ala Ser
 1

<210> SEQ ID NO 287
<211> LENGTH: 27
<212> TYPE: DNA
<213> ORGANISM: Artificial Sequence
<220> FEATURE:
<223> OTHER INFORMATION: synthetic

<400> SEQUENCE: 287
caacaggcta acagtgtccc gatcacc                                    27

<210> SEQ ID NO 288
<211> LENGTH: 9
<212> TYPE: PRT
<213> ORGANISM: Artificial Sequence
<220> FEATURE:
<223> OTHER INFORMATION: synthetic

<400> SEQUENCE: 288

Gln Gln Ala Asn Ser Val Pro Ile Thr
 1               5

<210> SEQ ID NO 289
<211> LENGTH: 366
<212> TYPE: DNA
<213> ORGANISM: Artificial Sequence
<220> FEATURE:
<223> OTHER INFORMATION: synthetic

<400> SEQUENCE: 289
```

```
gaggtgcagc tggtggagtc tgggggaggc ttggtacagc ctgggggtc cctgagactc      60 tcctgttcag cctctggatt cacctttagc agctatgcca tgaactgggt ccgccaggct    120
ccagggaagg gctggagtg gtcaccgct attagtggca gtggtggtgg cacatactac     180
gcagactccg tgaagggccg gttcaccatc tccagagaca attccaagaa ctcgctgttt    240
ctgcaattga acagcctgag agccgaggac acggccgtgt attactgtgc gaaacaaacg    300
tataccagca gctggtacgg tggctttgat atctggggcc aggggacaat ggtcaccgtc    360
tcttca                                                                366
```

<210> SEQ ID NO 290
<211> LENGTH: 122
<212> TYPE: PRT
<213> ORGANISM: Artificial Sequence
<220> FEATURE:
<223> OTHER INFORMATION: synthetic

<400> SEQUENCE: 290

Glu Val Gln Leu Val Glu Ser Gly Gly Gly Leu Val Gln Pro Gly Gly
 1               5                   10                  15

Ser Leu Arg Leu Ser Cys Ser Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Thr Ala Ile Ser Gly Ser Gly Gly Thr Tyr Tyr Ala Asp Ser Val
    50                  55                  60

Lys Gly Arg Phe Thr Ile Ser Arg Asp Asn Lys Asn Ser Leu Phe
65                  70                  75                  80

Leu Gln Leu Asn Ser Leu Arg Ala Glu Asp Thr Ala Val Tyr Tyr Cys
                85                  90                  95

Ala Lys Gln Thr Tyr Thr Ser Ser Trp Tyr Gly Gly Phe Asp Ile Trp
            100                 105                 110

Gly Gln Gly Thr Met Val Thr Val Ser Ser
        115                 120

<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291

```
ggattcacct ttagcagcta tgcc                                             24
```

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gly Phe Thr Phe Ser Ser Tyr Ala
 1               5

<210> SEQ ID NO 293
<211> LENGTH: 24
<212> TYPE: DNA
<213> ORGANISM: Artificial Sequence

```
<220> FEATURE:
<223> OTHER INFORMATION: synthetic

<400> SEQUENCE: 293
attagtggca gtggtggtgg caca                                                  24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

Ile Ser Gly Ser Gly Gly Gly Thr
1               5

<210> SEQ ID NO 295
<211> LENGTH: 45
<212> TYPE: DNA
<213> ORGANISM: Artificial Sequence
<220> FEATURE:
<223> OTHER INFORMATION: synthetic

<400> SEQUENCE: 295
gcgaaacaaa cgtataccag cagctggtac ggtggctttg atatc                           45

<210> SEQ ID NO 296
<211> LENGTH: 15
<212> TYPE: PRT
<213> ORGANISM: Artificial Sequence
<220> FEATURE:
<223> OTHER INFORMATION: synthetic

<400> SEQUENCE: 296

Ala Lys Gln Thr Tyr Thr Ser Ser Trp Tyr Gly Gly Phe Asp Ile
1               5                   10                  15

<210> SEQ ID NO 297
<211> LENGTH: 321
<212> TYPE: DNA
<213> ORGANISM: Artificial Sequence
<220> FEATURE:
<223> OTHER INFORMATION: synthetic

<400> SEQUENCE: 297
gacatccaga tgacccagtc gccatcttcc gtgtccgcgt ctgtaggaga cagagtcacc           60
atcacttgtc gggcgagtca gggttttagt tcctggttag cctggtatca gcagatacca          120
gggaaagccc ccaagctcct gatctatgct gcatcaaggt tgcaaagtgg ggtcccatcc          180
aggttccgcg gcagtggatc tgggacagat ttcactctca ccatcagcag cctgcagcct          240
gaggattttg caacttacta ttgtcaacag gctaacagtt tcccgctcac tttcggcgga          300
gggaccaagg tggagatcaa a                                                    321

<210> SEQ ID NO 298
<211> LENGTH: 107
<212> TYPE: PRT
<213> ORGANISM: Artificial Sequence
<220> FEATURE:
<223> OTHER INFORMATION: synthetic

<400> SEQUENCE: 298

Asp Ile Gln Met Thr Gln Ser Pro Ser Ser Val Ser Ala Ser Val Gly
1               5                   10                  15
```

Asp Arg Val Thr Ile Thr Cys Arg Ala Ser Gln Gly Phe Ser Ser Trp
            20                  25                  30

Leu Ala Trp Tyr Gln Gln Ile Pro Gly Lys Ala Pro Lys Leu Leu Ile
        35                  40                  45

Tyr Ala Ala Ser Arg Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 299
<211> LENGTH: 18
<212> TYPE: DNA
<213> ORGANISM: Artificial Sequence
<220> FEATURE:
<223> OTHER INFORMATION: synthetic

<400> SEQUENCE: 299
cagggtttta gttcctgg                                                      18

<210> SEQ ID NO 300
<211> LENGTH: 6
<212> TYPE: PRT
<213> ORGANISM: Artificial Sequence
<220> FEATURE:
<223> OTHER INFORMATION: synthetic

<400> SEQUENCE: 300

Gln Gly Phe Ser Ser Trp
1               5

<210> SEQ ID NO 301
<211> LENGTH: 9
<212> TYPE: DNA
<213> ORGANISM: Artificial Sequence
<220> FEATURE:
<223> OTHER INFORMATION: synthetic

<400> SEQUENCE: 301 gctgcatca                                                                 9

<210> SEQ ID NO 302
<211> LENGTH: 3
<212> TYPE: PRT
<213> ORGANISM: Artificial Sequence
<220> FEATURE:
<223> OTHER INFORMATION: synthetic

<400> SEQUENCE: 302

Ala Ala Ser
1

<210> SEQ ID NO 303
<211> LENGTH: 27
<212> TYPE: DNA
<213> ORGANISM: Artificial Sequence
<220> FEATURE:
<223> OTHER INFORMATION: synthetic

<400> SEQUENCE: 303

```
caacaggcta acagtttccc gctcact                                              27
```

<210> SEQ ID NO 304
<211> LENGTH: 9
<212> TYPE: PRT
<213> ORGANISM: Artificial Sequence
<220> FEATURE:
<223> OTHER INFORMATION: synthetic

<400> SEQUENCE: 304

Gln Gln Ala Asn Ser Phe Pro Leu Thr
 1               5

<210> SEQ ID NO 305
<211> LENGTH: 2718
<212> TYPE: DNA
<213> ORGANISM: Artificial Sequence
<220> FEATURE:
<223> OTHER INFORMATION: GenBank NM_033439.3: Human IL-33 nucleic acid

<400> SEQUENCE: 305

```
agtctacaga ctcctccgaa cacagagctg cagctcttca gggaagaaat caaaacaaga        60
tcacaagaat actgaaaaat gaagcctaaa atgaagtatt caaccaacaa aatttccaca       120
gcaaagtgga agaacacagc aagcaaagcc ttgtgtttca agctgggaaa atcccaacag       180
aaggccaaag aagtttgccc catgtacttt atgaagctcc gctctggcct tatgataaaa       240
aaggaggcct gttactttag gagagaaacc accaaaaggc cttcactgaa aacaggtaga       300
aagcacaaaa gacatctggt actcgctgcc tgtcaacagc agtctactgt ggagtgcttt       360
gcctttggta tatcaggggt ccagaaatat actagagcac ttcatgattc aagtatcaca       420
ggaatttcac ctattacaga gtatcttgct tctctaagca catacaatga tcaatccatt       480
acttttgctt tggaggatga agttatgag atatatgttg aagacttgaa aaagatgaa        540
aagaaagata aggtgttact gagttactat gagtctcaac cccctcaaa tgaatcaggt        600
gacggtgttg atggtaagat gttaatggta accctgagtc ctacaaaaga cttctggttg       660
catgccaaca caaggaaca ctctgtggag ctccataagt gtgaaaaacc actgccagac        720
caggccttct ttgtccttca taatatgcac tccaactgtg tttcatttga atgcaagact       780
gatcctggag tgtttatagg tgtaaaggat aatcatcttg ctctgattaa gtagactct        840
tctgagaatt tgtgtactga aaatatcttg tttaagctct ctgaaactta gttgatggaa       900
acctgtgagt cttgggttga gtacccaaat gctaccactg gagaaggaat gagagataaa       960
gaaagagaca ggtgacatct aagggaaatg aagagtgctt agcatgtgtg gaatgttttc      1020
catattatgt ataaaatat tttttctaat cctccagtta ttcttttatt tccctctgta       1080
taactgcatc ttcaatacaa gtatcagtat attaaatagg gtattggtaa agaaacggtc      1140
aacattctaa agagatacag tctgaccttt acttttctct agtttcagtc cagaaagaac      1200
ttcatattta gagctaaggc cactgaggaa agagccatag cttaagtctc tatgtagaca      1260
gggatccatt ttaaagagct acttagagaa ataattttcc acagttccaa acgataggct      1320
caaacactag agctgctagt aaaaagaaga ccagatgctt cacagaatta tcattttttc      1380
aactggaata aaacaccagg tttgtttgta gatgtcttag gcaacactca gagcagatct      1440
cccttactgt caggggatat ggaacttcaa aggcccacat ggcaagccag gtaacataaa      1500
tgtgtgaaaa agtaaagata actaaaaaat ttagaaaaat aaatccagta tttgtaaagt      1560
gaataacttc atttctaatt gtttaatttt taaaattctg attttatat attgagttta      1620
```

```
agcaaggcat tcttacacga ggaagtgaag taaattttag ttcagacata aaatttcact      1680
tattaggaat atgtaacatg ctaaaacttt tttttttta aagagtactg agtcacaaca      1740
tgttttagag catccaagta ccatataatc caactatcat ggtaaggcca gaaatcttct      1800
aacctaccag agcctagatg agacaccgaa ttaacattaa aatttcagta actgactgtc      1860
cctcatgtcc atggcctacc atcccttctg accctggctt ccagggacct atgtctttta      1920
atactcactg tcacattggg caaagttgct tctaatcctt atttcccatg tgcacaagtc      1980
tttttgtatt ccagcttcct gataacactg cttactgtgg aatattcatt tgacatctgt      2040 ctctttcat ttcttttaac taccatgccc ttgatatatc ttttgcacct gctgaacttc      2100
atttctgtat cacctgacct ctggatgcca aaacgtttat tctgctttgt ctgttgtaga      2160 atttagata aagctattaa tggcaatatt ttttgctaa acgttttgt ttttactgt      2220 cactagggca ataaaattta tactcaacca tataataaca tttttaact actaaaggag      2280 tagttttat tttaaagtct tagcaatttc tattacaact tttcttagac ttaacactta      2340
tgataaatga ctaacatagt aacagaatct ttatgaaata tgacctttc tgaaaataca      2400 tacttttaca tttctacttt attgagacct attagatgta agtgctagta gaatataaga      2460
taaaagaggc tgagaattac catacaaggg tattacaact gtaaacaat ttatctttgt      2520 ttcattgttc tgtcaataat tgttaccaaa gagataaaaa taaaagcaga atgtatatca      2580
tcccatctga aaaacactaa ttattgacat gtgcatctgt acaataaact taaaatgatt      2640
attaaataat caaatatatc tactacattg tttatattat tgaataaagt atattttcca      2700
aatgtaaaaa aaaaaaaa                                                   2718
```

<210> SEQ ID NO 306
<211> LENGTH: 270
<212> TYPE: PRT
<213> ORGANISM: Artificial Sequence
<220> FEATURE:
<223> OTHER INFORMATION: Human IL-33 Protein GenBank O95760

<400> SEQUENCE: 306

```
Met Lys Pro Lys Met Lys Tyr Ser Thr Asn Lys Ile Ser Thr Ala Lys
 1               5                  10                  15

Trp Lys Asn Thr Ala Ser Lys Ala Leu Cys Phe Lys Leu Gly Lys Ser
             20                  25                  30

Gln Gln Lys Ala Lys Glu Val Cys Pro Met Tyr Phe Met Lys Leu Arg
         35                  40                  45

Ser Gly Leu Met Ile Lys Lys Glu Ala Cys Tyr Phe Arg Arg Glu Thr
     50                  55                  60

Thr Lys Arg Pro Ser Leu Lys Thr Gly Arg Lys His Lys Arg His Leu
 65                  70                  75                  80

Val Leu Ala Ala Cys Gln Gln Gln Ser Thr Val Glu Cys Phe Ala Phe
                 85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
```

```
            165                 170                 175
Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
            195                 200                 205

Glu Lys Pro Leu Pro Asp Gln Ala Phe Phe Val Leu His Asn Met His
        210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270

<210> SEQ ID NO 307
<211> LENGTH: 354
<212> TYPE: DNA
<213> ORGANISM: Artificial Sequence
<220> FEATURE:
<223> OTHER INFORMATION: synthetic

<400> SEQUENCE: 307
caggtcacct tgaaggagtc tggtcctgtg ctggtgaaac ccacagagag cctcacgctg      60
acctgctccg tctctggatt ctcactcagt aatgttagaa tgggtgtgag ctggatccgt     120
cagtccccag ggaaggccct ggagtggctt gcacacattt tttcgaatga cgaaaaatcc     180
tacaccacat ctctgaagac caggctcacc atctccaagg acacctccag aagccaggtg     240
gtccttacca tgaccgacat ggaccctggg acacagcca catattactg tgcacggata     300
cggaatttgg cctttaatta ctggggccag ggaaccctgg tcaccgtctc ctca          354

<210> SEQ ID NO 308
<211> LENGTH: 118
<212> TYPE: PRT
<213> ORGANISM: Artificial Sequence
<220> FEATURE:
<223> OTHER INFORMATION: synthetic

<400> SEQUENCE: 308

Gln Val Thr Leu Lys Glu Ser Gly Pro Val Leu Val Lys Pro Thr Glu
1               5                   10                  15

Ser Leu Thr Leu Thr Cys Ser Val Ser Gly Phe Ser Leu Ser Asn Val
            20                  25                  30

Arg Met Gly Val Ser Trp Ile Arg Gln Ser Pro Gly Lys Ala Leu Glu
        35                  40                  45

Trp Leu Ala His Ile Phe Ser Asn Asp Glu Lys Ser Tyr Thr Thr Ser
    50                  55                  60

Leu Lys Thr Arg Leu Thr Ile Ser Lys Asp Thr Ser Arg Ser Gln Val
65                  70                  75                  80

Val Leu Thr Met Thr Asp Met Asp Pro Gly Asp Thr Ala Thr Tyr Tyr
                85                  90                  95

Cys Ala Arg Ile Arg Asn Leu Ala Phe Asn Tyr Trp Gly Gln Gly Thr
            100                 105                 110

Leu Val Thr Val Ser Ser
        115

<210> SEQ ID NO 309
<211> LENGTH: 30
```

<212> TYPE: DNA
<213> ORGANISM: Artificial Sequence
<220> FEATURE:
<223> OTHER INFORMATION: synthetic

<400> SEQUENCE: 309
ggattctcac tcagtaatgt tagaatgggt          30

<210> SEQ ID NO 310
<211> LENGTH: 10
<212> TYPE: PRT
<213> ORGANISM: Artificial Sequence
<220> FEATURE:
<223> OTHER INFORMATION: synthetic

<400> SEQUENCE: 310

Gly Phe Ser Leu Ser Asn Val Arg Met Gly
 1               5                  10

<210> SEQ ID NO 311
<211> LENGTH: 21
<212> TYPE: DNA
<213> ORGANISM: Artificial Sequence
<220> FEATURE:
<223> OTHER INFORMATION: synthetic

<400> SEQUENCE: 311 atttttcga atgacgaaaa a          21

<210> SEQ ID NO 312
<211> LENGTH: 7
<212> TYPE: PRT
<213> ORGANISM: Artificial Sequence
<220> FEATURE:
<223> OTHER INFORMATION: synthetic

<400> SEQUENCE: 312

Ile Phe Ser Asn Asp Glu Lys
 1               5

<210> SEQ ID NO 313
<211> LENGTH: 30
<212> TYPE: DNA
<213> ORGANISM: Artificial Sequence
<220> FEATURE:
<223> OTHER INFORMATION: synthetic

<400> SEQUENCE: 313
gcacggatac ggaatttggc ctttaattac          30

<210> SEQ ID NO 314
<211> LENGTH: 10
<212> TYPE: PRT
<213> ORGANISM: Artificial Sequence
<220> FEATURE:
<223> OTHER INFORMATION: synthetic

<400> SEQUENCE: 314

Ala Arg Ile Arg Asn Leu Ala Phe Asn Tyr
 1               5                  10

<210> SEQ ID NO 315
<211> LENGTH: 339
<212> TYPE: DNA
<213> ORGANISM: Artificial Sequence
<220> FEATURE:
<223> OTHER INFORMATION: synthetic

<400> SEQUENCE: 315

```
gacttcgtga tgacccagtc tccagactcc ctggctgtgt ctctgggcga gagggccacc    60
atcaactgca agtccagcca gagtgtgtta cacaggtcca gcaataagaa ctacttagct   120
tggtatcagc agaagccagg acagcctcct aacctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatggtact   300
ctatttactt tcggccctgg gaccaaagtg gatatcaaa                          339
```

<210> SEQ ID NO 316
<211> LENGTH: 112
<212> TYPE: PRT
<213> ORGANISM: Artificial Sequence
<220> FEATURE:
<223> OTHER INFORMATION: synthetic

<400> SEQUENCE: 316

```
Asp Phe Val Met Thr Gln Ser Pro Asp Ser Leu Ala Val Ser Leu Gly
 1               5                  10                  15
Glu Arg Ala Thr Ile Asn Cys Lys Ser Ser Gln Ser Val Leu His Arg
            20                  25                  30
Ser Ser Asn Lys Asn Tyr Leu Ala Trp Tyr Gln Gln Lys Pro Gly Gln
        35                  40                  45
Pro Pro Asn Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Gly Thr Leu Phe Thr Phe Gly Pro Gly Thr Lys Val Asp Ile
            100                 105                 110
```

<210> SEQ ID NO 317
<211> LENGTH: 36
<212> TYPE: DNA
<213> ORGANISM: Artificial Sequence
<220> FEATURE:
<223> OTHER INFORMATION: synthetic

<400> SEQUENCE: 317

```
cagagtgtgt tacacaggtc cagcaataag aactac                              36
```

<210> SEQ ID NO 318
<211> LENGTH: 12
<212> TYPE: PRT
<213> ORGANISM: Artificial Sequence
<220> FEATURE:
<223> OTHER INFORMATION: synthetic

<400> SEQUENCE: 318

```
Gln Ser Val Leu His Arg Ser Ser Asn Lys Asn Tyr
 1               5                  10
```

<210> SEQ ID NO 319
<211> LENGTH: 9
<212> TYPE: DNA
<213> ORGANISM: Artificial Sequence
<220> FEATURE:
<223> OTHER INFORMATION: synthetic

<400> SEQUENCE: 319 tgggcatct                                                                                         9

<210> SEQ ID NO 320
<211> LENGTH: 3
<212> TYPE: PRT
<213> ORGANISM: Artificial Sequence
<220> FEATURE:
<223> OTHER INFORMATION: synthetic

<400> SEQUENCE: 320

Trp Ala Ser
 1

<210> SEQ ID NO 321
<211> LENGTH: 27
<212> TYPE: DNA
<213> ORGANISM: Artificial Sequence
<220> FEATURE:
<223> OTHER INFORMATION: synthetic

<400> SEQUENCE: 321
cagcaatatt atggtactct atttact                                                                    27

<210> SEQ ID NO 322
<211> LENGTH: 9
<212> TYPE: PRT
<213> ORGANISM: Artificial Sequence
<220> FEATURE:
<223> OTHER INFORMATION: synthetic

<400> SEQUENCE: 322

Gln Gln Tyr Tyr Gly Thr Leu Phe Thr
 1               5

<210> SEQ ID NO 323
<211> LENGTH: 537
<212> TYPE: PRT
<213> ORGANISM: Artificial Sequence
<220> FEATURE:
<223> OTHER INFORMATION: synthetic

<400> SEQUENCE: 323

Lys Phe Ser Lys Gln Ser Trp Gly Leu Glu Asn Glu Ala Leu Ile Val
 1               5                  10                  15

Arg Cys Pro Arg Gln Gly Lys Pro Ser Tyr Thr Val Asp Trp Tyr Tyr
                20                  25                  30

Ser Gln Thr Asn Lys Ser Ile Pro Thr Gln Glu Arg Asn Arg Val Phe
            35                  40                  45

Ala Ser Gly Gln Leu Leu Lys Phe Leu Pro Ala Ala Val Ala Asp Ser
        50                  55                  60

Gly Ile Tyr Thr Cys Ile Val Arg Ser Pro Thr Phe Asn Arg Thr Gly
 65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Ser Gly Ser Glu Lys Asn Ser Lys
               100                 105                 110

Ile Tyr Cys Pro Thr Ile Asp Leu Tyr Asn Trp Thr Ala Pro Leu Glu
           115                 120                 125

Trp Phe Lys Asn Cys Gln Ala Leu Gln Gly Ser Arg Tyr Arg Ala His
       130                 135                 140

-continued

```
Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu Gln Gly Phe Ser Leu
            180                 185                 190

Phe Pro Val Ile Gly Ala Pro Ala Gln Asn Glu Ile Lys Glu Val Glu
        195                 200                 205

Ile Gly Lys Asn Ala Asn Leu Thr Cys Ser Ala Cys Phe Gly Lys Gly
210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Gly Gln Asn Gln
                245                 250                 255

Ser Phe Ser Asn Gly Leu Ala Cys Leu Asp Met Val Leu Arg Ile Ala
                260                 265                 270

Asp Val Lys Glu Glu Asp Leu Leu Leu Gln Tyr Asp Cys Leu Ala Leu
            275                 280                 285

Asn Leu His Gly Leu Arg Arg His Thr Val Arg Leu Ser Arg Lys Asn
        290                 295                 300

Pro Ile Asp His His Ser Asp Lys Thr His Thr Cys Pro Pro Cys Pro
305                 310                 315                 320

Ala Pro Glu Leu Leu Gly Gly Pro Ser Val Phe Leu Phe Pro Pro Lys
                325                 330                 335

Pro Lys Asp Thr Leu Met Ile Ser Arg Thr Pro Glu Val Thr Cys Val
            340                 345                 350

Val Val Asp Val Ser His Glu Asp Pro Glu Val Lys Phe Asn Trp Tyr
        355                 360                 365

Val Asp Gly Val Glu Val His Asn Ala Lys Thr Lys Pro Arg Glu Glu
    370                 375                 380

Gln Tyr Asn Ser Thr Tyr Arg Val Val Ser Val Leu Thr Val Leu His
385                 390                 395                 400

Gln Asp Trp Leu Asn Gly Lys Glu Tyr Lys Cys Lys Val Ser Asn Lys
                405                 410                 415

Ala Leu Pro Ala Pro Ile Glu Lys Thr Ile Ser Lys Ala Lys Gly Gln
            420                 425                 430

Pro Arg Glu Pro Gln Val Tyr Thr Leu Pro Pro Ser Arg Asp Glu Leu
        435                 440                 445

Thr Lys Asn Gln Val Ser Leu Thr Cys Leu Val Lys Gly Phe Tyr Pro
    450                 455                 460

Ser Asp Ile Ala Val Glu Trp Glu Ser Asn Gly Gln Pro Glu Asn Asn
465                 470                 475                 480

Tyr Lys Thr Thr Pro Pro Val Leu Asp Ser Asp Gly Ser Phe Phe Leu
                485                 490                 495

Tyr Ser Lys Leu Thr Val Asp Lys Ser Arg Trp Gln Gln Gly Asn Val
            500                 505                 510

Phe Ser Cys Ser Val Met His Glu Ala Leu His Asn His Tyr Thr Gln
        515                 520                 525

Lys Ser Leu Ser Leu Ser Pro Gly Lys
    530                 535
```

<210> SEQ ID NO 324
<211> LENGTH: 543
<212> TYPE: PRT

<213> ORGANISM: Artificial Sequence
<220> FEATURE:
<223> OTHER INFORMATION: synthetic

<400> SEQUENCE: 324

```
Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Ala Val Ala Asp Ser
    50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Ser Gly Ser Glu Lys Asn Ser Lys
            100                 105                 110

Ile Tyr Cys Pro Thr Ile Asp Leu Tyr Asn Trp Thr Ala Pro Leu Glu
        115                 120                 125

Trp Phe Lys Asn Cys Gln Ala Leu Gln Gly Ser Arg Tyr Arg Ala His
    130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu Gln Gly Phe Ser Leu
            180                 185                 190

Phe Pro Val Ile Gly Ala Pro Ala Gln Asn Glu Ile Lys Glu Val Glu
        195                 200                 205

Ile Gly Lys Asn Ala Asn Leu Thr Cys Ser Ala Cys Phe Gly Lys Gly
    210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Gly Gln Asn Gln
                245                 250                 255

Ser Phe Ser Asn Gly Leu Ala Cys Leu Asp Met Val Leu Arg Ile Ala
            260                 265                 270

Asp Val Lys Glu Glu Asp Leu Leu Leu Gln Tyr Asp Cys Leu Ala Leu
        275                 280                 285

Asn Leu His Gly Leu Arg Arg His Thr Val Arg Leu Ser Arg Lys Asn
    290                 295                 300

Pro Ile Asp His His Ser Glu Pro Arg Gly Pro Thr Ile Lys Pro Cys
305                 310                 315                 320

Pro Pro Cys Lys Cys Pro Ala Pro Asn Leu Leu Gly Gly Pro Ser Val
                325                 330                 335

Phe Ile Phe Pro Pro Lys Ile Lys Asp Val Leu Met Ile Ser Leu Ser
            340                 345                 350

Pro Ile Val Thr Cys Val Val Asp Val Ser Glu Asp Asp Pro Asp
        355                 360                 365

Val Gln Ile Ser Trp Phe Val Asn Asn Val Glu Val His Thr Ala Gln
    370                 375                 380

Thr Gln Thr His Arg Glu Asp Tyr Asn Ser Thr Leu Arg Val Val Ser
```

```
                385                 390                 395                 400
        Ala Leu Pro Ile Gln His Gln Asp Trp Met Ser Gly Lys Glu Phe Lys
                        405                 410                 415

Cys Lys Val Asn Asn Lys Asp Leu Pro Ala Pro Ile Glu Arg Thr Ile
                        420                 425                 430

Ser Lys Pro Lys Gly Ser Val Arg Ala Pro Gln Val Tyr Val Leu Pro
                        435                 440                 445

Pro Pro Glu Glu Glu Met Thr Lys Lys Gln Val Thr Leu Thr Cys Met
                    450                 455                 460

Val Thr Asp Phe Met Pro Glu Asp Ile Tyr Val Glu Trp Thr Asn Asn
        465                 470                 475                 480

Gly Lys Thr Glu Leu Asn Tyr Lys Asn Thr Glu Pro Val Leu Asp Ser
                        485                 490                 495

Asp Gly Ser Tyr Phe Met Tyr Ser Lys Leu Arg Val Glu Lys Lys Asn
                        500                 505                 510

Trp Val Glu Arg Asn Ser Tyr Ser Cys Ser Val Val His Glu Gly Leu
                        515                 520                 525

His Asn His His Thr Thr Lys Ser Phe Ser Arg Thr Pro Gly Lys
                        530                 535                 540

<210> SEQ ID NO 325
<211> LENGTH: 884
<212> TYPE: PRT
<213> ORGANISM: Artificial Sequence
<220> FEATURE:
<223> OTHER INFORMATION: synthetic

<400> SEQUENCE: 325

Lys Phe Ser Lys Gln Ser Trp Gly Leu Glu Asn Glu Ala Leu Ile Val
        1               5                   10                  15

Arg Cys Pro Arg Gln Gly Lys Pro Ser Tyr Thr Val Asp Trp Tyr Tyr
                        20                  25                  30

Ser Gln Thr Asn Lys Ser Ile Pro Thr Gln Glu Arg Asn Arg Val Phe
                    35                  40                  45

Ala Ser Gly Gln Leu Leu Lys Phe Leu Pro Ala Ala Val Ala Asp Ser
        50                  55                  60

Gly Ile Tyr Thr Cys Ile Val Arg Ser Pro Thr Phe Asn Arg Thr Gly
        65                  70                  75                  80

Tyr Ala Asn Val Thr Ile Tyr Lys Lys Gln Ser Asp Cys Asn Val Pro
                        85                  90                  95

Asp Tyr Leu Met Tyr Ser Thr Val Ser Gly Ser Glu Lys Asn Ser Lys
                        100                 105                 110

Ile Tyr Cys Pro Thr Ile Asp Leu Tyr Asn Trp Thr Ala Pro Leu Glu
                        115                 120                 125

Trp Phe Lys Asn Cys Gln Ala Leu Gln Gly Ser Arg Tyr Arg Ala His
                130                 135                 140

Lys Ser Phe Leu Val Ile Asp Asn Val Met Thr Glu Asp Ala Gly Asp
        145                 150                 155                 160

Tyr Thr Cys Lys Phe Ile His Asn Glu Asn Gly Ala Asn Tyr Ser Val
                        165                 170                 175

Thr Ala Thr Arg Ser Phe Thr Val Lys Asp Glu Gln Gly Phe Ser Leu
                        180                 185                 190

Phe Pro Val Ile Gly Ala Pro Ala Gln Asn Glu Ile Lys Glu Val Glu
                        195                 200                 205

Ile Gly Lys Asn Ala Asn Leu Thr Cys Ser Ala Cys Phe Gly Lys Gly
```

```
            210                 215                 220
Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Gly Gln Asn Gln
                245                 250                 255

Ser Phe Ser Asn Gly Leu Ala Cys Leu Asp Met Val Leu Arg Ile Ala
                260                 265                 270

Asp Val Lys Glu Glu Asp Leu Leu Leu Gln Tyr Asp Cys Leu Ala Leu
            275                 280                 285

Asn Leu His Gly Leu Arg Arg His Thr Val Arg Leu Ser Arg Lys Asn
            290                 295                 300

Pro Ile Asp His His Ser Ser Glu Arg Cys Asp Asp Trp Gly Leu Asp
305                 310                 315                 320

Thr Met Arg Gln Ile Gln Val Phe Glu Asp Glu Pro Ala Arg Ile Lys
                325                 330                 335

Cys Pro Leu Phe Glu His Phe Leu Lys Phe Asn Tyr Ser Thr Ala His
                340                 345                 350

Ser Ala Gly Leu Thr Leu Ile Trp Tyr Trp Thr Arg Gln Asp Arg Asp
            355                 360                 365

Leu Glu Glu Pro Ile Asn Phe Arg Leu Pro Glu Asn Arg Ile Ser Lys
            370                 375                 380

Glu Lys Asp Val Leu Trp Phe Arg Pro Thr Leu Leu Asn Asp Thr Gly
385                 390                 395                 400

Asn Tyr Thr Cys Met Leu Arg Asn Thr Thr Tyr Cys Ser Lys Val Ala
                405                 410                 415

Phe Pro Leu Glu Val Val Gln Lys Asp Ser Cys Phe Asn Ser Pro Met
                420                 425                 430

Lys Leu Pro Val His Lys Leu Tyr Ile Glu Tyr Gly Ile Gln Arg Ile
            435                 440                 445

Thr Cys Pro Asn Val Asp Gly Tyr Phe Pro Ser Ser Val Lys Pro Thr
            450                 455                 460

Ile Thr Trp Tyr Met Gly Cys Tyr Lys Ile Gln Asn Phe Asn Asn Val
465                 470                 475                 480

Ile Pro Glu Gly Met Asn Leu Ser Phe Leu Ile Ala Leu Ile Ser Asn
                485                 490                 495

Asn Gly Asn Tyr Thr Cys Val Val Thr Tyr Pro Glu Asn Gly Arg Thr
                500                 505                 510

Phe His Leu Thr Arg Thr Leu Thr Val Lys Val Val Gly Ser Pro Lys
            515                 520                 525

Asn Ala Val Pro Pro Val Ile His Ser Pro Asn Asp His Val Val Tyr
            530                 535                 540

Glu Lys Glu Pro Gly Glu Leu Leu Ile Pro Cys Thr Val Tyr Phe
545                 550                 555                 560

Ser Phe Leu Met Asp Ser Arg Asn Glu Val Trp Trp Thr Ile Asp Gly
                565                 570                 575

Lys Lys Pro Asp Asp Ile Thr Ile Asp Val Thr Ile Asn Glu Ser Ile
            580                 585                 590

Ser His Ser Arg Thr Glu Asp Glu Thr Arg Thr Gln Ile Leu Ser Ile
            595                 600                 605

Lys Lys Val Thr Ser Glu Asp Leu Lys Arg Ser Tyr Val Cys His Ala
            610                 615                 620

Arg Ser Ala Lys Gly Glu Val Ala Lys Ala Ala Lys Val Lys Gln Lys
625                 630                 635                 640
```

```
Val Pro Ala Pro Arg Tyr Thr Val Glu Ser Gly Glu Pro Arg Gly Pro
                645                 650                 655

Thr Ile Lys Pro Cys Pro Pro Cys Lys Cys Pro Ala Pro Asn Leu Leu
            660                 665                 670

Gly Gly Pro Ser Val Phe Ile Phe Pro Pro Lys Ile Lys Asp Val Leu
        675                 680                 685

Met Ile Ser Leu Ser Pro Ile Val Thr Cys Val Val Val Asp Val Ser
    690                 695                 700

Glu Asp Asp Pro Asp Val Gln Ile Ser Trp Phe Val Asn Asn Val Glu
705                 710                 715                 720

Val His Thr Ala Gln Thr Gln Thr His Arg Glu Asp Tyr Asn Ser Thr
                725                 730                 735

Leu Arg Val Val Ser Ala Leu Pro Ile Gln His Gln Asp Trp Met Ser
            740                 745                 750

Gly Lys Glu Phe Lys Cys Lys Val Asn Asn Lys Asp Leu Pro Ala Pro
        755                 760                 765

Ile Glu Arg Thr Ile Ser Lys Pro Lys Gly Ser Val Arg Ala Pro Gln
    770                 775                 780

Val Tyr Val Leu Pro Pro Glu Glu Glu Met Thr Lys Lys Gln Val
785                 790                 795                 800

Thr Leu Thr Cys Met Val Thr Asp Phe Met Pro Glu Asp Ile Tyr Val
                805                 810                 815

Glu Trp Thr Asn Asn Gly Lys Thr Glu Leu Asn Tyr Lys Asn Thr Glu
            820                 825                 830

Pro Val Leu Asp Ser Asp Gly Ser Tyr Phe Met Tyr Ser Lys Leu Arg
        835                 840                 845

Val Glu Lys Lys Asn Trp Val Glu Arg Asn Ser Tyr Ser Cys Ser Val
    850                 855                 860

Val His Glu Gly Leu His Asn His His Thr Thr Lys Ser Phe Ser Arg
865                 870                 875                 880

Thr Pro Gly Lys

<210> SEQ ID NO 326
<211> LENGTH: 880
<212> TYPE: PRT
<213> ORGANISM: Artificial Sequence
<220> FEATURE:
<223> OTHER INFORMATION: synthetic

<400> SEQUENCE: 326

Ser Lys Ser Ser Trp Gly Leu Glu Asn Glu Ala Leu Ile Val Arg Cys
1               5                   10                  15

Pro Gln Arg Gly Arg Ser Thr Tyr Pro Val Glu Trp Tyr Tyr Ser Asp
            20                  25                  30

Thr Asn Glu Ser Ile Pro Thr Gln Lys Arg Asn Arg Ile Phe Val Ser
        35                  40                  45

Arg Asp Arg Leu Lys Phe Leu Pro Ala Arg Val Glu Asp Ser Gly Ile
    50                  55                  60

Tyr Ala Cys Val Ile Arg Ser Pro Asn Leu Asn Lys Thr Gly Tyr Leu
65                  70                  75                  80

Asn Val Thr Ile His Lys Lys Pro Pro Ser Cys Asn Ile Pro Asp Tyr
                85                  90                  95

Leu Met Tyr Ser Thr Val Arg Gly Ser Asp Lys Asn Phe Lys Ile Thr
            100                 105                 110
```

-continued

Cys Pro Thr Ile Asp Leu Tyr Asn Trp Thr Ala Pro Val Gln Trp Phe
            115                 120                 125

Lys Asn Cys Lys Ala Leu Gln Glu Pro Arg Phe Arg Ala His Arg Ser
        130                 135                 140

Tyr Leu Phe Ile Asp Asn Val Thr His Asp Asp Glu Gly Asp Tyr Thr
145                 150                 155                 160

Cys Gln Phe Thr His Ala Glu Asn Gly Thr Asn Tyr Ile Val Thr Ala
                165                 170                 175

Thr Arg Ser Phe Thr Val Glu Glu Lys Gly Phe Ser Met Phe Pro Val
            180                 185                 190

Ile Thr Asn Pro Pro Tyr Asn His Thr Met Glu Val Glu Ile Gly Lys
        195                 200                 205

Pro Ala Ser Ile Ala Cys Ser Ala Cys Phe Gly Lys Gly Ser His Phe
    210                 215                 220

Leu Ala Asp Val Leu Trp Gln Ile Asn Lys Thr Val Val Gly Asn Phe
225                 230                 235                 240

Gly Glu Ala Arg Ile Gln Glu Glu Gly Arg Asn Glu Ser Ser Ser
                245                 250                 255

Asn Asp Met Asp Cys Leu Thr Ser Val Leu Arg Ile Thr Gly Val Thr
                260                 265                 270

Glu Lys Asp Leu Ser Leu Glu Tyr Asp Cys Leu Ala Leu Asn Leu His
            275                 280                 285

Gly Met Ile Arg His Thr Ile Arg Leu Arg Arg Lys Gln Pro Ile Asp
        290                 295                 300

His Arg Ser Glu Arg Cys Asp Asp Trp Gly Leu Asp Thr Met Arg Gln
305                 310                 315                 320

Ile Gln Val Phe Glu Asp Glu Pro Ala Arg Ile Lys Cys Pro Leu Phe
                325                 330                 335

Glu His Phe Leu Lys Tyr Asn Tyr Ser Thr Ala His Ser Ser Gly Leu
            340                 345                 350

Thr Leu Ile Trp Tyr Trp Thr Arg Gln Asp Arg Asp Leu Glu Glu Pro
        355                 360                 365

Ile Asn Phe Arg Leu Pro Glu Asn Arg Ile Ser Lys Glu Lys Asp Val
370                 375                 380

Leu Trp Phe Arg Pro Thr Leu Leu Asn Asp Thr Gly Asn Tyr Thr Cys
385                 390                 395                 400

Met Leu Arg Asn Thr Thr Tyr Cys Ser Lys Val Ala Phe Pro Leu Glu
                405                 410                 415

Val Val Gln Lys Asp Ser Cys Phe Asn Ser Ala Met Arg Phe Pro Val
            420                 425                 430

His Lys Met Tyr Ile Glu His Gly Ile His Lys Ile Thr Cys Pro Asn
        435                 440                 445

Val Asp Gly Tyr Phe Pro Ser Ser Val Lys Pro Ser Val Thr Trp Tyr
    450                 455                 460

Lys Gly Cys Thr Glu Ile Val Asp Phe His Asn Val Leu Pro Glu Gly
465                 470                 475                 480

Met Asn Leu Ser Phe Phe Ile Pro Leu Val Ser Asn Asn Gly Asn Tyr
                485                 490                 495

Thr Cys Val Val Thr Tyr Pro Glu Asn Gly Arg Leu Phe His Leu Thr
            500                 505                 510

Arg Thr Val Thr Val Lys Val Val Gly Ser Pro Lys Asp Ala Leu Pro
        515                 520                 525

Pro Gln Ile Tyr Ser Pro Asn Asp Arg Val Val Tyr Glu Lys Glu Pro

```
                    530                 535                 540
Gly Glu Glu Leu Val Ile Pro Cys Lys Val Tyr Phe Ser Phe Ile Met
545                 550                 555                 560

Asp Ser His Asn Glu Val Trp Trp Thr Ile Asp Gly Lys Lys Pro Asp
                565                 570                 575

Asp Val Thr Val Asp Ile Thr Ile Asn Glu Ser Val Ser Tyr Ser Ser
                580                 585                 590

Thr Glu Asp Glu Thr Arg Thr Gln Ile Leu Ser Ile Lys Lys Val Thr
                595                 600                 605

Pro Glu Asp Leu Arg Arg Asn Tyr Val Cys His Ala Arg Asn Thr Lys
                610                 615                 620

Gly Glu Ala Glu Gln Ala Ala Lys Val Lys Gln Lys Val Ile Pro Pro
625                 630                 635                 640

Arg Tyr Thr Val Glu Ser Gly Glu Pro Arg Gly Pro Thr Ile Lys Pro
                645                 650                 655

Cys Pro Pro Cys Lys Cys Pro Ala Pro Asn Leu Leu Gly Gly Pro Ser
                660                 665                 670

Val Phe Ile Phe Pro Pro Lys Ile Lys Asp Val Leu Met Ile Ser Leu
                675                 680                 685

Ser Pro Ile Val Thr Cys Val Val Asp Val Ser Glu Asp Asp Pro
                690                 695                 700

Asp Val Gln Ile Ser Trp Phe Val Asn Asn Val Glu Val His Thr Ala
705                 710                 715                 720

Gln Thr Gln Thr His Arg Glu Asp Tyr Asn Ser Thr Leu Arg Val Val
                725                 730                 735

Ser Ala Leu Pro Ile Gln His Gln Asp Trp Met Ser Gly Lys Glu Phe
                740                 745                 750

Lys Cys Lys Val Asn Asn Lys Asp Leu Pro Ala Pro Ile Glu Arg Thr
                755                 760                 765

Ile Ser Lys Pro Lys Gly Ser Val Arg Ala Pro Gln Val Tyr Val Leu
                770                 775                 780

Pro Pro Pro Glu Glu Glu Met Thr Lys Lys Gln Val Thr Leu Thr Cys
785                 790                 795                 800

Met Val Thr Asp Phe Met Pro Glu Asp Ile Tyr Val Glu Trp Thr Asn
                805                 810                 815

Asn Gly Lys Thr Glu Leu Asn Tyr Lys Asn Thr Glu Pro Val Leu Asp
                820                 825                 830

Ser Asp Gly Ser Tyr Phe Met Tyr Ser Lys Leu Arg Val Glu Lys Lys
                835                 840                 845

Asn Trp Val Glu Arg Asn Ser Tyr Ser Cys Ser Val Val His Glu Gly
850                 855                 860

Leu His Asn His His Thr Thr Lys Ser Phe Ser Arg Thr Pro Gly Lys
865                 870                 875                 880

<210> SEQ ID NO 327
<211> LENGTH: 310
<212> TYPE: PRT
<213> ORGANISM: Artificial Sequence
<220> FEATURE:
<223> OTHER INFORMATION: synthetic

<400> SEQUENCE: 327

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
```

```
            20                  25                  30
Ser Gln Thr Asn Lys Ser Ile Pro Thr Gln Glu Arg Asn Arg Val Phe
            35                  40                  45

Ala Ser Gly Gln Leu Leu Lys Phe Leu Pro Ala Ala Val Ala Asp Ser
    50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Ser Gly Ser Glu Lys Asn Ser Lys
            100                 105                 110

Ile Tyr Cys Pro Thr Ile Asp Leu Tyr Asn Trp Thr Ala Pro Leu Glu
            115                 120                 125

Trp Phe Lys Asn Cys Gln Ala Leu Gln Gly Ser Arg Tyr Arg Ala His
            130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu Gln Gly Phe Ser Leu
            180                 185                 190

Phe Pro Val Ile Gly Ala Pro Ala Gln Asn Glu Ile Lys Glu Val Glu
            195                 200                 205

Ile Gly Lys Asn Ala Asn Leu Thr Cys Ser Ala Cys Phe Gly Lys Gly
        210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Gly Gln Asn Gln
                245                 250                 255

Ser Phe Ser Asn Gly Leu Ala Cys Leu Asp Met Val Leu Arg Ile Ala
            260                 265                 270

Asp Val Lys Glu Glu Asp Leu Leu Leu Gln Tyr Asp Cys Leu Ala Leu
            275                 280                 285

Asn Leu His Gly Leu Arg Arg His Thr Val Arg Leu Ser Arg Lys Asn
            290                 295                 300

Pro Ile Asp His His Ser
305                 310

<210> SEQ ID NO 328
<211> LENGTH: 306
<212> TYPE: PRT
<213> ORGANISM: Artificial Sequence
<220> FEATURE:
<223> OTHER INFORMATION: synthetic

<400> SEQUENCE: 328

Ser Lys Ser Ser Trp Gly Leu Glu Asn Glu Ala Leu Ile Val Arg Cys
1               5                   10                  15

Pro Gln Arg Gly Arg Ser Thr Tyr Pro Val Glu Trp Tyr Tyr Ser Asp
            20                  25                  30

Thr Asn Glu Ser Ile Pro Thr Gln Lys Arg Asn Arg Ile Phe Val Ser
            35                  40                  45

Arg Asp Arg Leu Lys Phe Leu Pro Ala Arg Val Glu Asp Ser Gly Ile
            50                  55                  60

Tyr Ala Cys Val Ile Arg Ser Pro Asn Leu Asn Lys Thr Gly Tyr Leu
```

```
            65                  70                  75                  80
Asn Val Thr Ile His Lys Lys Pro Pro Ser Cys Asn Ile Pro Asp Tyr
                        85                  90                  95

Leu Met Tyr Ser Thr Val Arg Gly Ser Asp Lys Asn Phe Lys Ile Thr
                        100                 105                 110

Cys Pro Thr Ile Asp Leu Tyr Asn Trp Thr Ala Pro Val Gln Trp Phe
                        115                 120                 125

Lys Asn Cys Lys Ala Leu Gln Glu Pro Arg Phe Arg Ala His Arg Ser
                        130                 135                 140

Tyr Leu Phe Ile Asp Asn Val Thr His Asp Glu Gly Asp Tyr Thr
145                     150                 155                 160

Cys Gln Phe Thr His Ala Glu Asn Gly Thr Asn Tyr Ile Val Thr Ala
                        165                 170                 175

Thr Arg Ser Phe Thr Val Glu Glu Lys Gly Phe Ser Met Phe Pro Val
                        180                 185                 190

Ile Thr Asn Pro Pro Tyr Asn His Thr Met Glu Val Glu Ile Gly Lys
                        195                 200                 205

Pro Ala Ser Ile Ala Cys Ser Ala Cys Phe Gly Lys Gly Ser His Phe
                        210                 215                 220

Leu Ala Asp Val Leu Trp Gln Ile Asn Lys Thr Val Val Gly Asn Phe
225                     230                 235                 240

Gly Glu Ala Arg Ile Gln Glu Glu Gly Arg Asn Glu Ser Ser Ser
                        245                 250                 255

Asn Asp Met Asp Cys Leu Thr Ser Val Leu Arg Ile Thr Gly Val Thr
                        260                 265                 270

Glu Lys Asp Leu Ser Leu Glu Tyr Asp Cys Leu Ala Leu Asn Leu His
                        275                 280                 285

Gly Met Ile Arg His Thr Ile Arg Leu Arg Arg Lys Gln Pro Ile Asp
                        290                 295                 300

His Arg
305

<210> SEQ ID NO 329
<211> LENGTH: 339
<212> TYPE: PRT
<213> ORGANISM: Artificial Sequence
<220> FEATURE:
<223> OTHER INFORMATION: synthetic

<400> SEQUENCE: 329

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
                        20                  25                  30

Phe Leu Lys Phe Asn Tyr Ser Thr Ala His Ser Ala Gly Leu Thr Leu
                        35                  40                  45

Ile Trp Tyr Trp Thr Arg Gln Asp Arg Asp Leu Glu Glu Pro Ile Asn
                        50                  55                  60

Phe Arg Leu Pro Glu Asn Arg Ile Ser Lys Glu Lys Asp Val Leu Trp
65                      70                  75                  80

Phe Arg Pro Thr Leu Leu Asn Asp Thr Gly Asn Tyr Thr Cys Met Leu
                        85                  90                  95

Arg Asn Thr Thr Tyr Cys Ser Lys Val Ala Phe Pro Leu Glu Val Val
                        100                 105                 110

Gln Lys Asp Ser Cys Phe Asn Ser Pro Met Lys Leu Pro Val His Lys
```

```
                115                 120                 125
Leu Tyr Ile Glu Tyr Gly Ile Gln Arg Ile Thr Cys Pro Asn Val Asp
130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Leu Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro Lys Asn Ala Val Pro Pro Val
    210                 215                 220

Ile His Ser Pro Asn Asp His Val Val Tyr Lys Glu Pro Gly Glu
225                 230                 235                 240

Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
            260                 265                 270

Thr Ile Asp Val Thr Ile Asn Glu Ser Ile Ser His Ser Arg Thr Glu
        275                 280                 285

Asp Glu Thr Arg Thr Gln Ile Leu Ser Ile Lys Lys Val Thr Ser Glu
    290                 295                 300

Asp Leu Lys Arg Ser Tyr Val Cys His Ala Arg Ser Ala Lys Gly Glu
305                 310                 315                 320

Val Ala Lys Ala Ala Lys Val Lys Gln Lys Val Pro Ala Pro Arg Tyr
                325                 330                 335

Thr Val Glu

<210> SEQ ID NO 330
<211> LENGTH: 339
<212> TYPE: PRT
<213> ORGANISM: Artificial Sequence
<220> FEATURE:
<223> OTHER INFORMATION: synthetic

<400> SEQUENCE: 330

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
                20                  25                  30

Phe Leu Lys Tyr Asn Tyr Ser Thr Ala His Ser Ser Gly Leu Thr Leu
            35                  40                  45

Ile Trp Tyr Trp Thr Arg Gln Asp Arg Asp Leu Glu Glu Pro Ile Asn
        50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Ala Met Arg Phe Pro Val His Lys
        115                 120                 125

Met Tyr Ile Glu His Gly Ile His Lys Ile Thr Cys Pro Asn Val Asp
    130                 135                 140
```

Gly Tyr Phe Pro Ser Ser Val Lys Pro Ser Val Thr Trp Tyr Lys Gly
145                 150                 155                 160

Cys Thr Glu Ile Val Asp Phe His Asn Val Leu Pro Glu Gly Met Asn
            165                 170                 175

Leu Ser Phe Phe Ile Pro Leu Val Ser Asn Asn Gly Asn Tyr Thr Cys
        180                 185                 190

Val Val Thr Tyr Pro Glu Asn Gly Arg Leu Phe His Leu Thr Arg Thr
    195                 200                 205

Val Thr Val Lys Val Val Gly Ser Pro Lys Asp Ala Leu Pro Pro Gln
210                 215                 220

Ile Tyr Ser Pro Asn Asp Arg Val Val Tyr Glu Lys Glu Pro Gly Glu
225                 230                 235                 240

Glu Leu Val Ile Pro Cys Lys Val Tyr Phe Ser Phe Ile Met Asp Ser
                245                 250                 255

His Asn Glu Val Trp Trp Thr Ile Asp Gly Lys Lys Pro Asp Asp Val
            260                 265                 270

Thr Val Asp Ile Thr Ile Asn Glu Ser Val Ser Tyr Ser Ser Thr Glu
        275                 280                 285

Asp Glu Thr Arg Thr Gln Ile Leu Ser Ile Lys Lys Val Thr Pro Glu
290                 295                 300

Asp Leu Arg Arg Asn Tyr Val Cys His Ala Arg Asn Thr Lys Gly Glu
305                 310                 315                 320

Ala Glu Gln Ala Ala Lys Val Lys Gln Lys Val Ile Pro Pro Arg Tyr
                325                 330                 335

Thr Val Glu

<210> SEQ ID NO 331
<211> LENGTH: 227
<212> TYPE: PRT
<213> ORGANISM: Artificial Sequence
<220> FEATURE:
<223> OTHER INFORMATION: synthetic

<400> SEQUENCE: 331

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                  170              175

Val Leu Asp Ser Asp Gly Ser Phe Phe Leu Tyr Ser Lys Leu Thr Val
           180                  185               190

Asp Lys Ser Arg Trp Gln Gln Gly Asn Val Phe Ser Cys Ser Val Met
       195                  200              205

His Glu Ala Leu His Asn His Tyr Thr Gln Lys Ser Leu Ser Leu Ser
210                 215                  220

Pro Gly Lys
225

<210> SEQ ID NO 332
<211> LENGTH: 233
<212> TYPE: PRT
<213> ORGANISM: Artificial Sequence
<220> FEATURE:
<223> OTHER INFORMATION: synthetic

<400> SEQUENCE: 332

Glu Pro Arg Gly Pro Thr Ile Lys Pro Cys Pro Pro Cys Lys Cys Pro
1               5                  10               15

Ala Pro Asn Leu Leu Gly Gly Pro Ser Val Phe Ile Phe Pro Pro Lys
        20                 25                30

Ile Lys Asp Val Leu Met Ile Ser Leu Ser Pro Ile Val Thr Cys Val
       35                 40                45

Val Val Asp Val Ser Glu Asp Asp Pro Asp Val Gln Ile Ser Trp Phe
 50                55                60

Val Asn Asn Val Glu Val His Thr Ala Gln Thr Gln Thr His Arg Glu
65                70               75               80

Asp Tyr Asn Ser Thr Leu Arg Val Val Ser Ala Leu Pro Ile Gln His
        85                 90                95

Gln Asp Trp Met Ser Gly Lys Glu Phe Lys Cys Lys Val Asn Asn Lys
       100                105              110

Asp Leu Pro Ala Pro Ile Glu Arg Thr Ile Ser Lys Pro Lys Gly Ser
      115               120              125

Val Arg Ala Pro Gln Val Tyr Val Leu Pro Pro Pro Glu Glu Glu Met
   130                135                140

Thr Lys Lys Gln Val Thr Leu Thr Cys Met Val Thr Asp Phe Met Pro
145                150               155              160

Glu Asp Ile Tyr Val Glu Trp Thr Asn Asn Gly Lys Thr Glu Leu Asn
              165                170              175

Tyr Lys Asn Thr Glu Pro Val Leu Asp Ser Asp Gly Ser Tyr Phe Met
       180                185              190

Tyr Ser Lys Leu Arg Val Glu Lys Lys Asn Trp Val Glu Arg Asn Ser
      195               200              205

Tyr Ser Cys Ser Val Val His Glu Gly Leu His Asn His His Thr Thr
   210                215                220

Lys Ser Phe Ser Arg Thr Pro Gly Lys
225                230

<210> SEQ ID NO 333
<211> LENGTH: 167
<212> TYPE: PRT
<213> ORGANISM: Artificial Sequence
<220> FEATURE:
<223> OTHER INFORMATION: synthetic

<400> SEQUENCE: 333

```
Ser Ile Thr Gly Ile Ser Pro Ile Thr Glu Ser Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Lys Lys Lys Asp Lys Val
        35                  40                  45

Leu Leu Ser Tyr Tyr Glu Ser Gln His Pro Ser Ser Glu Ser Gly Asp
50                  55                  60

Gly Val Asp Gly Lys Met Leu Met Val Thr Leu Ser Pro Thr Lys Asp
65                  70                  75                  80

Phe Trp Leu Gln Ala Asn Asn Lys Glu His Ser Val Glu Leu His Lys
                85                  90                  95

Cys Glu Lys Pro Leu Pro Asp Gln Ala Phe Phe Val Leu His Asn Arg
                100                 105                 110

Ser Phe Asn Cys Val Ser Phe Glu Cys Lys Thr Asp Pro Gly Val Phe
            115                 120                 125

Ile Gly Val Lys Asp Asn His Leu Ala Leu Ile Lys Val Asp Tyr Ser
        130                 135                 140

Glu Asn Leu Gly Ser Glu Asn Ile Leu Phe Lys Leu Ser Glu Ile Leu
145                 150                 155                 160

Glu His His His His His His
                165

<210> SEQ ID NO 334
<211> LENGTH: 167
<212> TYPE: PRT
<213> ORGANISM: Artificial Sequence
<220> FEATURE:
<223> OTHER INFORMATION: aa 1-159: M.fascicularis IL-33 (S112-E269 of
      EHH57404.1 with an extra I after E269)
      aa 160-161: linker
      aa 162-167: hexahistidine tag

<400> SEQUENCE: 334

Ser Ile Thr Gly Ile Ser Pro Ile Thr Glu Ser Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Lys Lys Lys Asp Lys Val
        35                  40                  45

Leu Leu Ser Tyr Tyr Glu Ser Gln His Pro Ser Ser Glu Ser Gly Asp
50                  55                  60

Gly Val Asp Gly Lys Met Leu Met Val Thr Leu Ser Pro Thr Lys Asp
65                  70                  75                  80

Phe Trp Leu Gln Ala Asn Asn Lys Glu His Ser Val Glu Leu His Lys
                85                  90                  95

Cys Glu Lys Pro Leu Pro Asp Gln Ala Phe Phe Val Leu His Asn Arg
                100                 105                 110

Ser Phe Asn Cys Val Ser Phe Glu Cys Lys Thr Asp Pro Gly Val Phe
            115                 120                 125

Ile Gly Val Lys Asp Asn His Leu Ala Leu Ile Lys Val Asp Tyr Ser
        130                 135                 140

Glu Asn Leu Gly Ser Glu Asn Ile Leu Phe Lys Leu Ser Glu Ile Leu
145                 150                 155                 160

Glu His His His His His His
                165
```

<210> SEQ ID NO 335
<211> LENGTH: 876
<212> TYPE: PRT
<213> ORGANISM: Artificial Sequence
<220> FEATURE:
<223> OTHER INFORMATION: aa 1-310: Human ST2 (K19-S328 of NP_057316.3)
    aa 311-649: Human IL1RacP (S21-E359 of Q9NPH3)
    aa 650-876: hFc tag (D104-K330 of P01857)

<400> SEQUENCE: 335

```
Lys Phe Ser Lys Gln Ser Trp Gly Leu Glu Asn Glu Ala Leu Ile Val
 1               5                  10                  15

Arg Cys Pro Arg Gln Gly Lys Pro Ser Tyr Thr Val Asp Trp Tyr Tyr
             20                  25                  30

Ser Gln Thr Asn Lys Ser Ile Pro Thr Gln Glu Arg Asn Arg Val Phe
         35                  40                  45

Ala Ser Gly Gln Leu Leu Lys Phe Leu Pro Ala Ala Val Ala Asp Ser
     50                  55                  60

Gly Ile Tyr Thr Cys Ile Val Arg Ser Pro Thr Phe Asn Arg Thr Gly
 65                  70                  75                  80

Tyr Ala Asn Val Thr Ile Tyr Lys Lys Gln Ser Asp Cys Asn Val Pro
                 85                  90                  95

Asp Tyr Leu Met Tyr Ser Thr Val Ser Gly Ser Glu Lys Asn Ser Lys
            100                 105                 110

Ile Tyr Cys Pro Thr Ile Asp Leu Tyr Asn Trp Thr Ala Pro Leu Glu
        115                 120                 125

Trp Phe Lys Asn Cys Gln Ala Leu Gln Gly Ser Arg Tyr Arg Ala His
    130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu Gln Gly Phe Ser Leu
            180                 185                 190

Phe Pro Val Ile Gly Ala Pro Ala Gln Asn Glu Ile Lys Glu Val Glu
        195                 200                 205

Ile Gly Lys Asn Ala Asn Leu Thr Cys Ser Ala Cys Phe Gly Lys Gly
    210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Glu Gly Gln Asn Gln
                245                 250                 255

Ser Phe Ser Asn Gly Leu Ala Cys Leu Asp Met Val Leu Arg Ile Ala
            260                 265                 270

Asp Val Lys Glu Glu Asp Leu Leu Leu Gln Tyr Asp Cys Leu Ala Leu
        275                 280                 285

Asn Leu His Gly Leu Arg Arg His Thr Val Arg Leu Ser Arg Lys Asn
    290                 295                 300

Pro Ile Asp His His Ser Ser Glu Arg Cys Asp Asp Trp Gly Leu Asp
305                 310                 315                 320

Thr Met Arg Gln Ile Gln Val Phe Glu Asp Glu Pro Ala Arg Ile Lys
                325                 330                 335

Cys Pro Leu Phe Glu His Phe Leu Lys Phe Asn Tyr Ser Thr Ala His
            340                 345                 350

Ser Ala Gly Leu Thr Leu Ile Trp Tyr Trp Thr Arg Gln Asp Arg Asp
        355                 360                 365
```

```
Leu Glu Glu Pro Ile Asn Phe Arg Leu Pro Glu Asn Arg Ile Ser Lys
370                 375                 380

Glu Lys Asp Val Leu Trp Phe Arg Pro Thr Leu Leu Asn Asp Thr Gly
385                 390                 395                 400

Asn Tyr Thr Cys Met Leu Arg Asn Thr Thr Tyr Cys Ser Lys Val Ala
                405                 410                 415

Phe Pro Leu Glu Val Val Gln Lys Asp Ser Cys Phe Asn Ser Pro Met
                420                 425                 430

Lys Leu Pro Val His Lys Leu Tyr Ile Glu Tyr Gly Ile Gln Arg Ile
                435                 440                 445

Thr Cys Pro Asn Val Asp Gly Tyr Phe Pro Ser Ser Val Lys Pro Thr
450                 455                 460

Ile Thr Trp Tyr Met Gly Cys Tyr Lys Ile Gln Asn Phe Asn Asn Val
465                 470                 475                 480

Ile Pro Glu Gly Met Asn Leu Ser Phe Leu Ile Ala Leu Ile Ser Asn
                485                 490                 495

Asn Gly Asn Tyr Thr Cys Val Val Thr Tyr Pro Glu Asn Gly Arg Thr
                500                 505                 510

Phe His Leu Thr Arg Thr Leu Thr Val Lys Val Val Gly Ser Pro Lys
                515                 520                 525

Asn Ala Val Pro Pro Val Ile His Ser Pro Asn Asp His Val Val Tyr
530                 535                 540

Glu Lys Glu Pro Gly Glu Glu Leu Leu Ile Pro Cys Thr Val Tyr Phe
545                 550                 555                 560

Ser Phe Leu Met Asp Ser Arg Asn Glu Val Trp Trp Thr Ile Asp Gly
                565                 570                 575

Lys Lys Pro Asp Asp Ile Thr Ile Asp Val Thr Ile Asn Glu Ser Ile
                580                 585                 590

Ser His Ser Arg Thr Glu Asp Glu Thr Arg Thr Gln Ile Leu Ser Ile
                595                 600                 605

Lys Lys Val Thr Ser Glu Asp Leu Lys Arg Ser Tyr Val Cys His Ala
                610                 615                 620

Arg Ser Ala Lys Gly Glu Val Ala Lys Ala Ala Lys Val Lys Gln Lys
625                 630                 635                 640

Val Pro Ala Pro Arg Tyr Thr Val Glu Asp Lys Thr His Thr Cys Pro
                645                 650                 655

Pro Cys Pro Ala Pro Glu Leu Leu Gly Gly Pro Ser Val Phe Leu Phe
                660                 665                 670

Pro Pro Lys Pro Lys Asp Thr Leu Met Ile Ser Arg Thr Pro Glu Val
                675                 680                 685

Thr Cys Val Val Val Asp Val Ser His Glu Asp Pro Glu Val Lys Phe
690                 695                 700

Asn Trp Tyr Val Asp Gly Val Glu Val His Asn Ala Lys Thr Lys Pro
705                 710                 715                 720

Arg Glu Glu Gln Tyr Asn Ser Thr Tyr Arg Val Val Ser Val Leu Thr
                725                 730                 735

Val Leu His Gln Asp Trp Leu Asn Gly Lys Glu Tyr Lys Cys Lys Val
                740                 745                 750

Ser Asn Lys Ala Leu Pro Ala Pro Ile Glu Lys Thr Ile Ser Lys Ala
                755                 760                 765

Lys Gly Gln Pro Arg Glu Pro Gln Val Tyr Thr Leu Pro Pro Ser Arg
                770                 775                 780
```

-continued

```
Asp Glu Leu Thr Lys Asn Gln Val Ser Leu Thr Cys Leu Val Lys Gly
785                 790                 795                 800

Phe Tyr Pro Ser Asp Ile Ala Val Glu Trp Glu Ser Asn Gly Gln Pro
            805                 810                 815

Glu Asn Asn Tyr Lys Thr Thr Pro Pro Val Leu Asp Ser Asp Gly Ser
            820                 825                 830

Phe Phe Leu Tyr Ser Lys Leu Thr Val Asp Lys Ser Arg Trp Gln Gln
        835                 840                 845

Gly Asn Val Phe Ser Cys Ser Val Met His Glu Ala Leu His Asn His
        850                 855                 860

Tyr Thr Gln Lys Ser Leu Ser Leu Ser Pro Gly Lys
865                 870                 875
```

BIOMARKERS RELATED TO INTERLEUKIN-33 (IL-33)-MEDIATED DISEASES AND USES THEREOF

CROSS-REFERENCE TO RELATED APPLICATIONS

This application claims the benefit under 35 U.S.C. § 119(e) of U.S. provisional application No. 62/237,624, filed Oct. 6, 2015, which is herein specifically incorporated by reference in its entirety.

REFERENCE TO A SEQUENCE LISTING

This application incorporates by reference the Sequence Listing submitted in Computer Readable Form as file 10187US01-Sequence.txt, created on Oct. 4, 2016 and containing 159,912 bytes.

FIELD OF THE INVENTION

The present invention relates to the identification of particular biomarkers in a mammal that correlate with expression of IL-33 and the use of these biomarkers to identify patients who have, or are likely to develop, an IL-33 mediated disease or disorder and who are more likely to respond to therapy with an IL-33 antagonist. The invention also relates to methods of treatment of an IL-33-mediated disease or disorder in a patient by administering an IL-33 antagonist to the patient in need thereof and monitoring the effectiveness of therapy using the biomarkers described herein.

BACKGROUND

Interleukin-33 (IL-33), which is a member of the IL-1 superfamily of cytokines, is expressed predominantly by stromal cells, such as epithelial and endothelial cells, following pro-inflammatory stimulation. IL-33 is a ligand for ST2, a toll-like/interleukin-1 receptor super-family member that associates with an accessory protein, IL-1 RAcP (for reviews, see, e.g., Kakkar and Lee, Nature Reviews—Drug Discovery 7(10):827-840 (2008), Schmitz et. al., Immunity 23:479-490 (2005); Liew et. al., Nature Reviews—Immunology 10:103-110 (2010); US 2010/0260770; US 2009/0041718). Upon activation of ST2/IL-1 RAcP by IL-33, a signaling cascade is triggered through downstream molecules such as MyD88 (myeloid differentiation factor 88) and TRAF6 (TNF receptor associated factor 6), leading to activation of NFκB (nuclear factor-κB), among others.

IL-33 signaling has been implicated as a factor in a variety of diseases and disorders (Liew et. al., Nature Reviews—Immunology 10:103-110 (2010)). For example, while IL-33 is protective against helminth infection in a host and also reduces atherosclerosis by promoting $T_H2$-type immune responses, it can also promote the pathogenesis of asthma by expanding $T_H2$ cells and mediate joint inflammation, atopic dermatitis and anaphylaxis by mast cell activation. As such, IL-33 may be a new target for therapeutic intervention across a range of diseases; for example, blockade of IL-33 signaling may offer the potential to ameliorate multiple pathogenic features of certain inflammatory diseases.

IL-33 antagonists are described in U.S. Pat. Nos. 5,576, 191; 7,666,622; 8,119,771; 8,187,596; 9,090,694; 9,212, 227; 9,382,318; U.S. patent publication numbers 2007/ 0042978; 2009/0041718; 2010/0260770; 2012/0207752; 2012/0263709; 2014/0140954; 2014/0271642; 2014/ 0212412; EP patents or patent application numbers 1725261 B1; 2069784A1; 2152740A1; 2283860A2; 2475388A1; and PCT publication numbers WO05/079844; WO08/132709; WO08/144610; WO09/053098; WO11/031600; WO14/ 152195 and WO14/164959.

Calcitonin (CT) is a polypeptide hormone, thought to be produced primarily by parafollicular cells of the thyroid (Foster, G. V., et. al., (1964), Nature 202: 1303-1305). CT is a product of the CALCA gene, located on chromosome 11. The CALCA gene encodes the polypeptides procalcitonin (PCT) and PCT gene-related peptide α (proCGRPα), which are differentially expressed by alternative splicing (Christ-Crain, M. et. al. (2008), Crit Care Med 36:1684-1687; Hoff, A O, et. al. (2002), J. Clin. Invest. 110:1849-1857). Calcitonin (CT) is derived from a larger precursor, Procalcitonin (PCT, 116 amino acids), which is cleaved to immature calcitonin (33 amino acids) and then to mature calcitonin, a monomer of a 3.5-kd peptide composed of 32 amino acids. CT is predominantly produced by neuroendocrine cells such as C cells of the thyroid and pulmonary neuroendocrine cells (PNECs) by proteolytic cleavage in the secretory granules of producing cells before being released as mature CT polypeptide. Other cells that express the calca gene include mast cells, dorsal route ganglion cells (DRGs) and cells of the spinal cord. Multiple forms of circulating calcitonin precursors are found in the serum of healthy and diseased individuals (Becker K. et. al. (2004), J Clin Endocrinol Metab 89:1512-1525).

Calcitonin gene related peptide (CGRP) is a member of the calcitonin family of peptides. α-CGRP is a 37-amino acid peptide formed from the alternative splicing of the calcitonin/CGRP gene located on chromosome 11 (Amara, S G, et. al., (1982), Nature, 298 (5871): 240-244).

CT acts to reduce blood calcium, inhibits both osteoclasts and bone resorption, opposing the activity of parathyroid hormone (PTH) (Naot, D. and J. Cornish (2008), Bone 43(5): 813-818). In vivo and in vitro experiments suggest that the major physiological function of CT is to combat hypercalcemia in states of calcium stress such as during pregnancy, growth or lactation (Hoff, A. O., et. al., (2002), J Clin Invest 110(12): 1849-1857; Zaidi, M., et. al., (2002), J Clin Invest 110(12): 1769-1771). Diagnostically, CT is used as biomarker for medullary thyroid carcinoma (MTC). Normal circulating levels of CT peptides are low, however under physiological conditions these levels increase either systemically or locally. High CT levels indicate the presence of MTC and are used to evaluate the efficacy of surgical extirpation and recurrences. CT is also elevated in C-cell hyperplasia, pulmonary and pancreatic tumors, kidney failures and thyroid autoimmune disease (Becker, K. L., et. al., (2004). J Clin Endocrinol Metab 89(4): 1512-1525).

To date, no biomarkers for identifying patients that have, or are prone to develop an IL-33 mediated disease or disorder, or to determine a patient's likelihood to respond to therapy with an IL-33 antagonist have been identified. Although IL-33 antagonists have been identified that show promise in the treatment of inflammatory conditions, or allergies, biomarkers that may predict the efficacy of anti-IL-33 therapy are needed for the effective identification and selection of patient sub-populations that respond favorably to anti-IL-33 therapy. Accordingly, an unmet need exists in the art for identifying and validating predictive and prognostic biomarkers in patients with inflammatory conditions, or allergies, who are administered anti-IL-33 therapy.

BRIEF SUMMARY OF THE INVENTION

According to certain aspects of the present invention, methods are provided for treating, preventing and/or reducing the severity or duration of symptoms of an interleukin-33 (IL-33)-mediated disease or disorder in a subject. The methods of the present invention comprise administering to a subject in need thereof a pharmaceutical composition comprising a therapeutically effective amount of an interleukin-33 (IL-33) antagonist.

In one embodiment of the present invention, the IL-33 antagonist is an antibody or antigen-binding fragment thereof that specifically binds IL-33.

In one embodiment of the present invention, the IL-33 antagonist is a receptor-based antagonist of IL-33, such as an IL-33 trap, as described herein.

The present invention also provides for the identification of particular biomarkers that correlate with the expression of IL-33 in a subject suffering from an IL-33 mediated disease or disorder. Exemplary biomarkers associated with an IL-33-mediated disease or disorder that can be evaluated and/or measured in the context of the present invention include, but are not limited to, polypeptides encoded by the CALCA gene, including calcitonin, procalcitonin, and calcitonin gene-related peptide (CGRP). In one embodiment, the biomarker associated with an IL-33-mediated disease or disorder that can be evaluated and/or measured in the context of the present invention is calcitonin. Other biomarkers associated with an IL-33-mediated disease or disorder that can be evaluated and/or measured in the context of the present invention include, but are not limited to resistin-like alpha (RETNA); chemokine (C—C motif) ligand 8 (Ccl8); serum amyloid A 3 (Saa3); Gm1975 (BC117090); killer cell lectin-like receptor (Kirg1); stefin A1 (Csta); membrane-spanning 4-domain (Ms4a8a); chemokine (C—C motif) ligand 11 (Ccl11); and serine (or cysteine) peptides (Serpina3f).

In a related aspect, the invention provides for the expression of at least one biomarker in the serum of a subject suffering from an IL-33 mediated disease or disorder, which correlates with the level of expression of IL-33 in at least one tissue sample from the subject.

In one embodiment, the serum biomarker that correlates with IL-33 expression levels in at least one tissue sample is calcitonin.

In a certain embodiment, the serum biomarker that correlates with IL-33 expression levels in at least one tissue sample is procalcitonin.

In a related embodiment, the serum biomarker that correlates with IL-33 expression levels in at least one tissue sample is calcitonin gene-related peptide (CGRP).

In another related aspect, the present invention provides a method for treating an interleukin-33 (IL-33) mediated disease or disorder in a subject, the method comprising: (a) selecting a subject who exhibits an elevated level of at least one biomarker associated with an IL-33 mediated disease or disorder prior to, or at the time of treatment, and (b) administering to the subject a pharmaceutical composition comprising a therapeutically effective amount of an interleukin-33 antagonist.

According to a related aspect of the present invention, methods for treating an IL-33-mediated disease or disorder are provided which comprise administering to a subject a pharmaceutical composition comprising a therapeutically effective amount of an IL-33 antagonist, wherein administration of the pharmaceutical composition to the subject results in a decrease in at least one biomarker associated with an IL-33-mediated disease or disorder in the subject.

In one embodiment, the biomarker that is elevated in a subject suffering from an IL-33 mediated disease or disorder is calcitonin and the IL-33 antagonist is a monoclonal antibody that specifically binds to IL-33.

The present invention also provides methods for decreasing the level of one or more IL-33-mediated disease or disorder-associated biomarker(s) in a subject, which results in improving one or more IL-33-mediated disease or disorder-associated parameter(s) in a subject, wherein the methods comprise administering to a subject in need thereof a single initial dose of a pharmaceutical composition comprising an IL-33 antagonist. In certain embodiments, the invention provides administering one or more secondary doses of the pharmaceutical composition comprising the IL-33 antagonist, wherein the administering results in further reduction in the level of one or more of the biomarkers described herein and further improvement in one or more IL-33 mediated disease or disorder-associated parameters in a subject. In one embodiment, there is a strong correlation between the level of the biomarker present in the serum of the subject having an IL-33 mediated disease or disorder and the severity of the disease or disorder-associated parameter, e.g. infiltration of eosinophils or neutrophils into the lungs of the subject, or an increase in cytokine levels (e.g. IL-5) in the lungs of the subject. In certain embodiments, the level of IL-33 in the tissue, e.g. the lung, correlates with the severity of the disease or disorder-associated parameter. In one embodiment, the IL-33 antagonist is a human monoclonal antibody that binds specifically to IL-33. In one embodiment, the IL-33 antagonist is an IL-33 trap, as described herein.

In a related aspect, the present invention provides methods for treating an IL-33-mediated disease or disorder in a subject comprising administering to the subject a pharmaceutical composition comprising a therapeutically effective amount of an antibody or antigen-binding fragment thereof that specifically binds IL-33, wherein the subject has been diagnosed with an IL-33-mediated disease or disorder and has also been selected for treatment on the basis of the subject exhibiting an elevated level of at least one IL-33-mediated disease or disorder-associated biomarker before treatment, as compared to a reference level of the biomarker (e.g., expression of the biomarker in a subset of subjects diagnosed with an IL-33-mediated disease or disorder and/or expression of the biomarker in healthy subjects).

In another related aspect, the present invention also provides methods for treating an IL-33-mediated disease or disorder by administering to the subject a pharmaceutical composition comprising a therapeutically effective amount of an antibody or antigen-binding fragment thereof that specifically binds IL-33, wherein the subject has been diagnosed with an IL-33-mediated disease or disorder, has already been treated with the anti-IL33 antagonist for a defined period of time, and has been selected for further treatment with the IL-33 antagonist on the basis of exhibiting expression of at least one biomarker (e.g., calcitonin, procalcitonin, or calcitonin gene-related peptide (CGRP)) after treatment for a defined period of time, wherein the expression of the biomarker is determined based on a comparison to the level of expression of the respective biomarker in the subject prior to treatment with the anti-IL-33 antagonist.

The invention also provides a method for identifying a subject suffering from an IL-33 mediated disease or disorder who is likely to respond favorably to therapy with an IL-33 antagonist, the method comprising obtaining a sample from the subject and measuring the level of calcitonin in the sample; wherein an elevated level of calcitonin, as compared to the lower level of calcitonin in subjects not suffering from an IL-33 mediated disease or disorder, identifies the patient as a patient who is likely to respond favorably to therapy with an IL-33 antagonist.

In certain embodiments, the subject who is likely to respond favorably to therapy with an IL-33 antagonist may be identified by measuring the level of procalcitonin, or calcitonin gene-related peptide (CGRP) in a tissue sample, wherein an elevated level of either procalcitonin, or calcitonin gene-related peptide (CGRP), as compared to the lower level of procalcitonin, or CGRP in subjects not suffering from an IL-33 mediated disease or disorder, identifies that patient as a patient who is likely to respond favorably to therapy with an IL-33 antagonist.

In another related aspect, the invention provides a method of determining whether a subject is likely to have, or likely to develop an IL-33 mediated disease or disorder, the method comprising obtaining a sample from the subject and measuring in the sample the level of calcitonin; wherein an elevated level of calcitonin, as compared to a reference standard, identifies the patient as a patient who is likely to have, or develop an IL-33 mediated disease or disorder.

In certain embodiments, the invention provides a method of determining whether a subject is likely to have, or likely to develop an IL-33 mediated disease or disorder, the method comprising obtaining a sample from the subject and measuring in the sample the level of procalcitonin, or CGRP; wherein an elevated level of procalcitonin, or CGRP, as compared to reference standards for either of the two biomarkers, identifies the patient as a patient who is likely to have, or develop an IL-33 mediated disease or disorder. Methods for measuring the levels of any of the above biomarkers are known to those of skill in the art.

The sample from the subject may be a solid tissue sample, a cell sample, or a blood sample. The solid tissue sample may be selected from the group consisting of heart, kidney, liver, lung, colon and spleen. The cell sample may be a dorsal root ganglion cell sample, sputum cell sample, bronchoalveolar lavage cell sample, nasal polyps cell sample, fecal cell sample, lung, colon heart, kidney, skin biopsy, or spleen biopsy cell sample. The blood sample may be whole blood, plasma, or serum.

In one embodiment, the IL-33 antagonist to be used in the methods of the invention is an isolated human monoclonal antibody or antigen-binding fragment thereof that specifically binds human interleukin-33 (IL-33), wherein the antibody or antigen-binding fragment comprises: (a) the complementarity determining regions (CDRs) of a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274, 290, and 308; and (b) the CDRs of a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, and 316.

In one embodiment, the IL-33 antagonist to be used in the methods of the invention is an isolated human monoclonal antibody or antigen-binding fragment thereof that specifically binds human interleukin-33 (IL-33), wherein the anti-IL-33 antibody or antigen-binding fragment thereof comprises the heavy and light chain CDRs of a HCVR/LCVR amino acid sequence pair selected from the group consisting of: SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, and 308/316.

In one embodiment, the IL-33 antagonist to be used in the methods of the invention is an isolated human monoclonal antibody or antigen-binding fragment thereof that specifically binds human interleukin-33 (IL-33), wherein the antibody or antigen-binding fragment comprises HCDR1-HCDR2-HCDR3-LCDR1-LCDR2-LCDR3 domains, respectively, selected from the group consisting of: SEQ ID NOs: 4-6-8-12-14-16; 20-22-24-28-30-32; 36-38-40-44-46-48; 52-54-56-60-62-64; 68-70-72-76-78-80; 84-86-88-92-94-96; 100-102-104-108-110-112; 116-118-120-124-126-128; 132-134-136-140-142-144; 148-150-152-156-158-160; 164-166-168-172-174-176; 180-182-184-188-190-192; 196-198-200-204-206-208; 212-214-216-220-222-224; 228-230-232-236-238-240; 244-246-248-252-254-256; 260-262-264-268-270-272; 276-278-280-284-286-288; 292-294-296-300-302-304; and 310-312-314-318-320-322.

In one embodiment, the IL-33 antagonist to be used in the methods of the invention is an isolated human monoclonal antibody or antigen-binding fragment thereof that specifically binds human interleukin-33 (IL-33), wherein the antibody or antigen-binding fragment comprises: (a) a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274, 290, and 308; and (b) a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, and 316.

In one embodiment, the IL-33 antagonist to be used in the methods of the invention is an isolated IL-33 receptor based antagonist (e.g. an IL-33 trap), comprising a first IL-33 binding domain (D1) attached to a multimerizing domain (M), wherein D1 comprises an IL-33-binding portion of an ST2 protein. In one embodiment, the IL-33 trap further comprises one or more additional IL-33 binding domains selected from the group consisting of D2, D3 and D4.

In one embodiment, the IL-33 receptor based antagonist comprises an IL-33-binding portion of an ST2 protein, an extracellular domain of an IL-1 RAcP protein, or other IL-33 binding domain.

In one embodiment, the IL-33 receptor based antagonist is an IL-33 trap comprising the amino acid sequence selected from the group consisting of SEQ ID NOs: 323, 324, 325, 326 and 335.

In one embodiment, the methods of the invention provide administration of an effective amount of a second therapeutic agent useful for diminishing at least one symptom of an IL-33 mediated disease or disorder.

In one embodiment, the second therapeutic agent is selected from the group consisting of a non-steroidal anti-inflammatory (NSAID), a corticosteroid, a bronchial dilator, an antihistamine, epinephrine, a decongestant, a thymic stromal lymphopoietin (TSLP) antagonist, an IL-13 antagonist, an IL-4 antagonist, an IL-4/IL-13 dual antagonist, an IL-5 antagonist, an IL-6 antagonist, an IL-12/23 antagonist, an IL-22 antagonist, an IL-25 antagonist, an IL-17 antagonist, an IL-31 antagonist, an oral PDE4 inhibitor and another IL-33 antagonist or a different antibody or receptor based antagonist to IL-33.

In one embodiment, the invention provides for treatment of a subject suffering from an IL-33 mediated disease or disorder with an IL-33 antagonist selected from an anti-IL-33 antibody or an IL-33 trap, which may be used in combination with any one or more of the second therapeutic agents noted above, wherein the effectiveness of treatment with these agents may be monitored by assessing the level of at least one biomarker selected from the group consisting of calcitonin (Calca), procalcitonin, calcitonin gene-related peptide (CGRP), resistin-like alpha (RETNA), chemokine (C—C motif) ligand 8 (Ccl8), serum amyloid A 3 (Saa3), Gm1975 (BC117090), killer cell lectin-like receptor (Kirg1), stefin A1 (Csta), membrane-spanning 4-domain (Ms4a8a), chemokine (C—C motif) ligand 11 (Ccl11), and serine (or cysteine) peptides (Serpina3f).

In one embodiment, the biomarker is calcitonin and the calcitonin level increases in the serum of the subject having an IL-33 mediated disease or disorder, and the increase in serum calcitonin correlates with an increased level of calcitonin and IL-33 in the lungs of the subject.

In one embodiment, the increased level of calcitonin in the serum of the subject having an IL-33 mediated disease or disorder is reduced to a reference range level following treatment with an anti-IL-33 antagonist.

In one embodiment, a subject suffering from an IL-33 mediated disease or disorder is selected for treatment with an IL-33 antagonist on the basis of exhibiting a mean serum calcitonin level of greater than about 5 pg/ml, greater than about 10 pg/ml, greater than about 50 pg/ml, or greater than about 100 pg/ml prior to, or at the time of treatment.

In one embodiment, a subject suffering from an IL-33 mediated disease or disorder is selected for treatment with an IL-33 antagonist on the basis of exhibiting a mean serum procalcitonin level of greater than about 0.15 ng/ml, greater than about 1.0 ng/ml, greater than about 5 ng/ml, greater than about 10 ng/ml, greater than about 50 ng/ml, or greater than about 100 ng/ml prior to, or at the time of treatment.

In one embodiment, a subject suffering from an IL-33 mediated disease or disorder is selected for treatment with an IL-33 antagonist on the basis of exhibiting a mean serum calcitonin gene-related peptide (CGRP) level of greater than about 45 pg/ml, greater than about 100 pg/ml, greater than about 250 pg/ml, or greater than about 500 pg/ml prior to, or at the time of treatment.

In certain embodiments, the methods of the invention provide for treatment of an IL-33 mediated disease or disorder, which is an inflammatory disease or disorder selected from the group consisting of asthma, allergy, allergic rhinitis, allergic airway inflammation, atopic dermatitis (AD), chronic obstructive pulmonary disease (COPD), inflammatory bowel disease (IBD), multiple sclerosis, arthritis, psoriasis, eosinophilic esophagitis, eosinophilic pneumonia, eosinophilic psoriasis, hypereosinophilic syndrome, graft-versus-host disease, uveitis, cardiovascular disease, pain, multiple sclerosis, lupus, vasculitis, chronic idiopathic urticaria and Eosinophilic Granulomatosis with Polyangiitis (Churg-Strauss Syndrome).

In one embodiment, the IL-33 mediated disease or disorder to be treated is an allergy and the subject selected for treatment with an IL-33 antagonist is selected on the basis of an increase in calcitonin levels that are above normal (e.g. based on a reference level of the biomarker as determined by established values for healthy subjects compared to subjects diagnosed with an IL-33 mediated disease or disorder), wherein the treatment with an IL-33 antagonist comprises administration of a pharmaceutical composition comprising a therapeutically effective amount of a monoclonal antibody that specifically binds IL-33 and comprises an HCVR/LCVR amino acid sequence pair of SEQ ID NOs: 274/282, and wherein the administration results in an improvement in at least one symptom associated with the IL-33 disease or disorder, or an improvement in at least one disease associated parameter; and wherein the calcitonin level is restored to a normal range as determined by comparison to a reference standard.

In one embodiment, the IL-33 mediated disease or disorder to be treated is an allergy and the subject selected for treatment with an IL-33 antagonist is selected on the basis of an increase in serum calcitonin levels as determined by comparison with a reference standard, wherein the calcitonin level correlates with an increase in IL-33 level in the subject, or with an increase in at least one disease parameter in the subject, and wherein the increase in IL-33 level is determined using a binding assay comprising an antibody that binds specifically to human IL-33 and comprises a HCVR/LCVR amino acid sequence pair of SEQ ID NOs: 274/282.

The present invention also includes any combination of the embodiments discussed above or herein. Particular embodiments of the present invention will become apparent from a review of the ensuing detailed description.

BRIEF DESCRIPTION OF THE FIGURES

FIG. 5A: Frequency of lung neutrophils; FIG. 5B: Frequency of lung eosinophils; FIG. 5C: lung IL-5 levels.

FIG. 6A: correlation between serum CT levels and frequency of lung neutrophils; FIG. 6B: correlation between serum CT levels and frequency of lung eosinophils; FIG. 6C: correlation between serum CT and lung IL-5 protein levels.

FIG. 7A: correlation between lung IL-33 levels and frequency of lung neutrophils; FIG. 7B: correlation between lung IL-33 levels and frequency of lung eosinophils; FIG. 7C: correlation between lung IL-33 and lung IL-5 protein levels.

DETAILED DESCRIPTION

Figure 1A:
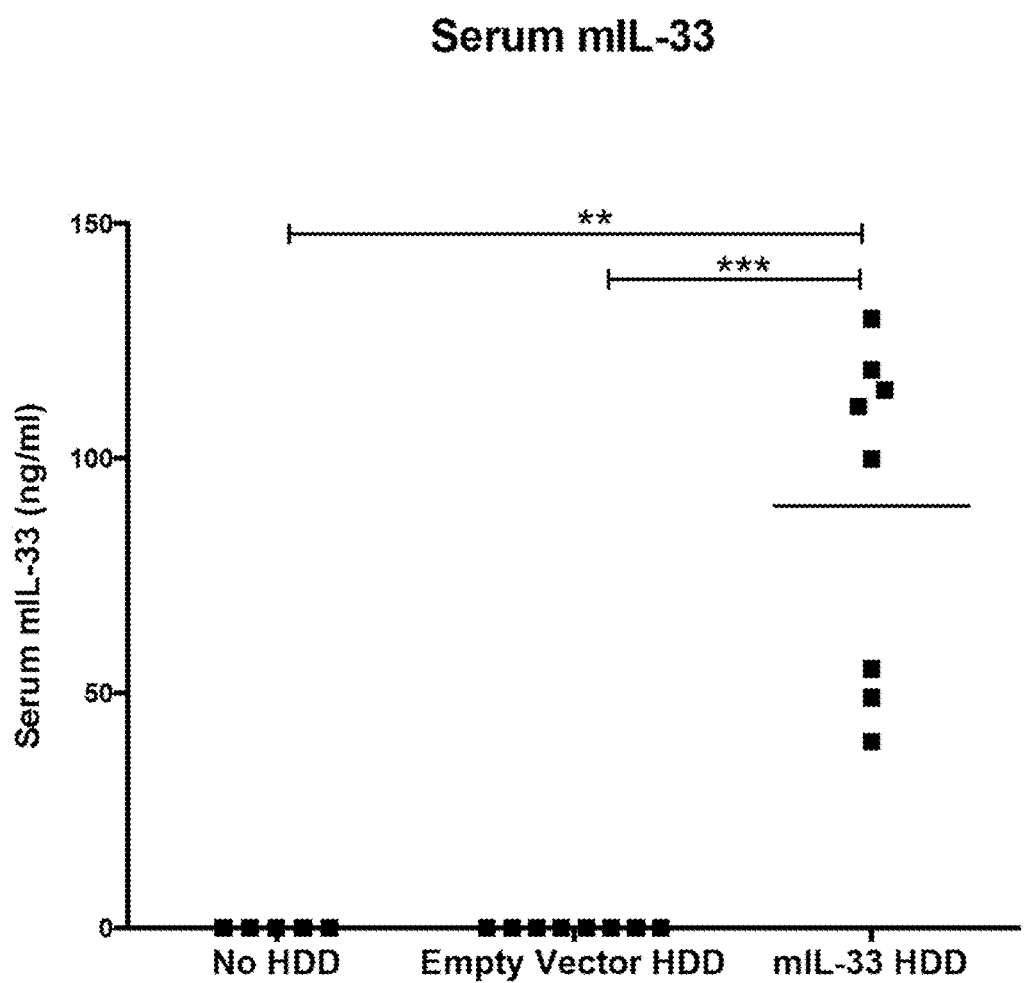
FIGS. 1A and 1B: Show mouse serum IL-33 (FIG. 1A) and mouse Calcitonin (CT) levels (FIG. 1B) in mouse IL-33 HDD experiment.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.). As used herein, the terms "treat", "treating", or the like, mean to alleviate symptoms, eliminate the causation of symptoms either on a temporary or permanent basis, or to prevent or slow the appearance of symptoms of the named disorder or condition.

Although any methods and materials similar or equivalent to those described herein can be used in the practice of the present invention, the preferred methods and materials are now described. All patents, applications and non-patent publications mentioned in this specification are incorporated herein by reference in their entireties.

Biomarkers Associated with an IL-33-Mediated Disease or Disorder

The present invention includes methods involving the use, quantification, and analysis of biomarkers associated with an IL-33-mediated disease or disorder.

An "IL-33 mediated disease or disorder" may be selected from any inflammatory disease or disorder such as, but not limited to, asthma, allergy, allergic rhinitis, allergic airway inflammation, atopic dermatitis (AD), chronic obstructive pulmonary disease (COPD), inflammatory bowel disease (IBD), multiple sclerosis, arthritis, psoriasis, eosinophilic esophagitis, eosinophilic pneumonia, eosinophilic psoriasis, hypereosinophilic syndrome, graft-versus-host disease, uveitis, cardiovascular disease, pain, multiple sclerosis, lupus, vasculitis, chronic idiopathic urticaria and Eosinophilic Granulomatosis with Polyangiitis (Churg-Strauss Syndrome).

The asthma may be selected from the group consisting of allergic asthma, non-allergic asthma, severe refractory asthma, asthma exacerbations, viral-induced asthma or viral-induced asthma exacerbations, steroid resistant asthma, steroid sensitive asthma, eosinophilic asthma or non-eosinophilic asthma and other related disorders characterized by airway inflammation or airway hyperresponsiveness (AHR).

The COPD may be a disease or disorder associated in part with, or caused by, cigarette smoke, air pollution, occupational chemicals, allergy or airway hyperresponsiveness.

The allergy may be associated with foods, pollen, mold, dust mites, animals, or animal dander.

The IBD may be selected from the group consisting of ulcerative colitis, Crohn's Disease, collagenous colitis, lymphocytic colitis, ischemic colitis, diversion colitis, Behcet's syndrome, infective colitis, indeterminate colitis, and other disorders characterized by inflammation of the mucosal layer of the large intestine or colon.

The arthritis may be selected from the group consisting of osteoarthritis, rheumatoid arthritis and psoriatic arthritis.

As used herein, the term "an IL-33-mediated disease or disorder-associated biomarker", or a "biomarker associated with an IL-33-mediated disease or disorder" means any biological response, cell type, parameter, protein, polypeptide, enzyme, enzyme activity, metabolite, nucleic acid, carbohydrate, or other biomolecule which is present or detectable in a patient suffering from an IL-33-mediated disease or disorder at a level or amount that is different from (e.g., greater than or less than) the level or amount of the marker present or detectable in a non-IL-33-mediated disease or disorder patient. Exemplary IL-33-mediated disease or disorder-associated biomarkers include, but are not limited to, e.g., polypeptides encoded by the CALCA gene, including calcitonin, procalcitonin, or calcitonin gene-related peptide (CGRP). Other biomarkers associated with an IL-33-mediated disease or disorder include, but are not limited to resistin-like alpha (RETNA); chemokine (C—C motif) ligand 8 (Ccl8); serum amyloid A 3 (Saa3); Gm1975 (BC117090); killer cell lectin-like receptor (Kirg1); stefin A1 (Csta); membrane-spanning 4-domain (Ms4a8a); chemokine (C—C motif) ligand 11 (Ccl11); and serine (or cysteine) peptides (Serpina3f).

Methods for detecting and/or quantifying such biomarkers are known in the art; kits for measuring such biomarkers are available from various commercial sources; and various commercial diagnostic laboratories offer services, which provide measurements of such biomarkers as well.

In one embodiment, the biomarker is calcitonin and the level of calcitonin is increased in a subject suffering from, or prone to developing an IL-33 mediated disease or disorder. In one embodiment, the biomarker is procalcitonin and the level of procalcitonin is increased in a subject suffering from, or prone to developing an IL-33 mediated disease or disorder. In a related embodiment, the biomarker is calcitonin gene-related peptide (CGRP) and the level of CGRP is increased in a subject suffering from, or prone to developing an IL-33 mediated disease or disorder. The level of calcitonin, procalcitonin, or CGRP may be assessed using any method known to those skilled in the art. Methods of detection include an immunoassay using any label for detection, such as a radioisotopic label, an enzymatic label, or a chemiluminescent label. The interpretation of the results must take into account the method used, the subject's age, gender and weight (See d'Herbomez, M. et. al., (2007), Eur. J. Endocrinology 157:749-755). Generally, a "normal" reference value of calcitonin in males is less than about 16 pg/mL and less than about 8 pg/mL for females. More recently, Camacho et. al. developed a new immunofluorometric assay for serum calcitonin and have validated it in samples from 794 patients. The results obtained using this assay showed that the normal cut-off range for males was less than 11.1 pg/mL and less than 5.5 pg/mL for females. (See Camacho, et. al., (2014), Eur. Thyroid J., Jun; 3(2): 117-24. A "reference" range of procalcitonin in adults and children older than 72 hours is about 0.15 ng/mL or less. In healthy adults, the reference range of procalcitonin is below the level of detection (See Dandona, P. et. al. (1994), J. Clin. Endocrinol. Metab. December 79(6):1605-8.). A normal range of CGRP in healthy individuals is generally below about 45 pg/ml. As such, a value above that may be considered indicative of the presence of a disease or disorder.

An "IL-33 associated disease parameter" may include, but not be limited to, an increase in infiltration of neutrophils, eosinophils or ST2+ CD4 T cells to a tissue (e.g. lung), goblet cells metaplasia, an increase in ST2 levels in the tissue or an increase in the level of a cytokine, such as IL-1β, IL-4, IL-5, IL-6, IL-9, IL-13, IL-33, MCP-1, TNFα in the tissue.

According to certain aspects of the invention, methods for treating an IL-33-mediated disease or disorder are provided which comprise: (a) selecting a subject who exhibits a level of at least one biomarker prior to or at the time of treatment which signifies the disease state, and (b) administering to the subject a pharmaceutical composition comprising a therapeutically effective amount of an IL-33 antagonist. In one embodiment of this aspect of the invention, the subject is selected on the basis of an elevated level of calcitonin. In one embodiment, the IL-33 antagonist is an isolated monoclonal antibody the specifically binds to IL-33, or a receptor based IL-33 antagonist (an IL-33 trap as described herein).

According to other aspects of the invention, methods for treating an IL-33-mediated disease or disorder are provided which comprise administering to a subject a pharmaceutical composition comprising a therapeutically effective amount of an IL-33 antagonist, wherein administration of the pharmaceutical composition to the subject results in a decrease in at least one biomarker (e.g., calcitonin (Calca), procalcitonin, calcitonin gene-related peptide (CGRP), resistin-like alpha (RETNA), chemokine (C—C motif) ligand 8 (Ccl8), serum amyloid A 3 (Saa3), Gm1975 (BC117090), killer cell lectin-like receptor (Kirg1), stefin A1 (Csta), membrane-spanning 4-domain (Ms4a8a), chemokine (C—C motif) ligand 11 (Ccl11), and serine (or cysteine) peptides (Serpina3f), etc.) at a time after administration of the pharmaceutical composition, as compared to the level of the biomarker in the subject prior to the administration.

As will be appreciated by a person of ordinary skill in the art, an increase or decrease in a biomarker associated with an IL-33 mediated disease or disorder can be determined by comparing (i) the level of the biomarker measured in a subject at a defined time point after administration of the pharmaceutical composition comprising an IL-33 antagonist to (ii) the level of the biomarker measured in the patient prior to the administration of the pharmaceutical composition comprising an IL-33 antagonist (i.e., the "baseline measurement"). The defined time point at which the biomarker is measured can be, e.g., at about 4 hours, 8 hours, 12 hours, 1 day, 2 days, 3 days, 4 days, 5 days, 6 days, 7 days, 8 days, 9 days, 10 days, 14 days, 15 days, 20 days, 35 days, 40 days, 50 days, 55 days, 60 days, 65 days, 70 days, 75 days, 80 days, 84 days, 85 days, or more after administration of the of the pharmaceutical composition comprising an IL-33 antagonist.

According to certain particular embodiments of the present invention, a subject may exhibit a decrease in the level of one or more of calcitonin, procalcitonin, CGRP, resistin-like alpha (RETNA), chemokine (C—C motif) ligand 8 (Ccl8), serum amyloid A 3 (Saa3), Gm1975 (BC117090), killer cell lectin-like receptor (Kirg1), stefin A1 (Csta), membrane-spanning 4-domain (Ms4a8a), chemokine (C—C motif) ligand 11 (Ccl11), and serine (or cysteine) peptides (Serpina3f) following administration of a pharmaceutical composition comprising an IL-33 antagonist (e.g., an anti-IL-33 antibody, or an IL-33 receptor based antagonist (an IL-33 trap). For example, at about day 4, day 8, day 14, day 15, day 22, day 25, day 29, day 36, day 43, day 50, day 57, day 64, day 71, day 84, or day 85, following administration of a first, second, third or fourth dose of a pharmaceutical composition comprising about an anti-hIL-33 antagonist. The dose of an anti-IL-33 antagonist administered to a patient may vary depending upon the age and the size of the patient, target disease, conditions, route of administration, and the like. The preferred dose is typically calculated according to body weight or body surface area. When an IL-33 antagonist is used for treating a condition or disease associated with IL-33 activity in an adult patient, it may be advantageous to intravenously administer the anti-IL-33 antagonist normally at a dose of about 0.01 to about 20 mg/kg body weight, more preferably about 0.02 to about 7, about 0.03 to about 5, or about 0.05 to about 3 mg/kg body weight.

The subject, according to the present invention, may exhibit a decrease in at least one of the following biomarkers: a polypeptide encoded by the CALCA gene, selected from the group consisting of calcitonin, procalcitonin and CGRP, or may exhibit a decrease in at least one of the following biomarkers: resistin-like alpha (RETNA); chemokine (C—C motif) ligand 8 (Ccl8); serum amyloid A 3 (Saa3); Gm1975 (BC117090); killer cell lectin-like receptor (Kirg1); stefin A1 (Csta); membrane-spanning 4-domain (Ms4a8a); chemokine (C—C motif) ligand 11 (Ccl11); and serine (or cysteine) peptides (Serpina3f), of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of biomarker in the subject just prior to the first administration). Similarly, at about day 4, day 8, day 14, day 15, day 22, day 25, day 29, day 36, day 43, day 50, day 57, day 64, day 71, day 84 or day 85, following administration of a first, second, third or fourth dose of a pharmaceutical composition of an anti-hIL-33 antagonist, the subject, according to the present invention, may exhibit a decrease in at least one of the biomarkers described above of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of biomarker in the subject just prior to the first administration).

The present invention also includes methods for determining whether a subject is a suitable subject (e.g., a subject who is likely to respond favorably to therapy with an IL-33 antagonist) for whom administration of a pharmaceutical composition comprising an IL-33 antagonist would be beneficial. For example, if an individual, prior to receiving a pharmaceutical composition comprising an IL-33 antagonist, exhibits a level of a biomarker associated with an IL-33-mediated disease or disorder, which signifies the disease state, the individual is therefore identified as a suitable patient for whom administration of a pharmaceutical composition of the invention (a composition comprising an anti-IL-33 antagonist) would be beneficial. According to certain exemplary embodiments, an individual may be identified as a good candidate for anti-IL-33 therapy if the individual exhibits one or more of the following: (i) a calcitonin level greater than about 5 pg/mL, greater than about 10 pg/mL, greater than about 20 pg/mL, greater than about 30 pg/mL, greater than about 40 pg/mL, greater than about 50 pg/mL, greater than about 60 pg/mL, greater than about 70 pg/mL, greater than about 80 pg/mL, greater than about 90 pg/mL, greater than about 100 pg/mL, or greater than about 200 pg/mL. Additional criteria, such as other clinical indicators of an IL-33-mediated disease or disorder may be used in combination with any of the biomarkers described herein to identify an individual as a suitable candidate for anti-IL-33 therapy as described elsewhere herein (e.g., increase in infiltration of neutrophils, eosinophils or ST2+ CD4 T cells to a tissue (e.g. lung), goblet cells metaplasia, an increase in ST2 levels in the tissue or an increase in the level of a cytokine, such as IL-1β, IL-4, IL-5, IL-6, IL-9, IL-13, IL-33, MCP-1, TNFα in the tissue, as well as interferon gamma).

In other aspects of the invention, biomarker levels and/or changes in biomarker levels with treatment may have predictive value for efficacy of anti-IL33 therapy with particular anti-IL33 agents.

An additional aspect of the invention provides methods of determining whether a subject is likely to have, or likely to develop an IL-33 mediated disease or disorder, wherein the method comprises obtaining a biological sample from the subject and measuring the level of at least one of the biomarkers described herein; wherein the elevated level of at least one biomarker as compared to the level of the biomarker from a subject not having an IL-33 mediated disease or disorder, or not likely to develop an IL-33 mediated disease or disorder, identifies the subject as a subject who is likely to have, or develop an IL-33 mediated disease or disorder.

An additional aspect of the invention features methods of treating an IL-33-mediated disease or disorder in a subject comprising administration of an anti-IL33 antagonist, wherein the subject has been diagnosed with an IL-33-mediated disease or disorder, has been treated with the anti-IL33 antagonist, and has been selected for further treatment with the IL-33 antagonist on the basis of exhibiting reduced expression of a biomarker (e.g. calcitonin), wherein the reduced expression of the biomarker is determined based on a comparison to the level of expression of the respective biomarker in the subject prior to treatment with the anti-IL-33 antagonist. A particular aspect of the invention features methods of treating an IL-33-mediated disease or disorder in a subject comprising administration of an anti-IL33 antagonist, wherein the subject has been diagnosed with an IL-33-mediated disease or disorder, has been treated with the anti-IL33 antagonist, and has been selected for further treatment with the IL-33 antagonist on the basis of exhibiting reduced expression of the biomarker, wherein the reduced expression of the biomarker in comparison to pre-treatment expression levels is equal to or greater than about a 10%, 20%, 30%, 40%, 50%, 60%, 70%, 80% or 90% reduction in biomarker expression.

Interleukin-33 Antagonists

As disclosed in detail above, the present invention includes methods, which comprise administering to a subject in need thereof a therapeutic composition comprising an IL-33 antagonist. As used herein, an "IL-33 antagonist" is any agent, which binds to or interacts with IL-33, or with its receptor and inhibits the normal biological signaling function of IL-33 when IL-33 is expressed on a cell in vitro or in vivo. Non-limiting examples of categories of IL-33 antagonists include small molecule IL-33 antagonists, anti-IL-33 aptamers, peptide-based IL-33 antagonists (e.g., "peptibody" molecules), antibodies or antigen-binding fragments of antibodies that specifically bind human IL-33, or receptor based IL-33 antagonists (e.g. an IL-3 trap), such as those described herein.

In one embodiment, the present invention includes methods that comprise administering to a patient a human antibody, or an antigen-binding fragment thereof, that binds specifically to hIL-33. As used herein, the term "hIL-33" means a human cytokine that specifically binds to its receptor, ST2. The amino acid sequence of human ST2 is shown in SEQ ID NO: 334. The amino acid sequence of human IL-33 is shown in SEQ ID NO: 306. The nucleic acid encoding human IL-33 is shown in SEQ ID NO: 305. The anti-IL-33 antibodies may be selected from any one or more of those having the amino acid sequences described in Table 1.

In one embodiment, the present invention includes methods that comprise administering to a patient a receptor based IL-33 antagonist, for example, an IL-33 trap, such as those described herein. Five different exemplary IL-33 traps of the invention were constructed using standard molecular biological techniques. Table 2a sets forth a summary description of the different IL-33 traps and their component parts. Table 2b sets forth the amino acid sequences of the IL-33 traps and their component parts.

The term "antibody," as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-IL-33 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include non-naturally occurring human antibodies. The term includes antibodies that are recombinantly produced in a non-human mammal, or in cells of a non-human mammal. The term is not intended to include antibodies isolated from or generated in a human subject.

The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et. al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et. al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-33, as used in the context of the present invention, includes antibodies that bind IL-33 or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-33 may, however, have cross-reactivity to other antigens, such as IL-33 molecules from other (non-human) species.

The anti-IL-33 antibodies useful for the methods of the present invention may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-IL-33 antibodies comprising variants of any of the HCVR, LCVR, and/or CDR amino acid sequences disclosed herein having one or more conservative substitutions. For example, the present invention includes the use of anti-IL-33 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance," as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$," as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Preparation of Human Antibodies

Methods for generating human antibodies in transgenic mice are known in the art. Any such known methods can be used in the context of the present invention to make human antibodies that specifically bind to human IL-33.

Using VELOCIMMUNE™ technology (see, for example, U.S. Pat. No. 6,596,541, Regeneron Pharmaceuticals) or any other known method for generating monoclonal antibodies, high affinity chimeric antibodies to IL-33 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc., using standard procedures known to those skilled in the art. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies that can be used in the methods of the present invention possess high affinities, as described above, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Specific examples of human antibodies or antigen-binding fragments of antibodies that specifically bind IL-33 which can be used in the context of the methods of the present invention include any antibody or antigen-binding fragment which comprises the three heavy chain CDRs (HCDR1, HCDR2 and HCDR3) contained within a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274, 290, and 308. The antibody or antigen-binding fragment may comprise the three light chain CDRs (LCVR1, LCVR2, LCVR3) contained within a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, and 316. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et. al., *J. Mol. Biol.* 273:927-948 (1997); and Martin et. al., *Proc. Natl. Acad. Sci. USA* 86:9268-9272 (1989). Public databases are also available for identifying CDR sequences within an antibody.

In certain embodiments of the present invention, the antibody or antigen-binding fragment thereof comprises the six CDRs (HCDR1, HCDR2, HCDR3, LCDR1, LCDR2 and LCDR3) from the heavy and light chain variable region amino acid sequence pairs (HCVR/LCVR) selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, and 308/316.

In certain embodiments of the present invention, the antibody or antigen-binding fragment thereof comprises HCVR/LCVR amino acid sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, and 308/316.

The study summarized in the attached Examples utilized an anti-h IL-33 antibody referred to as H4H9675P. This antibody comprises an HCVR/LCVR amino acid sequence pair having SEQ ID NOs: 274/282, and HCDR1-HCDR2-HCDR3/LCDR1-LCDR2-LCDR3 domains represented by SEQ ID NOs: 276-278-280/SEQ ID NOs: 284-286-288. However, the methods of the present invention can be practiced using any anti-IL-33 antibody disclosed herein, as well as variants and antigen-binding fragments of such antibody.

Pharmaceutical Compositions

The present invention includes methods, which comprise administering an IL-33 antagonist to a patient, wherein the IL-33 antagonist is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et. al. "Compendium of excipients for parenteral formulations" PDA (1998) J Pharm Sci Technol 52:238-311.

The dose of antibody administered to a patient according to the methods of the present invention may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-33 antibodies may be determined empirically; for example, patient progress can be monitored by periodic assessment, and the dose adjusted accordingly. Moreover, interspecies scaling of dosages can be performed using well-known methods in the art (e.g., Mordenti et. al., 1991, *Pharmaceut. Res.* 8:1351). Specific exemplary doses of anti-IL33 antibodies, and administration regimens involving the same, that can be used in the context of the present invention are disclosed elsewhere herein.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et. al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-33 antibody that can be used in the context of the present invention are disclosed, e.g., in US Patent Application Publication No. 2014/0271658.

Dosage

The amount of IL-33 antagonist (e.g., anti-IL-33 antibody) administered to a subject according to the methods of the present invention is, generally, a therapeutically effective amount. As used herein, the phrase "therapeutically effective amount" means an amount of IL-33 antagonist that results in a detectable improvement in one or more symptoms or indicia of an IL-33 mediated disease or disorder. A "therapeutically effective amount" also includes an amount of IL-33 antagonist that inhibits, prevents, lessens, or delays the progression of such disease or disorder in a subject.

In the case of an anti-IL-33 antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-IL-33 antibody. In certain embodiments, 75 mg, 150 mg, 200 mg, or 300 mg of an anti-IL-33 antibody is administered to a subject.

The amount of IL-33 antagonist contained within the individual doses may be expressed in terms of milligrams of antibody per kilogram of patient body weight (i.e., mg/kg). For example, the IL-33 antagonist may be administered to a patient at a dose of about 0.0001 to about 10 mg/kg of patient body weight.

Combination Therapies

The methods of the present invention, according to certain embodiments, comprise administering to the subject one or more additional therapeutic agents in combination with the IL-33 antagonist. As used herein, the expression "in combination with" means that the additional therapeutic agents are administered before, after, or concurrent with the pharmaceutical composition comprising the IL-33 antagonist.

For example, when administered "before" the pharmaceutical composition comprising the IL-33 antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the IL-33 antagonist. When administered "after" the pharmaceutical composition comprising the IL-33 antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the IL-33 antagonist. Administration "concurrent" with the pharmaceutical composition comprising the IL-33 antagonist means that the additional therapeutic agent is administered to the subject in a separate dosage form within less than 5 minutes (before, after, or at the same time) of Administration of the pharmaceutical composition comprising the IL-33 antagonist, or administered to the subject as a single combined dosage formulation comprising both the additional therapeutic agent and the IL-33 antagonist.

The present invention includes methods of treating an IL-33 mediated disease or disorder, which comprise administering to a patient in need of such treatment an anti-hIL-33 antibody, or an IL-33 trap in combination with at least one additional therapeutic agent. Examples of additional therapeutic agents which can be administered in combination with an anti-hIL-33 antibody in the practice of the methods of the present invention include, but are not limited to a non-steroidal anti-inflammatory (NSAID), a steroid, a corticosteroid (inhaled or topical), an immunosuppressant (e.g. cyclophosphamide), an anticholinergic agent (e.g. tiotropium), a muscarinic agent (e.g. glycopyrronium), a phosphodiesterase inhibitor (e.g. theophylline, roflumilast, cilomilast), a beta blocker, cyclosporine, tacrolimus, pimecrolimus, azathioprine, methotrexate, cromolyn sodium, a proteinase inhibitor, a bronchial dilator, a beta-2-agonist, an antihistamine, epinephrine, a decongestant, a leukotriene inhibitor, a mast cell inhibitor, a thymic stromal lymphopoietin (TSLP) antagonist, a TNF antagonist, an IgE antagonist, an IL-1 antagonist, an IL-4 or IL-4R antagonist, an IL-13 or IL-13R antagonist, an IL-4/IL-13 dual antagonist, an IL-5 antagonist, an IL-6 or IL-6R antagonist, an antagonist of IL-8, an IL-9 antagonist, an IL-12/23 antagonist, an IL-22 antagonist, an IL-17 antagonist, an IL-31 antagonist, an oral PDE4 inhibitor, an IL-25 antagonist and another IL-33 antagonist or a different antibody or receptor based antagonist to IL-33, and any other compound known to treat, prevent, or ameliorate an IL-33 mediated disease or disorder in a human subject. For example, for concurrent administration, a pharmaceutical formulation can be made which contains both an anti-hIL-33 antibody and at least one additional therapeutic agent. The amount of the additional therapeutic agent that is administered in combination with the anti-hIL-33 antibody in the practice of the methods of the present invention can be easily determined using routine methods known and readily available in the art.

Administration Regimens

The present invention includes methods comprising administering to a subject a pharmaceutical composition comprising an IL-33 antagonist at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of a pharmaceutical composition comprising an anti-IL-33 antibody, once a week dosing at an amount of about 0.01 to about 20 mg/kg body weight, more preferably about 0.02 to about 7, about 0.03 to about 5, or about 0.05 to about 3 mg/kg body weight.

According to certain embodiments of the present invention, multiple doses of an IL-33 antagonist may be administered to a subject over a defined time course. The methods according to this aspect of the invention comprise sequentially administering to a subject multiple doses of an IL-33 antagonist. As used herein, "sequentially administering" means that each dose of IL-33 antagonist is administered to the subject at a different point in time, e.g., on different days separated by a predetermined interval (e.g., hours, days, weeks or months). The present invention includes methods which comprise sequentially administering to the patient a single initial dose of an IL-33 antagonist, followed by one or more secondary doses of the IL-33 antagonist, and optionally followed by one or more tertiary doses of the IL-33 antagonist.

The terms "initial dose," "secondary doses," and "tertiary doses," refer to the temporal sequence of administration of the IL-33 antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of IL-33 antagonist, but generally may differ from one another in terms of frequency of administration. In certain embodiments, however, the amount of IL-33 antagonist contained in the initial, secondary and/or tertiary doses varies from one another (e.g., adjusted up or down as appropriate) during the course of treatment. In certain embodiments, two or more (e.g., 2, 3, 4, or 5) doses area at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose," as used herein, means, in a sequence of multiple administrations, the dose of IL-33 antagonist which is administered to a patient prior to the administration of the very next dose in the sequence with no intervening doses.

The methods according to this aspect of the invention may comprise administering to a patient any number of secondary and/or tertiary doses of an IL-33 antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens comprising an up-titration option (also referred to herein as "dose modification"). As used herein, an "up-titration option" means that, after receiving a particular number of doses of an IL-33 inhibitor, if a patient has not achieved a specified improvement in one or more defined therapeutic parameters (e.g., at least a 20% improvement), or otherwise exhibits a clear lack of efficacy in the opinion of a physician or health care provider, the dose of the IL-33 inhibitor is thereafter increased. For example, in the case of a therapeutic regimen comprising administration of 150 mg doses of an anti-IL-33 antibody to a patient at a frequency of once every two weeks, if after 8, 10, 12, 14, 16 or more weeks, the patient has not achieved at least a 20% improvement in one parameter, or if the patient exhibits a clear lack of efficacy in the opinion of a physician or other health care provider, then the dose of anti-IL-33 antibody is increased to e.g., 200 mg, 300 mg, or more, administered once every two weeks thereafter (e.g., starting at week 10, 12, 14, 16, 18, or later).

Treatment Populations

The present invention includes methods, which comprise administering to a subject in need thereof a therapeutic composition comprising an IL-33 antagonist. As used herein, the expression "a subject in need thereof" means a human or non-human animal that exhibits one or more symptoms or indicia of an IL-33 mediated disease or disorder, such as those described herein (e.g., inflammation, eosinophilia in the lungs, neutrophil infiltration into the lungs, elevated levels of certain cytokines in the lungs, such as, but not limited to IL-5, etc.) and/or who has been diagnosed with any of the IL-33 mediated disease or disorders described herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Antibodies to Human IL-33

An immunogen comprising human IL-33 was administered directly, with an adjuvant to stimulate the immune response, to a VELOCIMMUNE® mouse comprising DNA encoding human Immunoglobulin heavy and kappa light chain variable regions. The antibody immune response was monitored by an IL-33-specific immunoassay. When a desired immune response was achieved splenocytes were harvested and fused with mouse myeloma cells to preserve their viability and form hybridoma cell lines. The hybridoma cell lines were screened and selected to identify cell lines that produce IL-33-specific antibodies. Using this technique several anti-IL-33 chimeric antibodies (i.e., antibodies possessing human variable domains and mouse constant domains) were obtained; exemplary antibodies generated in this manner were designated as follows: H1M9559N, H1M9566N, H1M9568N and H1M9565N. The human variable domains from the chimeric antibodies were subsequently cloned onto human constant domains to make fully human anti-IL-33 antibodies as described herein.

Anti-IL-33 antibodies were also isolated directly from antigen-positive B cells without fusion to myeloma cells, as described in US 2007/0280945A1. Using this method, several fully human anti-IL-33 antibodies (i.e., antibodies possessing human variable domains and human constant domains) were obtained; exemplary antibodies generated in this manner were designated as follows: H4H9629P, H4H9633P, H4H6940P, H4H9659P, H4H9660P, H4H9662P, H4H9663P, H4H9664P, H4H9665P, H4H9666P, H4H9667P, H4H9670P, H4H9671P, H4H9672P, H4H9675P, and H4H9676P.

Certain biological properties of the exemplary anti-IL-33 antibodies generated in accordance with the methods of this Example are described in detail in the Examples set forth below.

Example 2. Heavy and Light Chain Variable Region Amino Acid Sequences

Table 1 sets forth the heavy and light chain variable region amino acid sequence pairs, and CDR sequences, of selected anti-IL-33 antibodies and their corresponding antibody identifiers.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1M9559N | 2 | 4 | 6 | 8 | 10 | 12 | 14 | 16 |
| H1M9566N | 18 | 20 | 22 | 24 | 26 | 28 | 30 | 32 |
| H1M9568N | 34 | 36 | 38 | 40 | 42 | 44 | 46 | 48 |
| H4H9629P | 50 | 52 | 54 | 56 | 58 | 60 | 62 | 64 |
| H4H9633P | 66 | 68 | 70 | 72 | 74 | 76 | 78 | 80 |
| H4H9640P | 82 | 84 | 86 | 88 | 90 | 92 | 94 | 96 |
| H4H9659P | 98 | 100 | 102 | 104 | 106 | 108 | 110 | 112 |
| H4H9660P | 114 | 116 | 118 | 120 | 122 | 124 | 126 | 128 |
| H4H9662P | 130 | 132 | 134 | 136 | 138 | 140 | 142 | 144 |
| H4H9663P | 146 | 148 | 150 | 152 | 154 | 156 | 158 | 160 |
| H4H9664P | 162 | 164 | 166 | 168 | 170 | 172 | 174 | 176 |
| H4H9665P | 178 | 180 | 182 | 184 | 186 | 188 | 190 | 192 |
| H4H9666P | 194 | 196 | 198 | 200 | 202 | 204 | 206 | 208 |
| H4H9667P | 210 | 212 | 214 | 216 | 218 | 220 | 222 | 224 |
| H4H9670P | 226 | 228 | 230 | 232 | 234 | 236 | 238 | 240 |
| H4H9671P | 242 | 244 | 246 | 248 | 250 | 252 | 254 | 256 |
| H4H9672P | 258 | 260 | 262 | 264 | 266 | 268 | 270 | 272 |
| H4H9675P | 274 | 276 | 278 | 280 | 282 | 284 | 286 | 288 |
| H4H9676P | 290 | 292 | 294 | 296 | 298 | 300 | 302 | 304 |
| H1M9565N | 308 | 310 | 312 | 314 | 316 | 318 | 320 | 322 |

Antibodies are typically referred to herein according to the following nomenclature: Fc prefix (e.g. "H1M," or "H4H"), followed by a numerical identifier (e.g. "9559," "9566," or "9629" as shown in Table 1), followed by a "P," or "N" suffix. Thus, according to this nomenclature, an antibody may be referred to herein as, e.g., "H1M9559N," "H1M9566N," "H4H9629P," etc. The H1M and H4H prefixes on the antibody designations used herein indicate the particular Fc region isotype of the antibody. For example, an "H1M" antibody has a mouse IgG1 Fc, whereas an "H4H" antibody has a human IgG4 Fc. As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties are expected to be identical or substantially similar regardless of the nature of the Fc domain.

Example 3. Construction of IL-33 Traps

Five different exemplary IL-33 antagonists (IL-33 traps) of the invention were constructed using standard molecular biological techniques. The first IL-33 antagonist (hST2-hFc, SEQ ID NO:323) consists of the soluble extracellular region of human ST2 (SEQ ID NO:327) fused at its C-terminus to the N-terminus of a human IgG1 Fc region (SEQ ID NO:331). The second IL-33 antagonist (hST2-mFc, SEQ ID NO:324) consists of the soluble extracellular region of human ST2 (SEQ ID NO:327) fused at its C-terminus to the N-terminus of a mouse IgG2a Fc region (SEQ ID NO:332). The third IL-33 antagonist (hST2-hIL RAcP-mFc, SEQ ID NO: 325) consists of an in-line fusion having human ST2 (SEQ ID NO:327) at its N-terminus, followed by the extracellular region of human IL-1 RAcP (SEQ ID NO:329), followed by a mouse IgG2a Fc (SEQ ID NO:332) at its C-terminus. The fourth IL-33 antagonist (mST2-mIL1 RAcP-mFc, SEQ ID NO: 326) consists of an in-line fusion having mouse ST2 (SEQ ID NO:328) at its N-terminus, followed by the extracellular region of mouse IL-1 RAcP (SEQ ID NO:330), followed by a mouse IgG2a Fc (SEQ ID NO:332) at its C-terminus. The fifth IL-33 antagonist (hST2-hIL RAcP-hFc, SEQ ID NO:335) consists of an in line fusion having human ST2 of SEQ ID NO: 327 at its N-terminus, followed by the extracellular region of human IL-1 RAcP (SEQ ID NO: 329) followed by a human IgG1 Fc (SEQ ID NO: 331) at its C terminus. Table 2a sets forth a summary description of the different IL-33 antagonists and their component parts. Table 2b sets forth the amino acid sequences of the IL-33 antagonists and their component parts.

TABLE 2a

Summary of IL-33 Antagonists (IL-33 traps)

| IL-33 Antagonist | Amino Acid Sequence of Full Antagonist Molecule | D1 Component | D2 Component | M Component |
| --- | --- | --- | --- | --- |
| hST2-hFc | SEQ ID NO: 323 | human ST2 extracellular (SEQ ID NO: 327) | Absent | human IgG1 Fc (SEQ ID NO: 331) |
| hST2-mFc | SEQ ID NO: 324 | human ST2 extracellular (SEQ ID NO: 327) | Absent | mouse IgG2a Fc (SEQ ID NO: 332) |
| hST2-hIL1RAcP-mFc | SEQ ID NO: 325 | human ST2 extracellular (SEQ ID NO: 327) | human IL-1RAcP extracellular (SEQ ID NO: 329) | mouse IgG2a Fc (SEQ ID NO: 332) |
| mST2-mIL1RAcP-mFc | SEQ ID NO: 326 | mouse ST2 extracellular (SEQ ID NO: 328) | mouse IL-1 RAcP extracellular (SEQ ID NO: 330) | mouse IgG2a Fc (SEQ ID NO: 332) |
| hST2-hIL1RAcP-hFc | SEQ ID NO: 335 | human ST2 extracellular (SEQ ID NO: 327) | human IL-1RAcP extracellular (SEQ ID NO: 329) | human IgG1 Fc (SEQ ID NO: 331) |

TABLE 2b

Amino Acid Sequences

| Identifier | Sequence |
| --- | --- |
| SEQ ID NO: 323 (hST2-hFc) | KFSKQSWGLENEALIVRCPRQGKPSYTVDWYYSQTNKSIPTQERNRVFASGQL LKFLPAAVADSGIYTCIVRSPTFNRTGYANVTIYKKQSDCNVPDYLMYSTVSGSE KNSKIYCPTIDLYNWTAPLEWFKNCQALQGSRYRAHKSFLVIDNVMTEDAGDYT CKFIHNENGANYSVTATRSFTVKDEQGFSLFPVIGAPAQNEIKEVEIGKNANLTC SACFGKGTQFLAAVLWQLNGTKITDFGEPRIQQEEGQNQSFSNGLACLDMVLRI ADVKEEDLLLQYDCLALNLHGLRRHTVRLSRKNPIDHHSDKTHTCPPCPAPELL GGPSVFLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTISKAKGQ PREPQVYTLPPSRDELTKNQVSLTCLVKGFYPSDIAVEWESNGQPENNYKTTPP VLDSDGSFFLYSKLTVDKSRWQQGNVFSCSVMHEALHNHYTQKSLSLSPGK |

TABLE 2b-continued

Amino Acid Sequences

| Identifier | Sequence |
|---|---|
| SEQ ID NO: 324 (hST2-mFc) | KFSKQSWGLENEALIVRCPRQGKPSYTVDWYYSQTNKSIPTQERNRVFASGQL LKFLPAAVADSGIYTCIVRSPTFNRTGYANVTIYKKQSDCNVPDYLMYSTVSGSE KNSKIYCPTIDLYNWTAPLEWFKNCQALQGSRYRAHKSFLVIDNVMTEDAGDYT CKFIHNENGANYSVTATRSFTVKDEQGFSLPVIGAPAQNEIKEVEIGKNANLTC SACFGKGTQFLAAVLWQLNGTKITDFGEPRIQQEEGQNQSFSNGLACLDMVLRI ADVKEEDLLLQYDCLALNLHGLRRHTVRLSRKNPIDHHSEPRGPTIKPCPPCKCP APNLLGGPSVFIFPPKIKDVLMISLSPIVICVVVDVSEDDPDVQISWFVNNVEVHT AQTQTHREDYNSTLRVVSALPIQHQDWMSGKEFKCKVNNKDLPAPIERTISKPK GSVRAPQVYVLPPPEEEMTKKQVTLTCMVTDFMPEDIYVEWTNNGKTELNYKN TEPVLDSDGSYFMYSKLRVEKKNWVERNSYSCSVVHEGLHNHHTTKSFSRTPG K |
| SEQ ID NO: 325 (hST2-hIL1RAcP-mFc) | KFSKQSWGLENEALIVRCPRQGKPSYTVDWYYSQTNKSIPTQERNRVFASGQL LKFLPAAVADSGIYTCIVRSPTFNRTGYANVTIYKKQSDCNVPDYLMYSTVSGSE KNSKIYCPTIDLYNWTAPLEWFKNCQALQGSRYRAHKSFLVIDNVMTEDAGDYT CKFIHNENGANYSVTATRSFTVKDEQGFSLPVIGAPAQNEIKEVEIGKNANLTC SACFGKGTQFLAAVLWQLNGTKITDFGEPRIQQEEGQNQSFSNGLACLDMVLRI ADVKEEDLLLQYDCLALNLHGLRRHTVRLSRKNPIDHHSSERCDDWGLDTMRQI QVFEDEPARIKCPLFEHFLKFNYSTAHSAGLTLIWYWTRQDRDLEEPINFRLPEN RISKEKDVLWFRPTLLNDTGNYTCMLRNTTYCSKVAFPLEVVQKDSCFNSPMKL PVHKLYIEYGIQRITCPNVDGYFPSSVKPTITWYMGCYKIQNFNNVIPEGMNLSFL IALISNNGNYTCVVTYPENGRTFHLTRTLTVKVVGSPKNAVPPVIHSPNDHVVYE KEPGEELLIPCTVYFSFLMDSRNEVWWTIDGKKPDDITIDVTINESISHSRTEDET RTQILSIKKVTSEDLKRSYVCHARSAKGEVAKAAKVKQKVPAPRYTVESGEPRG PTIKPCPPCKCPAPNLLGGPSVFIFPPKIKDVLMISLSPIVICVVVDVSEDDPDVQI SWFVNNVEVHTAQTQTHREDYNSTLRVVSALPIQHQDWMSGKEFKCKVNNKD LPAPIERTISKPKGSVRAPQVYVLPPPEEEMTKKQVTLTCMVTDFMPEDIYVEWT NNGKTELNYKNTEPVLDSDGSYFMYSKLRVEKKNWVERNSYSCSVVHEGLHN HHTTKSFSRTPGK |
| SEQ ID NO: 326 (mST2-mIL1RAcP-mFc) | SKSSWGLENEALIVRCPQRGRSTYPVEWYYSDTNESIPTQKRNRIFVSRDRLKF LPARVEDSGIYACVIRSPNLNKTGYLNVTIHKKPPSCNIPDYLMYSTVRGSDKNF KITCPTIDLYNWTAPVQWFKNCKALQEPRFRAHRSYLFIDNVTHDDEGDYTCQF THAENGTNYIVTATRSFTVEEKGFSMFPVITNPPYNHTMEVEIGKPASIACSACF GKGSHFLADVLWQINKTVVGNFGEARIQEEEGRNESSSNDMDCLTSVLRITGVT EKDLSLEYDCLALNLHGMIRHTIRLRRKQPIDHRSERCDDWGLDTMRQIQVFED EPARIKCPLFEHFLKYNYSTAHSSGLTLIWYWTRQDRDLEEPINFRLPENRISKEK DVLWFRPTLLNDTGNYTCMLRNTTYCSKVAFPLEVVQKDSCFNSAMRFPVHKM YIEHGIHKITCPNVDGYFPSSVKPSVTWYKGCTEIVDFHNVLPEGMNLSFFIPLVS NNGNYTCVVTYPENGRLFHLTRTVTVKVVGSPKDALPPQIYSPNDRVVYEKEPG EELVIPCKVYFSFIMDSHNEVWWTIDGKKPDDVTVDITINESVSYSSTEDETRTQI LSIKKVTPEDLRRNYVCHARNTKGEAEQAAKVKQKVIPPRYTVESGEPRGPTIKP CPPCKCPAPNLLGGPSVFIFPPKIKDVLMISLSPIVICVVVDVSEDDPDVQISWFV NNVEVHTAQTQTHREDYNSTLRVVSALPIQHQDWMSGKEFKCKVNNKDLPAPI ERTISKPKGSVRAPQVYVLPPPEEEMTKKQVTLTCMVTDFMPEDIYVEWTNNGK TELNYKNTEPVLDSDGSYFMYSKLRVEKKNWVERNSYSCSVVHEGLHNHHTTK SFSRTPGK |
| SEQ ID NO: 327 (human ST2 extracellular domain) | KFSKQSWGLENEALIVRCPRQGKPSYTVDWYYSQTNKSIPTQERNRVFASGQL LKFLPAAVADSGIYTCIVRSPTFNRTGYANVTIYKKQSDCNVPDYLMYSTVSGSE KNSKIYCPTIDLYNWTAPLEWFKNCQALQGSRYRAHKSFLVIDNVMTEDAGDYT CKFIHNENGANYSVTATRSFTVKDEQGFSLPVIGAPAQNEIKEVEIGKNANLTC SACFGKGTQFLAAVLWQLNGTKITDFGEPRIQQEEGQNQSFSNGLACLDMVLRI ADVKEEDLLLQYDCLALNLHGLRRHTVRLSRKNPIDHHS |
| SEQ ID NO: 328 (mouse ST2 extracellular domain) | SKSSWGLENEALIVRCPQRGRSTYPVEWYYSDTNESIPTQKRNRIFVSRDRLKF LPARVEDSGIYACVIRSPNLNKTGYLNVTIHKKPPSCNIPDYLMYSTVRGSDKNF KITCPTIDLYNWTAPVQWFKNCKALQEPRFRAHRSYLFIDNVTHDDEGDYTCQF THAENGTNYIVTATRSFTVEEKGFSMFPVITNPPYNHTMEVEIGKPASIACSACF GKGSHFLADVLWQINKTVVGNFGEARIQEEEGRNESSSNDMDCLTSVLRITGVT EKDLSLEYDCLALNLHGMIRHTIRLRRKQPIDHR |
| SEQ ID NO: 329 (human IL1RAcP extracellular domain) | SERCDDWGLDTMRQIQVFEDEPARIKCPLFEHFLKFNYSTAHSAGLTLIWYWTR QDRDLEEPINFRLPENRISKEKDVLWFRPTLLNDTGNYTCMLRNTTYCSKVAFPL EVVQKDSCFNSPMKLPVHKLYIEYGIQRITCPNVDGYFPSSVKPTITWYMGCYKI QNFNNVIPEGMNLSFLIALISNNGNYTCVVTYPENGRTFHLTRTLTVKVVGSPKN AVPPVIHSPNDHVVYEKEPGEELLIPCTVYFSFLMDSRNEVWWTIDGKKPDDITI DVTINESISHSRTEDETRTQILSIKKVTSEDLKRSYVCHARSAKGEVAKAAKVKQK VPAPRYTVE |

TABLE 2b-continued

Amino Acid Sequences

| Identifier | Sequence |
|---|---|
| SEQ ID NO: 330 (mouse IL1RAcP extracellular domain) | SERCDDWGLDTMRQIQVFEDEPARIKCPLFEHFLKYNYSTAHSSGLTLIWYWTR QDRDLEEPINFRLPENRISKEKDVLWFRPTLLNDTGNYTCMLRNTTYCSKVAFPL EVVQKDSCFNSAMRFPVHKMYIEHGIHKITCPNVDGYFPSSVKPSVTWYKGCTE IVDFHNVLPEGMNLSFFIPLVSNNGNYTCVVTYPENGRLFHLTRTVTVKVVGSPK DALPPQIYSPNDRVVYEKEPGEELVIPCKVYFSFIMDSHNEVWWTIDGKKPDDV TVDITINESVSYSSTEDETRTQILSIKKVTPEDLRRNYVCHARNTKGEAEQAAKVK QKVIPPRYTVE |
| SEQ ID NO: 331 (human IgG1 Fc) | DKTHTCPPCPAPELLGGPSVFLFPPKPKDTLMISRTPEVTCVVVDVSHEDPEVK FNWYVDGVEVHNAKTKPREEQYNSTYRVVSVLTVLHQDWLNGKEYKCKVSNK ALPAPIEKTISKAKGQPREPQVYTLPPSRDELTKNQVSLTCLVKGFYPSDIAVEW ESNGQPENNYKTTPPVLDSDGSFFLYSKLTVDKSRWQQGNVFSCSVMHEALH NHYTQKSLSLSPGK |
| SEQ ID NO: 332 (mouse IgG2a Fc) | EPRGPTIKPCPPCKCPAPNLLGGPSVFIFPPKIKDVLMISLSPIVTCVVVDSEDD PDVQISWFVNNVEVHTAQTQTHREDYNSTLRVVSALPIQHQDWMSGKEFKCKV NNKDLPAPIERTISKPKGSVRAPQVYVLPPPEEEMTKKQVTLTCMVTDFMPEDIY VEWTNNGKTELNYKNTEPVLDSDGSYFMYSKLRVEKKNWVERNSYSCSVVHE GLHNHHTTKSFSRTPGK |
| SEQ ID NO: 333 (M. fascicularis IL-33-6His) | SITGISPITESLASLSTYNDQSITFALEDESYEIYVEDLKKDKKKDKVLLSYYESQH PSSESGDGVDGKMLMVTLSPTKDFWLQANNKEHSVELHKCEKPLPDQAFFVLH NRSFNCVSFECKTDPGVFIGVKDNHLALIKVDYSENLGSENILFKLSEILEHHHHH H |
| SEQ ID NO: 335 (hST2-hIL1RAcP-hFc) | KFSKQSWGLENEALIVRCPRQGKPSYTVDWYYSQTNKSIPTQERNRVFASGQL LKFLPAAVADSGIYTCIVRSPTFNRTGYANVTIYKKQSDCNVPDYLMYSTVSGSE KNSKIYCPTIDLYNWTAPLEWFKNCQALQGSRYRAHKSFLVIDNVMTEDAGDYT CKFIHNENGANYSVTATRSFTVKDEQGFSLFPVIGAPAQNEIKEVEIGKNANLTC SACFGKGTQFLAAVLWQLNGTKITDFGEPRIQQEEGQNQSFSNGLACLDMVLRI ADVKEEDLLLQYDCLALNLHGLRRHTVRLSRKNPIDHHSSERCDDWGLDTMRQI QVFEDEPARIKCPLFEHFLKFNYSTAHSAGLTLIWYWTRQDRDLEEPINFRLPEN RISKEKDVLWFRPTLLNDTGNYTCMLRNTTYCSKVAFPLEVVQKDSCFNSPMKL PVHKLYIEYGIQRITCPNVDGYFPSSVKPTITWYMGCYKIQNFNNVIPEGMNLSFL IALISNNGNYTCVVTYPENGRTFHLTRTLTVKVVGSPKNAVPPVIHSPNDHVVYE KEPGEELLIPCTVYFSFLMDSRNEVWWTIDGKKPDDITIDVTINESISHSRTEDET RTQILSIKKVTSEDLKRSYVCHARSAKGEVAKAAKVKQKVPAPRYTVEDKTHTCP PCPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEKT ISKAKGQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQKSLS LSPGK |

Example 4. Biomarkers for IL-33 Activity

Studies were done to determine which genes were elevated in mice that overexpressed IL-33. The studies described below summarize the methods and animal models used to determine which genes correlated with IL-33 expression in vivo and which genes were modulated following treatment of the animals with an IL-33 antagonist.

Hydrodynamic DNA Delivery

Mouse IL-33 was overexpressed in wild type (WT) mice by hydrodynamic DNA delivery (HDD). For the HDD experiment, WT mice were injected with either 50 µg or 25 ug of a plasmid expressing full-length mouse IL-33 (See GenBank accession number NM_001164724; mIL-33) or with 50 µg or 25 ug of the same plasmid devoid of coding sequence (empty vector). Mice were sacrificed 7 days after the HDD injection, and blood, dorsal root ganglia (DRG), heart, kidney, liver, lung and spleen were collected. The top ten genes expressed in these tissues are shown in table 4 below.

Microarray Analysis of Collected Tissue

Cy3-CTP was incorporated into amplified cRNA from 500 ng of total RNA using QuickAmp RNA Amplification Kit (Agilent). Cy3 labeled cRNA from each sample was then hybridized to a custom Agilent array comprising of 43538 60 mer oligos covering mouse transcriptome. The hybridization and wash of the arrays were performed according to the Agilent protocol and arrays were scanned on an Agilent Microarray scanner. The data was extracted from scanned array images using Agilent Feature Extraction Software 9.5.

Serum Collection

Whole blood was collected into Microtainer® tubes by cardiac puncture at the end of the study. Blood was allowed to clot by leaving it undisturbed at room temperature for at least 30 minutes. Clotted blood and cells were pelleted by centrifuging at 18,000×g for 10 minutes at 4° C. in a refrigerated centrifuge. The resulting supernatant, designated serum, was transferred into clean polypropylene plates and processed or stored appropriately.

Determination of IL-33 Protein Concentrations in the Serum or Cell Lysate Extracts ELISA kits from R&D systems were used to determine IL-33 concentrations for human (DY3625) and mouse (DY3626) IL-33 according to the manufacturers instructions.

Determination of Mouse Calcitonin (CT) Concentrations in the Serum or Cell Lysate Extracts Mouse calcitonin was measured in the serum of mice using a mouse Calcitonin (CT) ELISA kit from CusaBio (Through ARP) Cat#CSB-E05133m. The assay procedure was carried out according to the manufacturers instructions provided with the kits.

Determination of Mouse IL-5 Concentrations in Cell Lysate Extracts

Cytokine concentrations in the lung protein extracts were measured using a V-Plex custom Mouse multiplex immunoassay kit (MesoScale Discovery, #K152A41), according to the manufacturer's instructions.

House Dust Mite Induced Chronic Lung Inflammation Model

IL-33 Humin mice were intranasally administered either 50 μg house dust mite extract (HDM; Greer, #XPB70D3A2.5) diluted in 20 μL of 1× phosphate buffered saline (PBS) or 20 μL of 1×PBS for 3 days per week for 15 weeks. A second control group of IL33 Humln mice were administered 50 μg HDM extract diluted in 20 μL of 1×PBS for 3 days per week for either 4 or 11 weeks, to assess the severity of the disease at the onset of antibody treatment. Two groups of HDM challenged mice were injected subcutaneously with 25 mg/kg of either an anti-IL-33 antibody, H4H9675P, or an isotype control antibody starting after either 4 or 11 weeks of HDM challenge and then twice per week until the end of the HDM challenge (8 or 4 weeks of antibody treatment). On day 85 of the study, all mice were sacrificed and their lungs were harvested. Experimental dosing and treatment protocol for groups of mice are shown in Table 3.

IL-33 Humin mice were intranasally administered either 50 μg house dust mite extract (HDM; Greer, #XPB70D3A2.5) diluted in 20 μL of 1× phosphate buffered saline (PBS) or 20 μL of 1×PBS for 3 days per week for 15 weeks. A second control group of IL33 Humln mice were administered 50 μg HDM extract diluted in 20 μL of 1×PBS for 3 days per week for 11 weeks, to assess the severity of the disease at the onset of antibody treatment. Two groups of HDM challenged mice were injected subcutaneously with 25 mg/kg of either an anti-IL-33 antibody, H4H9675P, or an isotype control antibody starting after 11 weeks of HDM challenge and then twice per week until the end of the HDM challenge (8 weeks of antibody treatment). On day 85 of the study, all mice were sacrificed and their lungs were harvested. Experimental dosing and treatment protocol for groups of mice are shown in Table 3.

TABLE 3

Experimental dosing and treatment protocol for groups of mice

| Group | Mice | Intranasal challenge | Length of intranasal challenge | Antibody |
|---|---|---|---|---|
| 1 | IL-33 Humln mice | 1X PBS | 15 weeks | None |
| 2 | IL-33 Humln mice | 50 μg HDM in 20 μL 1X PBS | 4 or 11 weeks | None |
| 3 | IL-33 Humln mice | 50 μg HDM in 20 μL 1X PBS | 15 weeks | None |
| 4 | IL-33 Humln mice | 50 μg HDM in 20 μL 1X PBS | 15 weeks | Isotype control antibody |
| 5 | IL-33 Humln mice | 50 μg HDM in 20 μL 1X PBS | 15 weeks | Anti-IL-33 antibody (H4H9675P) |

Tissue Harvest for Gene Expression Analysis

After exsanguination, lung was removed, placed into tubes containing 400 μL of RNA Later (Ambion, Cat#AM720) and stored at −20° C. until processing. Tissues were homogenized in TRIzol and chloroform was used for phase separation. The aqueous phase, containing total RNA, was purified using MagMAX™-96 for Microarrays Total RNA Isolation Kit according to manufacturer's specifications. Genomic DNA was removed using MagMAX™ Turbo™ DNase Buffer and TURBO DNase from the MagMAX kit listed above. mRNA (up to 2.5 μg) was reverse-transcribed into cDNA using SuperScript® VILO™ Master Mix. cDNA was diluted to 2 ng/μL and 10 ng cDNA was amplified with the TaqMan® Gene Expression Master Mix and the relevant probes (mouse B2m, mouse Calca, human IL33) using the ABI 7900HT Sequence Detection System (Applied Biosystems). The B2m probe was used to amplify the beta-2 microblobulin (B2m) gene as an internal control in order to normalize cDNA input differences. Data analysis was performed using Microsoft Excel and Graph Pad Prism™ software. Expression of each gene was normalized to B2m expression within the same sample.

Lung Harvest for Cytokine Analysis

After exsanguination, the cranial and middle lobes of the right lung from each mouse were removed and placed into tubes containing a solution of tissue protein extraction reagent (1× T-PER reagent; Pierce, #78510) supplemented with 1× Halt Protease inhibitor cocktail (Pierce, #78430). All further steps were performed on ice. The volume of T-PER Reagent (containing the protease inhibitor cocktail) was adjusted for each sample to match a 1:8 (w/v) tissue to T-PER ratio. Lung samples were homogenized in the tubes, using the Tissue Lyser II (Qiagen, Cat#85300). The resulting lysates were centrifuged to pellet debris. The supernatants containing the soluble protein extracts were transferred to fresh tubes and stored at 4° C. until further analysis.

Total protein content in the lung protein extracts was measured using a Bradford assay. For the assay, 10 μL of diluted extract samples were plated into 96 well plates in duplicates and mixed with 200 μL of 1× Dye Reagent (Biorad, #500-0006). Serial dilutions of bovine serum albumin (BSA; Sigma, #A7979), starting at 700 μg/mL in 1× T-Per reagent were used as a standard to determine the protein concentration of the extracts. After a 5-minute incubation at room temperature, absorbance at 595 nm was measured on a Molecular Devices SpectraMax M5 plate reader. Data analysis to determine total lung extract protein content based on the BSA standard was performed using GraphPad Prism™ software.

Each cytokine concentration in lung total protein extracts from all mice in each group was normalized to the total protein content of the extracts measured by the Bradford assay, and expressed for each group as average pg of cytokine per mg of total lung proteins (pg/mg lung protein, ±SD).

TABLE 4

Top IL-33 Perturbed Genes

| DrgIL33 | Heart IL33 | Kidney IL33 | Liver IL33 | Lung IL33 | Spleen IL33 | Gene Symbol | Description |
|---|---|---|---|---|---|---|---|
| 10.2 | 415.9 | 33.5 | 72.7 | 5.0 | 86.3 | Calca | Calcitonin/calcitonin-gene related peptide (CGRP) |

TABLE 4-continued

Top IL-33 Perturbed Genes

| DrgIL33 | Heart IL33 | Kidney IL33 | Liver IL33 | Lung IL33 | Spleen IL33 | Gene Symbol | Description |
|---|---|---|---|---|---|---|---|
| 36.2 | 114.8 | 51.7 | 572.8 | 24.9 | 13.8 | Retnla | Resistin like alpha |
| 6.5 | 194.0 | 19.5 | 152.2 | 4.5 | 19.4 | Ccl8 | Chemokine (C-C motif) ligand 8 |
| 6.5 | 17.8 | 251.0 | 14.9 | 8.0 | 45.9 | Saa3 | Serum amyloid A 3 |
| 38.3 | 28.2 | 8.3 | 66.6 | 53.2 | 29.3 | BC117090 | Gm1975 |
| 4.9 | 32.8 | 61.2 | 40.4 | 15.3 | 3.6 | Klrg1 | Killer cell lectin-like receptor |
| 15.4 | 11.7 | 6.8 | 86.7 | 27.1 | 13.8 | Csta | Stefin A1 |
| 5.7 | 46.1 | 18.2 | 38.4 | 1.8 | 4.5 | Ms4a8a | Membrane-spanning 4-domain |
| 1.7 | 19.0 | 23.3 | 81.6 | 9.4 | 6.6 | Ccl11 | Chemokine (C-C motif) ligand 11 |
| 3.7 | 17.9 | 49.0 | 18.0 | 25.8 | 10.5 | Serpina3f | Serine (or cysteine) peptides |

Lung Harvest for Pulmonary Cell Infiltrate Analysis

After exsanguination, the caudal lobe of the right lung from each mouse was removed, placed into a tube containing a solution of 20 µg/mL DNase and 0.7 U/mL Liberase TH diluted in Hank's Balanced Salt Solution (HBSS) and chopped into pieces that were approximately 2 to 3 mm in size. The tubes with the chopped lungs were then incubated in a 37° C. water bath for 20 minutes. The reaction was stopped by adding ethylenediaminetetraacetic acid (EDTA) at a final concentration of 10 mM. The samples were then transferred to gentleMACS C Tubes. The volume in the C Tubes was brought up to 3 mL with MACS buffer and the samples were subsequently dissociated to form single cell suspensions using a gentleMACS Dissociator® (Miltenyi Biotec). The tubes were then centrifuged and the resulting pellet was resuspended in 4 mL of 1× Red Blood Cell Lysing Buffer to lyse red blood cells. After incubation for 3 minutes at room temperature, 10 mL of 1×DPBS was added to deactivate the red blood cell lysing buffer. The cell suspensions were then centrifuged, and the resulting cell pellets were resuspended in 1 mL of 1×DPBS. The resuspended samples were centrifuge-filtered (1 minute at 400×g) through a 100 µm filter plate and approximately $1.5 \times 10^6$ cells per well were plated in a 96-well U-bottom plate. Cells were then centrifuged and the cell pellets resuspended in 100 µL of Near-IR LIVE/DEAD® Fixable Dead Cell Stain (Invitrogen Cat#: L34976, Lot#: 1647137) diluted at 1:500 in 1×DPBS to determine cell viability. Cells were incubated with the viability dye for 20 minutes at room temperature while protected from light. After one wash in 1×DPBS, cells were incubated in 50 µL of MACS buffer containing 10 µg/mL of purified rat anti-mouse CD16/CD32 Fc Block, for 10 minutes at 4° C. The cells were then incubated in the appropriate 2× antibody mixture diluted in Brilliant Stain Buffer (described in Table 5) for 30 minutes at 4° C. while protected from light. After antibody incubation, the cells were washed twice in MACS buffer, resuspended in BD CytoFix that had been diluted 1:4 in 1×DPBS and then incubated for 15 minutes at 4° C. while protected from light. The cells were subsequently washed and resuspended in MACS buffer. Cell suspensions were then filtered into a new U-Bottom plate through an AcroPrep Advance 96 Filter Plate 30-40 µm. Sample data were acquired on a LSR Fortessa X-20 cell analyzer using the HTS attachment (BD Biosciences). Data analysis was performed using FlowJo X Software (Tree Star, OR) and statistical analysis was performed using GraphPad Prism™ (GraphPad Software, CA). Eosinophils were defined as live (cell viability dye negative), singlets, $CD45^+$, $F4/80^+$, $Ly6G^-$, $CD11c^{lo-Int}$, $SiglecF^{hi}$. Neutrophils were defined as live, singlets, $CD45^+$, $F4/80^-$, $Ly6G^+$. Data for eosinophils, and neutrophils were expressed as frequency of live cells.

TABLE 5

Antibodies Used for Flow Cytometry Analysis

| Antibody | Fluorochrome | Manufacturer | Catalog #, Lot # | Final dilution |
|---|---|---|---|---|
| CD45 | Alexa Fluor 700 | BioLegend | 103128, B191240 | 1/200 |
| Siglec-F | BV 421 | BD | 562681, 4234913 | 1/200 |
| F4/80 | PE | BD | 56410, 5054900 | 1/500 |
| Ly6G | BUV395 | BD | 563978, 4178621 | 1/200 |
| CD11c | APC | BD | 550261, 5016523 | 1/200 |

Statistical Analysis

Statistical analyses were performed using Graph Pad Prism™ version 6.0 (GraphPad Software, CA).

Normality of the data was evaluated using the Kolmogorov-Smirnov test. If data passed the normality test, and standard deviations of the different groups were not statistically different from each other as assessed by the Brown-Forsythe test, results were interpreted by one-way analysis of variance (ANOVA) followed by the Tukey post hoc test for multiple comparisons. If data failed to pass the normality test, or standard deviations were significantly different, results were interpreted using the Kruskal-Wallis test followed by the Dunn's post hoc test for multiple comparisons. Differences were considered to be statistically significant when P value <0.05.

Correlation coefficient and significance were computed using two-tailed Spearman non-parametric correlation. Correlations were considered to be statistically significant when P value <0.05.

Figure 1B:
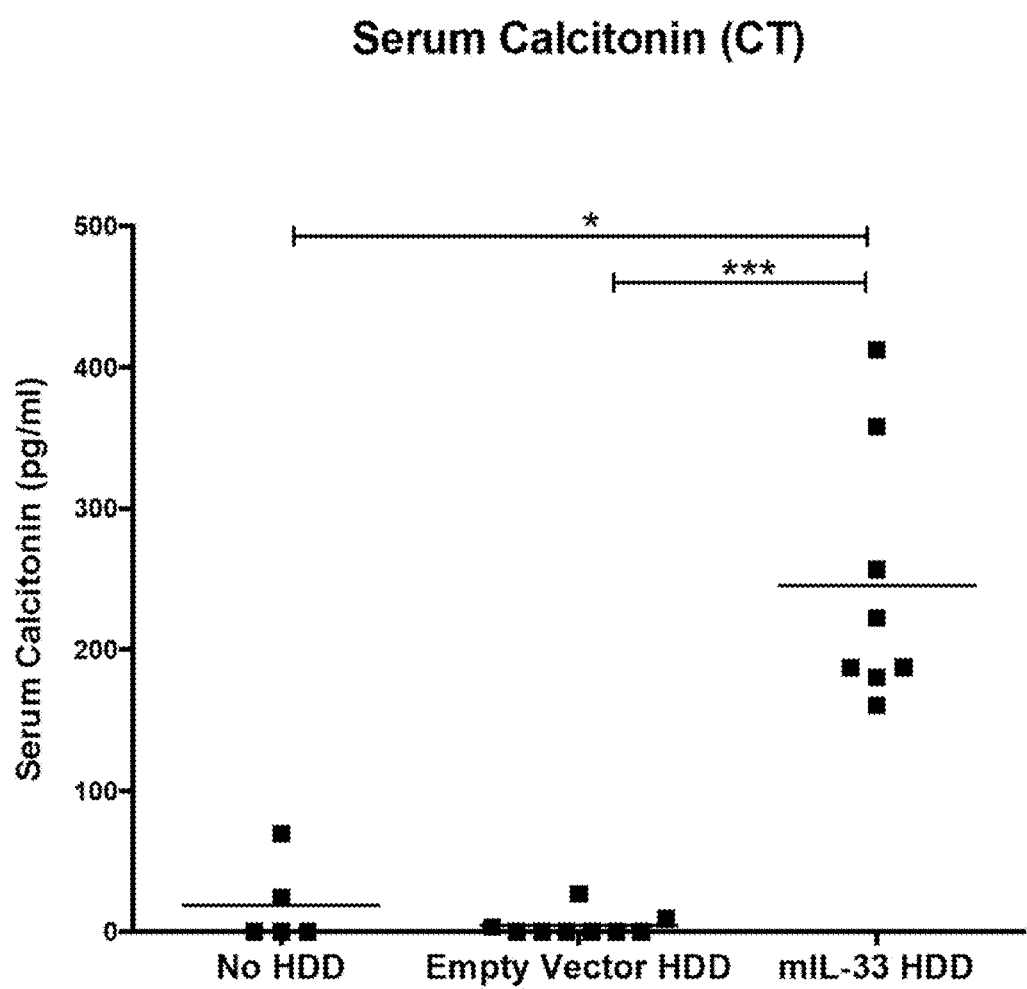

Summary of Results:

The results demonstrated that the top ten genes that were perturbed in animals that overexpressed IL-33 were calcitonin (Calca), resistin-like alpha (RETNA), chemokine (C—C motif) ligand 8 (Ccl8), serum amyloid A 3 (Saa3), Gm 1975 (BC117090), killer cell lectin-like receptor (Kirg1), stefin A1 (Csta), membrane-spanning 4-domain (Ms4a8a), chemokine (C—C motif) ligand 11 (Ccl11), and serine (or cysteine) peptides (Serpina3f) (See Table 4). Moreover, the data also showed that both serum IL-33 and serum calcitonin were significantly elevated in this mouse model (See FIG. 1A for serum IL-33 levels and FIG. 1B for serum calcitonin levels). The increase in serum IL-33 correlated with the increase in serum levels of calcitonin.

Figure 2:
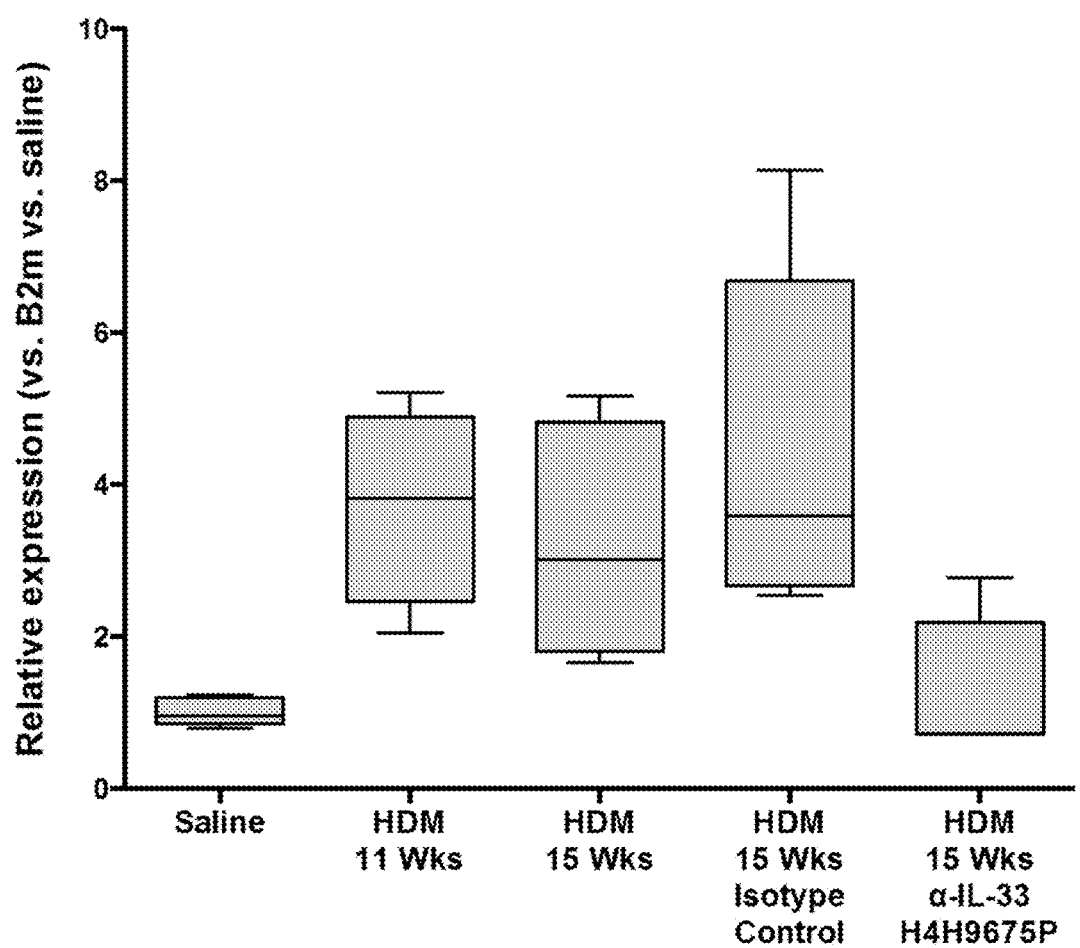
FIG. 2: Shows mouse Calcitonin (Calca) gene expression in the chronic HDM model.

In addition, the chronic house dust mite (HDM) challenge model, which was used as a model of severe, progressive lung inflammation following exposure to an allergen, showed that calcitonin gene expression is upregulated in the lungs of mice upon chronic HDM challenge, but the expression of calcitonin is reduced significantly in the lungs of mice that have been treated with an IL-33 antagonist (H4H9675P anti-IL-33 antibody). Treatment with an isotype matched negative control antibody had no effect on the level of calcitonin gene expression (FIG. 2).

Figure 3:
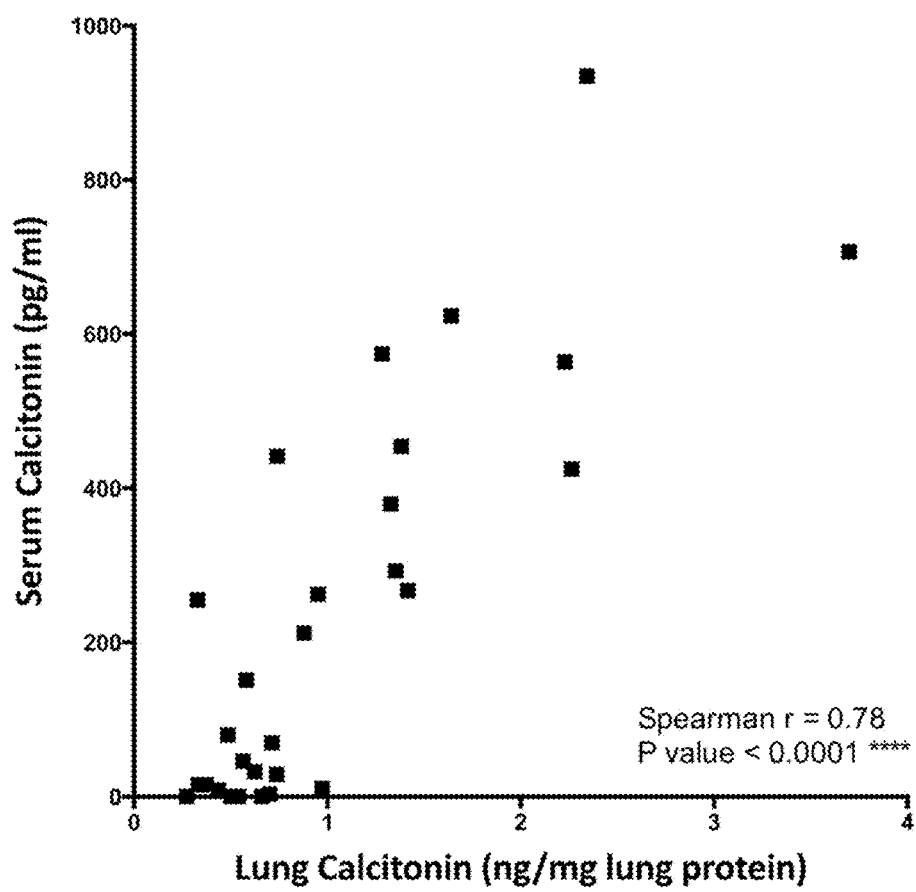
FIG. 3: Shows the correlation between serum and lung Calcitonin (CT) levels in the chronic HDM model.
Figure 4:
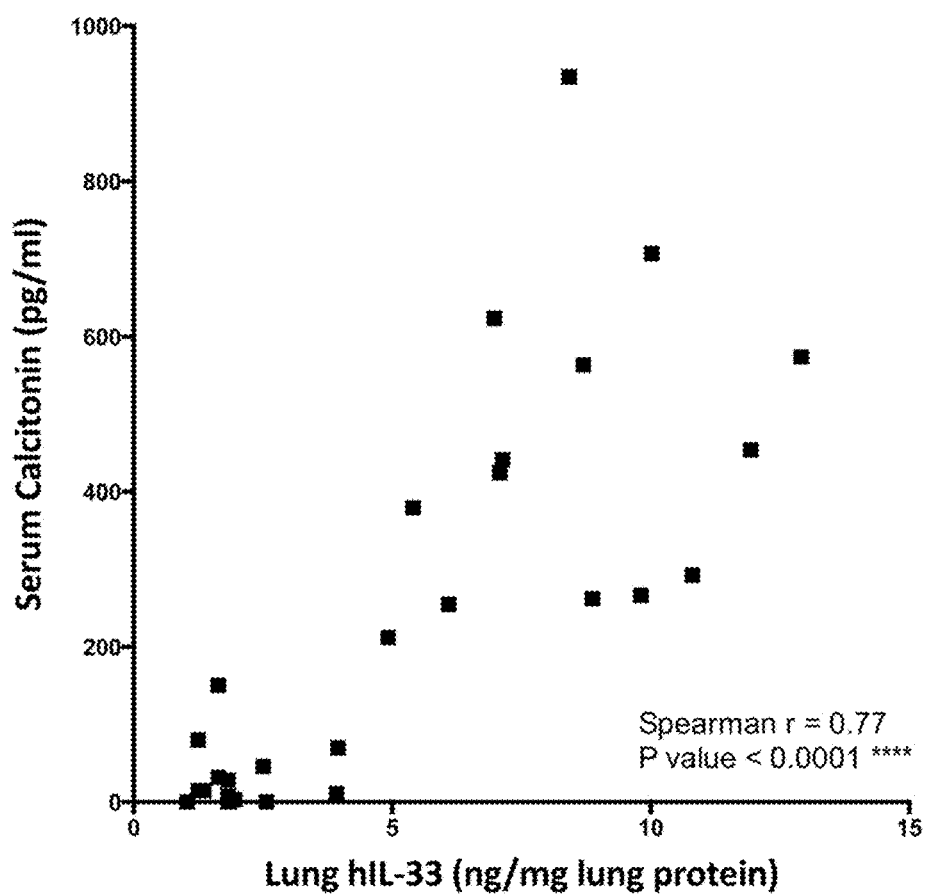
FIG. 4: Shows the correlation of serum Calcitonin (CT) and lung IL-33 levels in the chronic HDM model.

In addition, serum calcitonin was also elevated in this HDM mouse model and the level of serum calcitonin correlated with the level of calcitonin seen in the lungs of these mice (See FIG. 3). Moreover, the level of serum calcitonin correlated with the elevated levels of IL-33 observed in this HDM mouse model (See FIG. 4), suggesting that calcitonin could be used as a potential biomarker for IL-33 in an IL-33 mediated disease process (e.g. an allergic response).

Figure 5A:
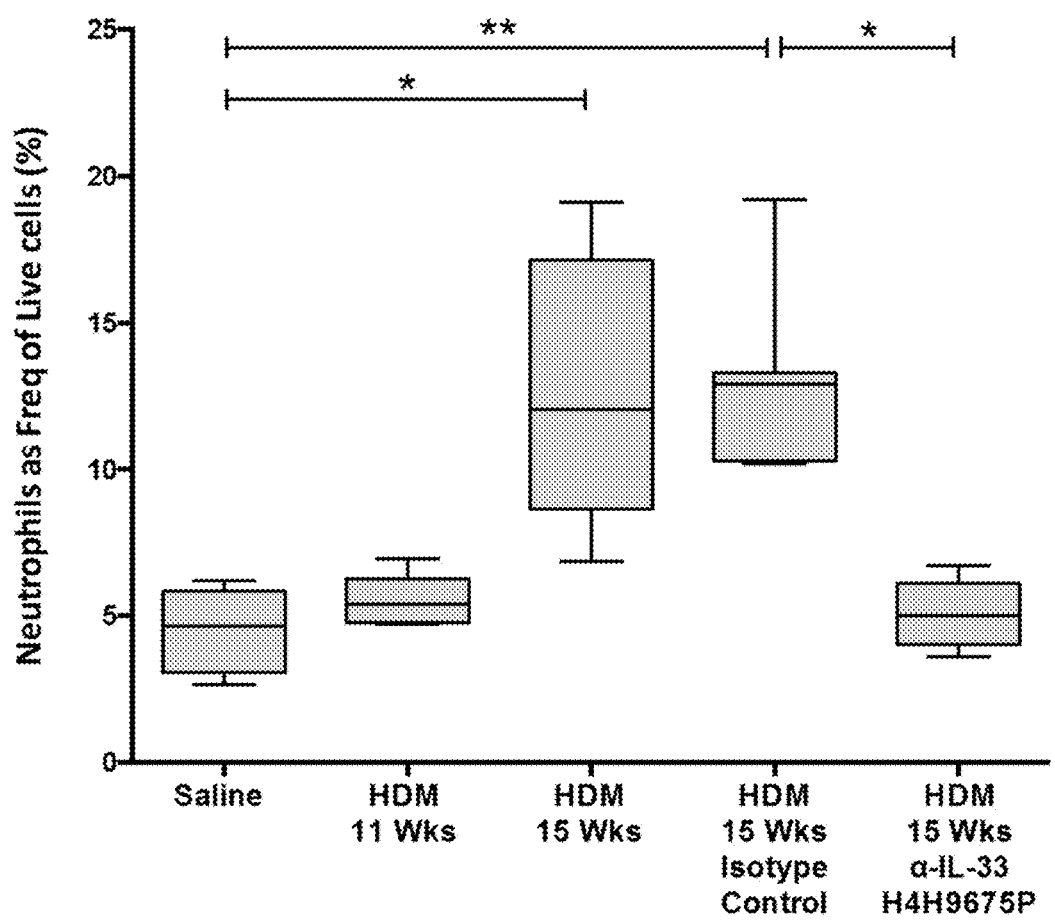
FIGS. 5A, 5B and 5C: Show the parameters affected by anti-IL-33 treatment in chronic HDM model.
Figure 5B:
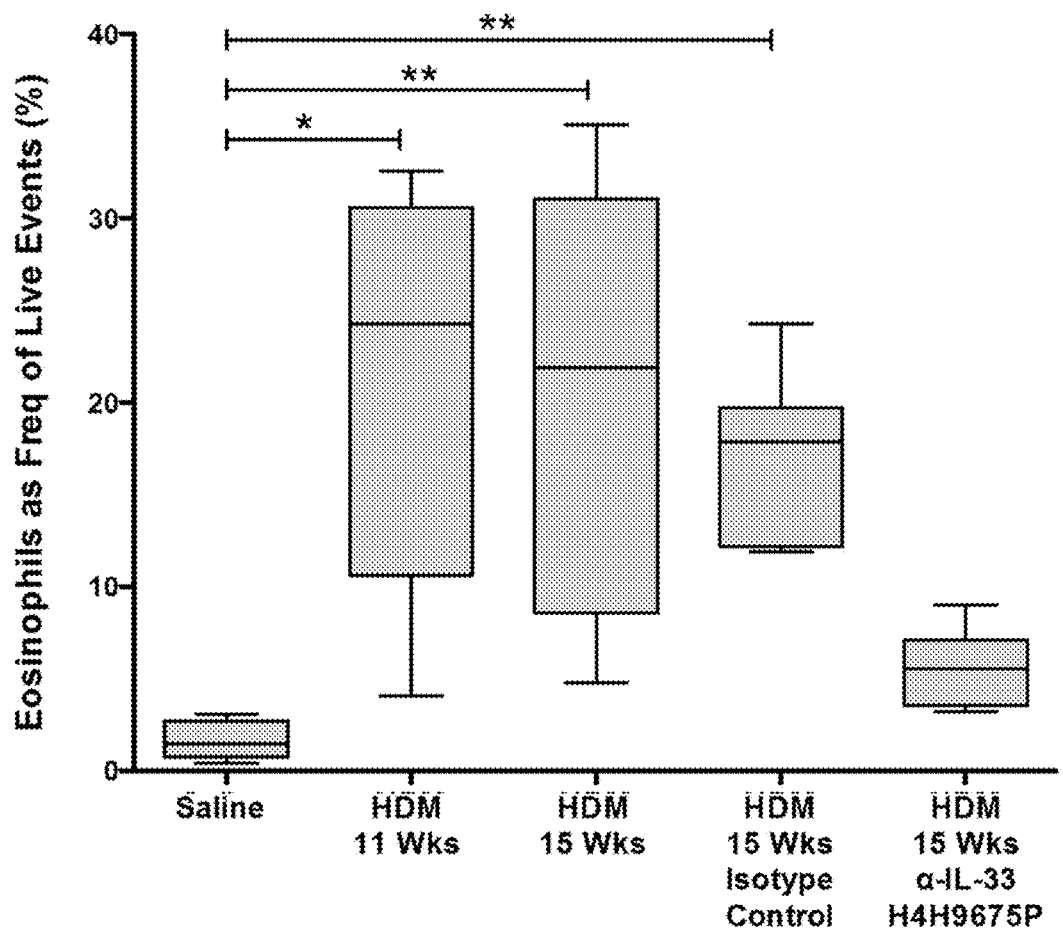
Figure 5C:
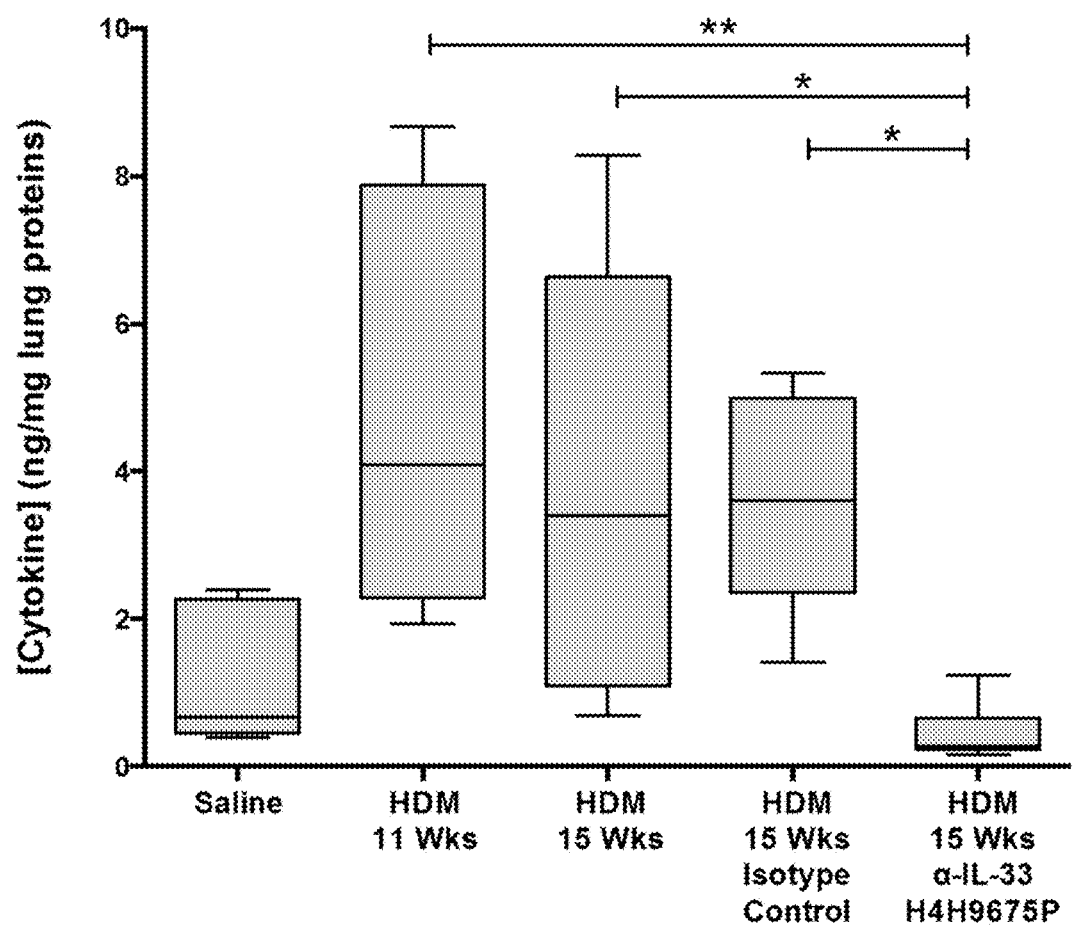

In terms of IL-33 mediated disease parameters, the frequency of lung neutrophils, lung eosinophils and IL5 levels were studied in this HDM model. By 15 weeks after challenge with house dust mite allergen, all three parameters were found to be elevated (See FIGS. 5A (neutrophils), 5B (eosinophils) and 5C (IL-5)). However, mice that received the IL-33 antibody H4H9675P showed significantly fewer neutrophils, eosinophils and IL-5 in their lungs compared to the mice challenged with allergen and left untreated, or administered a negative isotype control antibody (See FIGS. 5A, 5B and 5C).

Figure 6A:
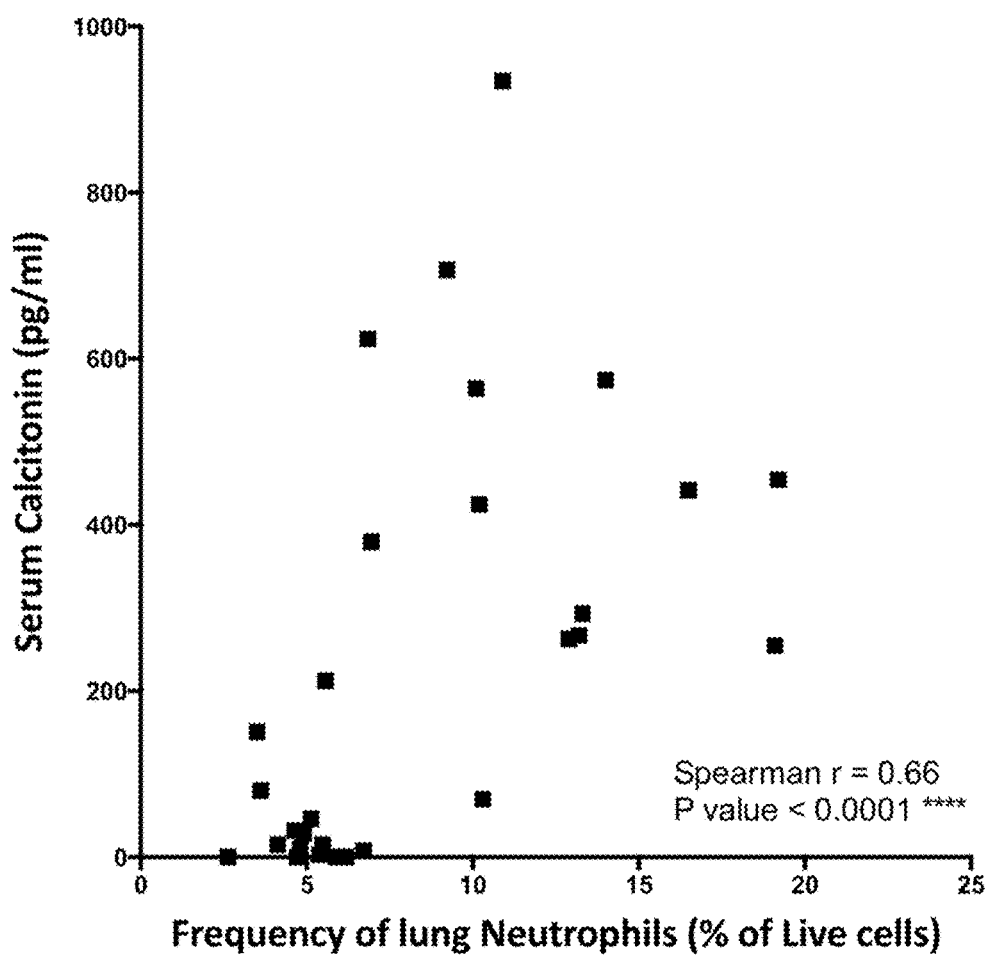
FIGS. 6A, 6B and 6C: Show the correlation of serum Calcitonin (CT) and the parameters affected by anti-IL-33 treatment in the chronic HDM model.
Figure 6B:
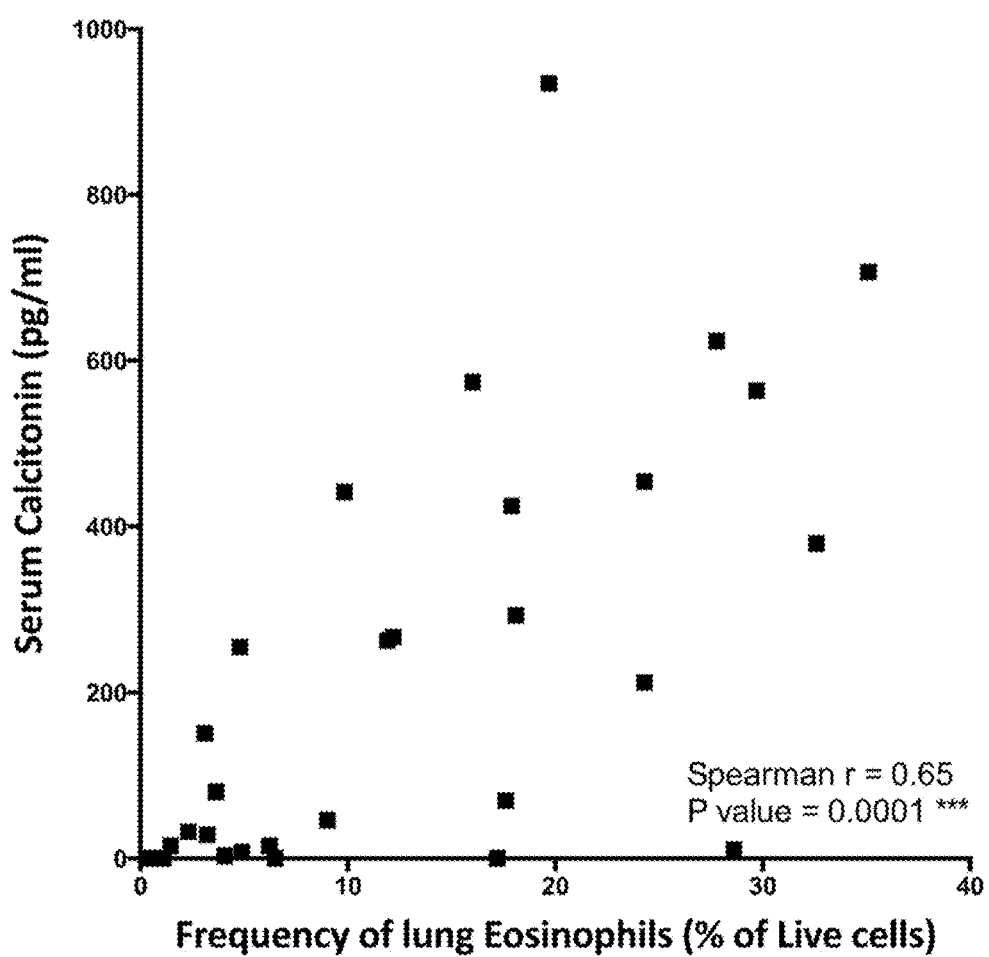
Figure 6C:
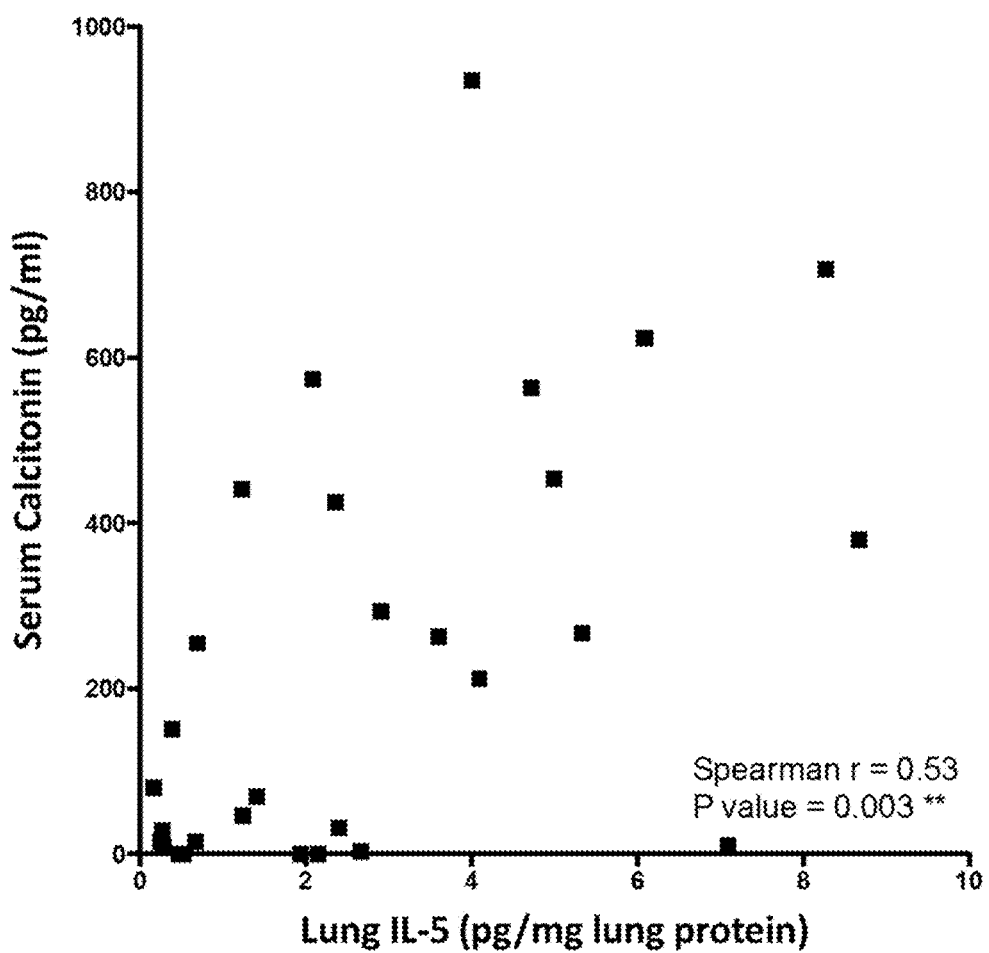

Furthermore, there was a significant correlation between serum calcitonin levels and the three disease parameters studied. FIG. 6A shows the correlation between serum calcitonin and lung neutrophils. FIG. 6B shows the correlation between serum calcitonin and lung eosinophils and FIG. 6C shows the correlation between serum calcitonin and lung IL-5 levels.

Figure 7A:
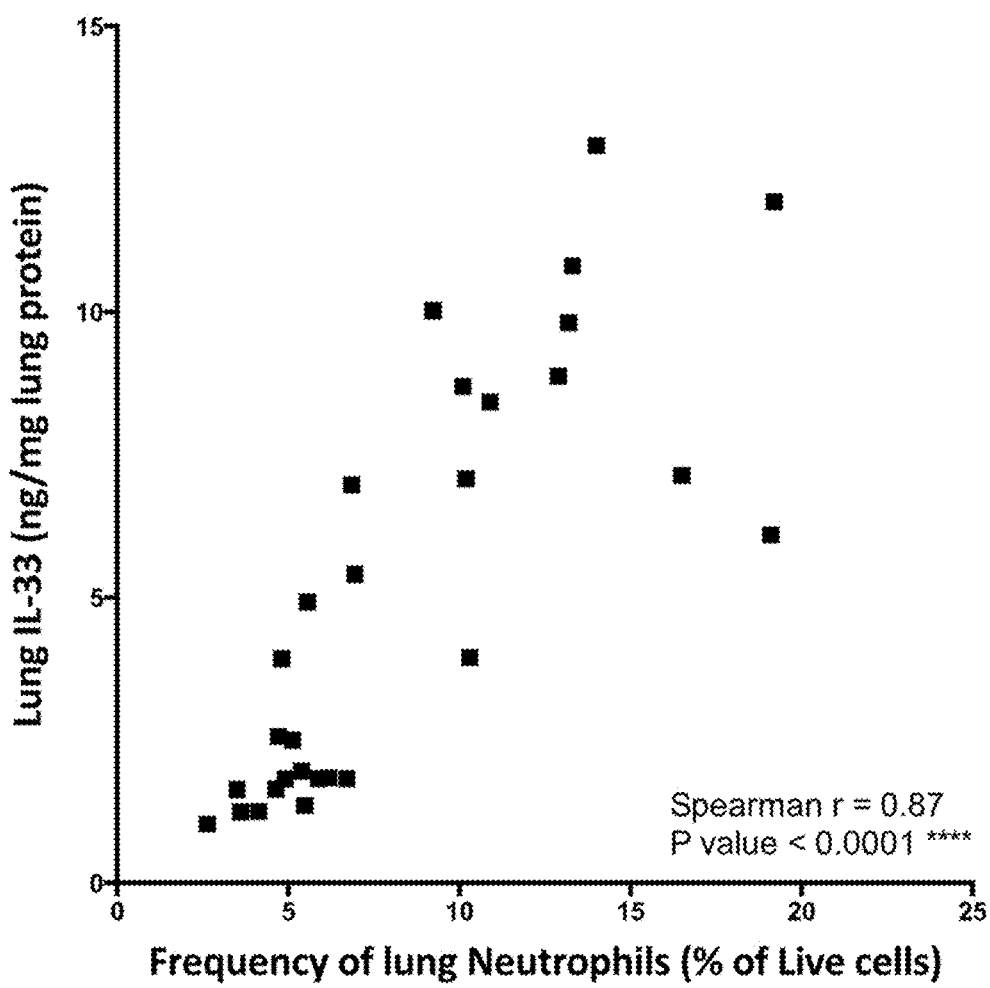
FIGS. 7A, 7B and 7C: Show the correlation of lung IL-33 levels and the parameters affected by anti-IL-33 treatment in the chronic HDM model.
Figure 7B:
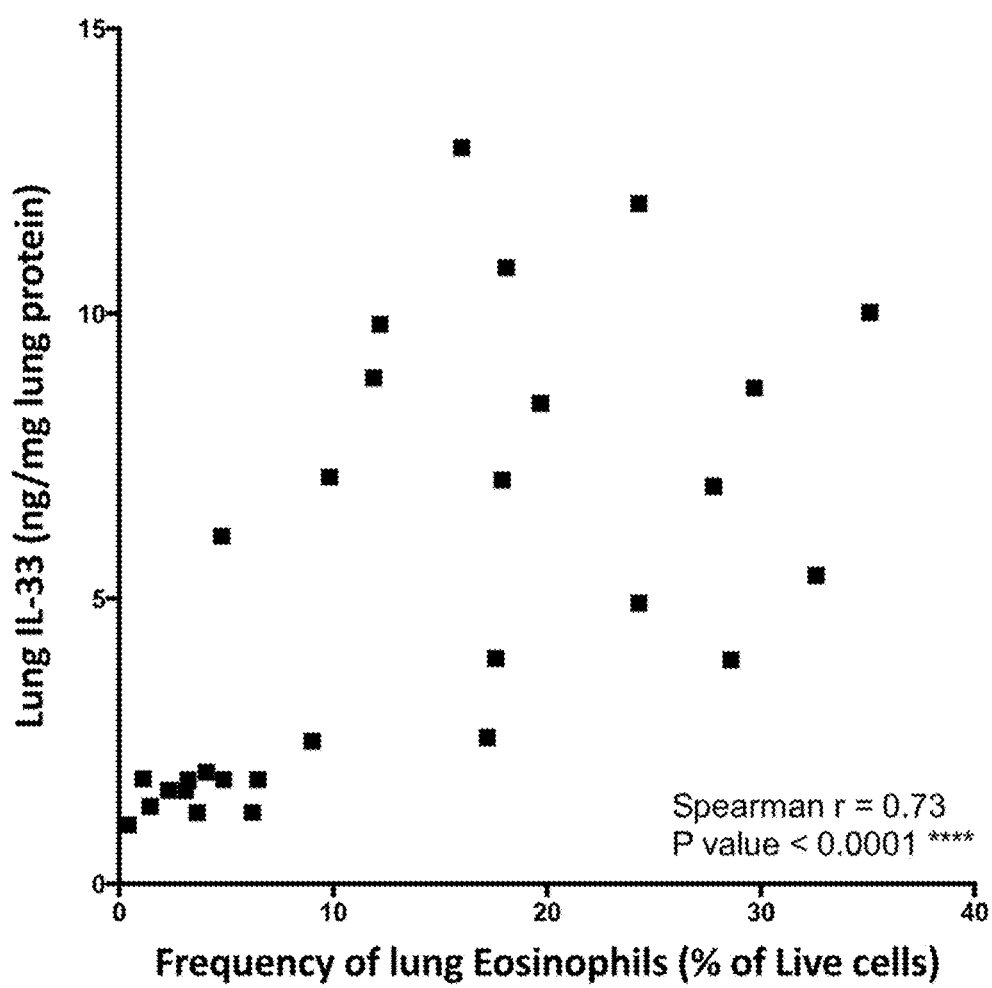
Figure 7C:
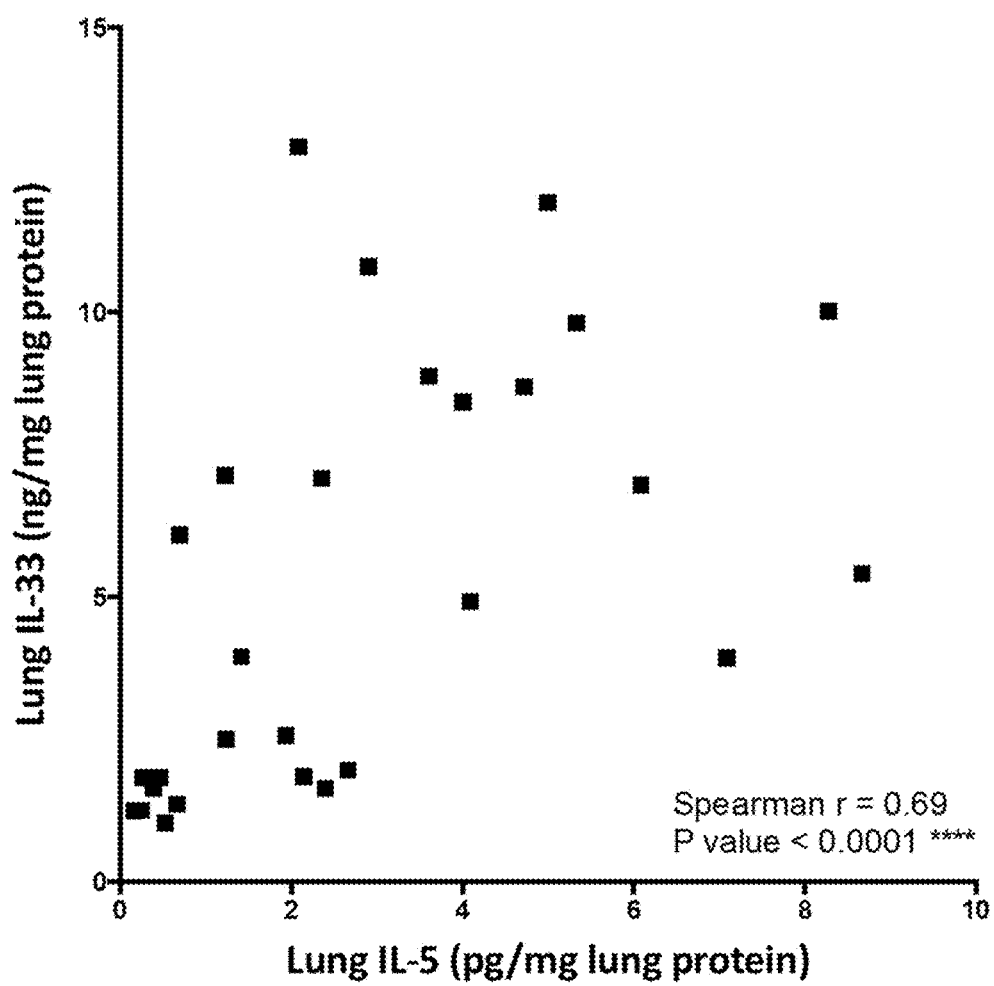

In addition, there was a significant correlation between lung IL-33 levels and the frequency of lung neutrophils (FIG. 7A), lung eosinophils (FIG. 7B) and lung IL-5 levels (FIG. 7C).

In summary, the data obtained from the house dust mite model indicate that there is a significant correlation between the level of IL-33, the frequency of at least three disease parameters associated with this model of chronic allergy and the expression of calcitonin. As such, this information suggests that calcitonin may be one biomarker of disease severity and/or progression in a mammal and furthermore, the data suggest that calcitonin may be used to assess the effectiveness of therapy with an IL-33 antagonist as described herein.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for diagnosing and treating an interleukin-33 (IL-33) mediated inflammatory disease or disorder of the airway and/or lungs in a subject, the method comprising:
   (a) obtaining a biological sample from the subject and measuring a level of a biomarker selected from calcitonin, procalcitonin or calcitonin gene-related peptide (CGRP) in the sample;
   (b) diagnosing the subject with an IL-33 mediated inflammatory disease or disorder of the airway and/or lungs when the level of calcitonin, procalcitonin or CGRP is elevated relative to a reference level of the calcitonin, procalcitonin or CGRP, respectively; and
   (c) administering to the subject a pharmaceutical composition comprising a therapeutically effective amount of an interleukin-33 antagonist, wherein the interleukin-33 antagonist is an anti-IL-33 antibody or antigen-binding fragment thereof.

2. The method of claim 1, wherein the biomarker is calcitonin.

3. The method of claim 1, wherein the IL-33 antagonist is an anti-IL-33 antibody.

4. The method of claim 1, wherein the anti-IL-33 antibody or antigen-binding fragment is an isolated human monoclonal antibody or antigen-binding fragment thereof that specifically binds human interleukin-33 (IL-33), and comprises: (a) the complementarity determining regions (CDRs) of a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274, 290, and 308; and (b) the CDRs of a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, and 316.

5. The method of claim 1, wherein the anti-IL-33 antibody or antigen-binding fragment thereof comprises the heavy and light chain CDRs of a HCVR/LCVR amino acid sequence pair selected from the group consisting of: SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, and 308/316.

6. The method of claim 1, wherein the antibody or antigen-binding fragment comprises HCDR1-HCDR2-HCDR3-LCDR1-LCDR2-LCDR3 domains, respectively, selected from the group consisting of: SEQ ID NOs: 4-6-8-12-14-16; 20-22-24-28-30-32; 36-38-40-44-46-48; 52-54-56-60-62-64; 68-70-72-76-78-80; 84-86-88-92-94-96; 100-102-104-108-110-112; 116-118-120-124-126-128; 132-134-136-140-142-144; 148-150-152-156-158-160; 164-166-168-172-174-176; 180-182-184-188-190-192; 196-198-200-204-206-208; 212-214-216-220-222-224; 228-230-232-236-238-240; 244-246-248-252-254-256; 260-262-264-268-270-272; 276-278-280-284-286-288; 292-294-296-300-302-304; and 310-312-314-318-320-322.

7. The method of claim 1, wherein the antibody or antigen-binding fragment comprises: (a) a heavy chain variable region (HCVR) having an amino acid sequence selected from the group consisting of SEQ ID NOs: 2, 18, 34, 50, 66, 82, 98, 114, 130, 146, 162, 178, 194, 210, 226, 242, 258, 274, 290, and 308; and (b) a light chain variable region (LCVR) having an amino acid sequence selected from the group consisting of SEQ ID NOs: 10, 26, 42, 58, 74, 90, 106, 122, 138, 154, 170, 186, 202, 218, 234, 250, 266, 282, 298, and 316.

8. The method of claim 1, further comprising administering an effective amount of a second therapeutic agent useful for diminishing at least one symptom of an IL-33 mediated inflammatory disease or disorder of the airway and/or lungs.

9. The method of claim 8, wherein the second therapeutic agent is selected from the group consisting of a non-steroidal anti-inflammatory (NSAID), a corticosteroid, a bronchial dilator, an antihistamine, epinephrine, a decongestant, a thymic stromal lymphopoietin (TSLP) antagonist, an IL-13 antagonist, an IL-4 antagonist, an IL-4/IL-13 dual antagonist, an IL-5 antagonist, an IL-6 antagonist, an IL-12/23 antagonist, an IL-22 antagonist, an IL-25 antagonist, an IL-17 antagonist, an IL-31 antagonist, an oral PDE4 inhibitor and another IL-33 antagonist or a different antibody or receptor based antagonist to IL-33.

10. The method of claim 1, wherein the biomarker is calcitonin, and wherein the calcitonin level increases in the serum of the subject having an IL-33 mediated inflammatory disease or disorder of the airway and/or lungs, and wherein the increase in serum calcitonin correlates with an increased level of calcitonin and IL-33 in the lungs of the subject.

11. The method of claim 10, wherein the increased level of calcitonin in the serum of the subject having an IL-33 mediated inflammatory disease or disorder of the airway and/or lungs is reduced to the reference level following treatment with the anti-IL-33 antagonist.

12. The method of claim 1, wherein the biomarker is calcitonin, the biological sample is a serum sample, and the reference level of calcitonin is 5 pg/mL for a female subject and 10 pg/mL for a male subject.

13. The method of claim 1, wherein the IL-33 mediated inflammatory disease or disorder of the airway and/or lungs is selected from the group consisting of asthma, allergy, allergic rhinitis, allergic airway inflammation, and chronic obstructive pulmonary disease (COPD).

14. The method of claim 1, wherein the biological sample from the subject is a solid tissue sample, a cell sample, or a blood sample.

15. The method of claim 14, wherein the solid tissue sample is from the lung.

16. The method of claim 14, wherein the cell sample is a sputum cell sample, bronchoalveolar lavage cell sample, nasal polyps cell sample, or lung biopsy cell sample.

17. The method of claim 14, wherein the blood sample is whole blood, plasma, or serum.

18. The method of claim 7, wherein the antibody or antigen-binding fragment comprises a HCVR/LCVR pair comprising the amino acid sequences of SEQ ID NO: 274/282.

19. The method of claim 13, wherein the IL-33 mediated inflammatory disease or disorder of the airway and/or lungs is asthma.

20. The method of claim 19, wherein the asthma comprises an asthma exacerbation.

21. The method of claim 13, wherein the IL-33 mediated inflammatory disease or disorder of the airway and/or lungs is COPD.

22. The method of claim 13, wherein the IL-33 mediated inflammatory disease or disorder of the airway and/or lungs is allergic airway inflammation.

23. A method for diagnosing and treating an interleukin-33 (IL-33) mediated inflammatory disease or disorder of the airway and/or lungs in a subject, the method comprising:

(a) obtaining a biological sample from the subject and measuring a level of calcitonin in the sample;

(b) diagnosing the subject with an IL-33 mediated inflammatory disease or disorder of the airway and/or lungs when the level of calcitonin is elevated relative to a reference level of the calcitonin; and (c) administering to the subject a pharmaceutical composition comprising a therapeutically effective amount of an interleukin-33 antagonist, wherein the interleukin-33 antagonist is an anti-IL-33 antibody or antigen-binding fragment thereof comprising HCDR1-HCDR2-HCDR3-LCDR1-LCDR2-LCDR3 domains, respectively, comprising the amino acid sequences of SEQ ID NOs: 276-278-280-284-286-288.

24. The method of claim 23, wherein the anti-IL-33 antibody or antigen-binding fragment comprises a heavy chain variable region comprising the amino acid sequence of SEQ ID NO: 274 and a light chain variable region comprising the amino acid sequence of SEQ ID NO: 282.

25. The method of claim 24, wherein the anti-IL-33 antibody or antigen-binding fragment is a human anti-IL-33 antibody comprising a human IgG4 constant region.

26. The method of claim 23, wherein the IL-33 mediated inflammatory disease or disorder of the airway and/or lungs is asthma.

27. The method of claim 23, wherein the IL-33 mediated inflammatory disease or disorder of the airway and/or lungs is COPD.

* * * * *